US009956282B2

(12) United States Patent
Cook et al.

(10) Patent No.: US 9,956,282 B2
(45) Date of Patent: May 1, 2018

(54) BACTERIAL COMPOSITIONS AND METHODS OF USE THEREOF FOR TREATMENT OF IMMUNE SYSTEM DISORDERS

(71) Applicant: Seres Therapeutics, Inc., Cambridge, MA (US)

(72) Inventors: David N. Cook, Brooklyn, NY (US); David Arthur Berry, Brookline, MA (US); Geoffrey von Maltzahn, Boston, MA (US); Matthew R. Henn, Somerville, MA (US); Han Zhang, Oakton, VA (US); Brian Goodman, Boston, MA (US)

(73) Assignee: Seres Therapeutics, Inc., Cambridge, MA (US)

( * ) Notice: Subject to any disclaimer, the term of this patent is extended or adjusted under 35 U.S.C. 154(b) by 0 days. days.

(21) Appl. No.: 15/104,873

(22) PCT Filed: Dec. 16, 2014

(86) PCT No.: PCT/US2014/070684
§ 371 (c)(1),
(2) Date: Jun. 15, 2016

(87) PCT Pub. No.: WO2015/095241
PCT Pub. Date: Jun. 25, 2015

(65) Prior Publication Data
US 2016/0317653 A1 Nov. 3, 2016

Related U.S. Application Data

(60) Provisional application No. 61/916,761, filed on Dec. 16, 2013.

(51) Int. Cl.
*A61K 39/35* (2006.01)
*A23L 33/135* (2016.01)
*A61K 35/742* (2015.01)
*A61K 45/06* (2006.01)
*A61K 49/00* (2006.01)
*G01N 33/68* (2006.01)
*A61K 39/00* (2006.01)
*A61K 35/00* (2006.01)

(52) U.S. Cl.
CPC ............ *A61K 39/35* (2013.01); *A23L 33/135* (2016.08); *A61K 35/742* (2013.01); *A61K 45/06* (2013.01); *A61K 49/0004* (2013.01); *G01N 33/6863* (2013.01); *A23V 2002/00* (2013.01); *A61K 2035/115* (2013.01); *A61K 2039/52* (2013.01); *A61K 2039/54* (2013.01); *A61K 2039/545* (2013.01); *A61K 2039/55544* (2013.01); *A61K 2039/577* (2013.01); *A61K 2039/58* (2013.01); *G01N 2333/52* (2013.01)

(58) Field of Classification Search
None
See application file for complete search history.

(56) References Cited

U.S. PATENT DOCUMENTS

| 3,009,864 | A | 11/1961 | Gordon-Aldterton et al. |
| 3,228,838 | A | 1/1966 | Rinfret |
| 3,608,030 | A | 11/1971 | Grant |
| 4,077,227 | A | 3/1978 | Larson |
| 4,205,132 | A | 5/1980 | Sandine |
| 4,655,047 | A | 4/1987 | Temple |
| 4,689,226 | A | 8/1987 | Nurmi |
| 4,839,281 | A | 6/1989 | Gorbach et al. |
| 5,196,205 | A | 3/1993 | Borody |
| 5,425,951 | A | 6/1995 | Goodrich |
| 5,436,002 | A | 7/1995 | Payne |
| 5,443,826 | A | 8/1995 | Borody |
| 5,599,795 | A | 2/1997 | McCann |
| 5,648,206 | A | 7/1997 | Goodrich |
| 5,951,977 | A | 9/1999 | Nisbet et al. |
| 5,965,128 | A | 10/1999 | Doyle et al. |
| 6,589,771 | B1 | 7/2003 | Marshall |
| 6,645,530 | B1 | 11/2003 | Borody |
| 7,427,398 | B2 | 9/2008 | Baillon et al. |
| 7,628,982 | B2 | 12/2009 | Klaviniskis |
| 7,632,520 | B2 | 12/2009 | Khandelwal |
| 7,708,988 | B2 | 5/2010 | Farmer |
| 7,731,976 | B2 | 6/2010 | Cobb |
| 7,763,420 | B2 | 7/2010 | Stritzker et al. |
| 7,981,411 | B2 | 7/2011 | Nadeau et al. |
| 7,998,473 | B2 | 8/2011 | Boileau et al. |
| 8,021,654 | B2 | 9/2011 | Rehberger et al. |

(Continued)

FOREIGN PATENT DOCUMENTS

| CN | 102131928 A | 7/2011 |
| EA | 006847 B1 | 4/2006 |

(Continued)

OTHER PUBLICATIONS

Kim et al. (J. Microbiol. Biotechnol., 18:1393-1400, 2008).*
Prioult et al. (Clin. Diagnos. Lab. Immunol., 10:787-792, 2003).*
Australian First Examination Report, Australian Application No. 2013347805, dated Apr. 13, 2017, 3 pages.
Chiu, C.-H. et al., "Rapid Identification of *Salmonella* Serovars in Feces by Specific Detection of Virulence Genes, invA and spvC, by an Enrichment Broth Culture-Multiplex PCR Combination Assay," Journal of Clinical Microbiology, Oct. 1996, pp. 2619-2622, vol. 34, No. 10.
Coleman, W.H., "Mechanism of Killing Spores of Bacillus Cereus and Bacillus Megaterium by Wet Heat," The Society for Applied Microbiology, Letters in Applied Microbiology, 2010. pp. 507-514, vol. 50.

(Continued)

*Primary Examiner* — Brian Gangle
(74) *Attorney, Agent, or Firm* — Fenwick & West LLP

(57) ABSTRACT

Provided are compositions containing combinations of bacteria useful for the maintenance or restoration of a healthy microbiota in the gastrointestinal tract, or other niche of a mammalian subject, and methods for use thereof, in particular for the treatment, inhibition, or prevention of immune disorders such as allergies and asthma.

11 Claims, 11 Drawing Sheets

(56) References Cited

U.S. PATENT DOCUMENTS

| | | |
|---|---|---|
| 8,034,601 B2 | 10/2011 | Boileau |
| 8,039,006 B2 | 10/2011 | Prato |
| 8,147,482 B2 | 4/2012 | Shimizu |
| 8,187,590 B2 | 5/2012 | Farmer |
| 8,236,508 B2 | 8/2012 | Mutharasan |
| 8,388,996 B2 | 3/2013 | Gehling |
| 8,460,648 B2 | 6/2013 | Borody |
| 8,906,668 B2 | 12/2014 | Henn et al. |
| 9,011,834 B1 | 4/2015 | McKenzie et al. |
| 9,028,841 B2 | 5/2015 | Henn et al. |
| 9,180,147 B2 | 11/2015 | McKenzie et al. |
| 9,408,872 B2 | 8/2016 | Borody |
| 9,446,080 B2 | 9/2016 | McKenzie et al. |
| 9,808,519 B2 | 11/2017 | Honda et al. |
| 2001/0036453 A1 | 11/2001 | Reid |
| 2004/0028689 A1 | 2/2004 | Borody |
| 2004/0170617 A1 | 9/2004 | Finegold |
| 2005/0048515 A1 | 3/2005 | Garner |
| 2005/0180962 A1 | 8/2005 | Raz |
| 2006/0046246 A1 | 3/2006 | Zeng et al. |
| 2006/0188523 A1 | 8/2006 | Pei |
| 2006/0233830 A1 | 10/2006 | Wong |
| 2007/0141139 A1 | 6/2007 | Vandenberg |
| 2008/0213752 A1 | 9/2008 | Stave et al. |
| 2009/0197249 A1 | 8/2009 | Gillevet |
| 2010/0074872 A1 | 3/2010 | Blaser et al. |
| 2010/0215745 A1 | 8/2010 | Lazzari et al. |
| 2011/0081320 A1 | 4/2011 | Westall et al. |
| 2011/0113863 A1 | 5/2011 | Fuhrmann et al. |
| 2011/0189132 A1 | 8/2011 | Garner et al. |
| 2011/0280840 A1 | 11/2011 | Blaser |
| 2012/0020950 A1 | 1/2012 | Davis et al. |
| 2012/0021429 A1 | 1/2012 | Rublee |
| 2012/0021921 A1 | 1/2012 | Scott |
| 2012/0058094 A1 | 3/2012 | Blaser |
| 2012/0064592 A1 | 3/2012 | O'Mullan et al. |
| 2012/0128633 A1 | 5/2012 | Veiga et al. |
| 2012/0128634 A1 | 5/2012 | Veiga |
| 2012/0148629 A1 | 6/2012 | Holvoet et al. |
| 2012/0149584 A1 | 6/2012 | Olle |
| 2012/0165215 A1 | 6/2012 | Andersen |
| 2012/0177650 A1 | 7/2012 | Borody |
| 2012/0207726 A1 | 8/2012 | Lipkin |
| 2012/0238468 A1 | 9/2012 | Tuk |
| 2012/0264637 A1 | 10/2012 | Brodie |
| 2012/0276149 A1 | 11/2012 | Littman |
| 2012/0276201 A1 | 11/2012 | Trachtman |
| 2012/0315249 A1 | 12/2012 | Olmstead |
| 2013/0017999 A1 | 1/2013 | Fremont |
| 2013/0022575 A1 | 1/2013 | Cassity |
| 2013/0045274 A1 | 2/2013 | Hlavka |
| 2013/0045874 A1 | 2/2013 | Ehrlich |
| 2013/0121968 A1 | 5/2013 | Quay |
| 2013/0149339 A1 | 6/2013 | Honda |
| 2013/0149375 A1 | 6/2013 | Geall |
| 2013/0266539 A1 | 10/2013 | Borody |
| 2014/0045744 A1 | 2/2014 | Gordon |
| 2014/0147417 A1 | 5/2014 | Sadowsky et al. |
| 2014/0147425 A1 | 5/2014 | Henn et al. |
| 2014/0199281 A1 | 7/2014 | Henn et al. |
| 2014/0342438 A1 | 11/2014 | Allen-Vercoe et al. |
| 2015/0190435 A1 | 7/2015 | Henn et al. |
| 2016/0271188 A1 | 9/2016 | Berry et al. |

FOREIGN PATENT DOCUMENTS

| | | |
|---|---|---|
| EP | 0033584 A3 | 1/1981 |
| EP | 0446069 A1 | 9/1991 |
| EP | 0456418 A2 | 11/1991 |
| EP | 0433299 A4 | 4/1992 |
| EP | 1107772 B1 | 4/2006 |
| EP | 1631312 B1 | 9/2008 |
| EP | 2337569 A2 | 6/2011 |
| EP | 2338989 A1 | 6/2011 |
| EP | 2519108 A1 | 11/2012 |
| EP | 2684469 A1 | 1/2014 |
| EP | 0479820 B1 | 7/2014 |
| EP | 2626076 A1 | 8/2014 |
| EP | 2750682 B1 | 5/2016 |
| JP | 6-56679 A | 3/1994 |
| JP | 2007-332083 A | 12/2007 |
| JP | 2010-539179 T | 12/2010 |
| JP | 5 019563 B2 | 9/2012 |
| RU | 2035186 C1 | 5/1995 |
| RU | 2439145 C2 | 1/2012 |
| WO | WO 90/01335 A1 | 2/1990 |
| WO | WO 1997/009886 A1 | 3/1997 |
| WO | WO 98/26787 A1 | 6/1998 |
| WO | WO 2000/010582 A2 | 3/2000 |
| WO | WO 01/93904 A1 | 12/2001 |
| WO | WO 2002/007741 A1 | 1/2002 |
| WO | WO 02/43649 A2 | 6/2002 |
| WO | WO 2005/017095 A2 | 2/2005 |
| WO | WO 2005/110445 A2 | 11/2005 |
| WO | WO 2006/012586 A2 | 2/2006 |
| WO | WO 2007/036230 A1 | 4/2007 |
| WO | WO 2007/136553 A2 | 11/2007 |
| WO | WO 2008/076696 A2 | 6/2008 |
| WO | WO 2008/083157 A2 | 7/2008 |
| WO | WO 2010/030997 A1 | 3/2010 |
| WO | WO 2010/062369 A2 | 6/2010 |
| WO | WO 2010/124387 A1 | 11/2010 |
| WO | WO 2010/151842 A2 | 12/2010 |
| WO | WO 2011/005756 A1 | 1/2011 |
| WO | WO 2011/022542 A2 | 2/2011 |
| WO | WO 2011022660 A1 | 2/2011 |
| WO | WO 2011/033310 A1 | 3/2011 |
| WO | WO 2011/043654 A1 | 4/2011 |
| WO | WO 2011/046616 A3 | 4/2011 |
| WO | WO 2011/060123 A1 | 5/2011 |
| WO | WO 2011/094027 A1 | 8/2011 |
| WO | WO 2011/103123 A2 | 8/2011 |
| WO | WO 2011/107481 A2 | 9/2011 |
| WO | WO 2011/107482 A2 | 9/2011 |
| WO | WO 2011/113801 A1 | 9/2011 |
| WO | WO 2011/152566 A2 | 12/2011 |
| WO | WO 2012/009712 A2 | 1/2012 |
| WO | WO 2012/016287 A2 | 2/2012 |
| WO | WO 2012/033814 A2 | 3/2012 |
| WO | WO 2012/045150 A1 | 4/2012 |
| WO | WO 2012/064981 A2 | 5/2012 |
| WO | WO 2012/108830 A1 | 8/2012 |
| WO | WO 2012/116289 A2 | 8/2012 |
| WO | WO 2012/122478 A1 | 9/2012 |
| WO | WO 2012/122522 A2 | 9/2012 |
| WO | WO 2012/142605 A1 | 10/2012 |
| WO | WO 2012/148991 A1 | 11/2012 |
| WO | WO 2012/159023 A2 | 11/2012 |
| WO | WO 2013/019896 A1 | 2/2013 |
| WO | WO 2013/032328 A1 | 3/2013 |
| WO | WO 2013/037067 A1 | 3/2013 |
| WO | WO 2013/037068 | 3/2013 |
| WO | WO 2013/050792 A1 | 4/2013 |
| WO | WO 2013/053836 A1 | 4/2013 |
| WO | WO 2013/080561 A1 | 6/2013 |
| WO | WO 2013/166031 A1 | 11/2013 |
| WO | WO 2013/171515 A1 | 11/2013 |
| WO | WO 2013/176774 A1 | 11/2013 |
| WO | WO 2014/082050 A1 | 5/2014 |
| WO | WO 2015/095241 A2 | 6/2014 |
| WO | WO 2014/121298 A2 | 8/2014 |
| WO | WO 2014/121301 A1 | 8/2014 |
| WO | WO 2014/121302 A2 | 8/2014 |
| WO | WO 2014/121304 A1 | 8/2014 |
| WO | WO 2014/145958 A2 | 9/2014 |
| WO | WO 2014/153194 A2 | 9/2014 |
| WO | WO 2015/077794 A1 | 5/2015 |

OTHER PUBLICATIONS

Dendukuri, N., "Probiotic Therapy for the Prevention and Treatment of Clostridium Difficile-Associated Diarrhea: A Systematic Review," Canadian Medical Association Journal, Jul. 19, 2005, pp. 167-170, vol. 173, No. 2.

(56) References Cited

OTHER PUBLICATIONS

European Extended Search Report, European Application No. 14746341.8, dated Sep. 28, 2016, 10 pages.
European Partial Supplementary Report, European Application No. 14745792.3, dated Sep. 20, 2016, 11 pages.
European Partial Supplementary Report, European Application No. 14745749.3, dated Oct. 14, 2016, 6 pages.
European Extended Search Report, European Application No. 14746455.6, dated Nov. 24, 2016, 10 pages.
European Extended Search Report, European Application No. 14745792.3, dated Dec. 23, 2016, 17 pages.
European Extended Search Report, European Application No. 14745749.3, dated Jan. 23, 2017, 13 pages.
European Extended Search Report, European Application No. 13856249.1, dated Jan. 26, 2017, 19 pages.
Israel Office Action, Israel Application No. 238973, dated Apr. 20, 2017, 4 pages. (with concise explanation of relevance).
Janda, J.M. et al., "16S rRNA Gene Sequencing for Bacterial Identification in the Diagnostic Laboratory: Pluses, Perils and Pitfalls," Journal of Clinical Microbiology, Sep. 2007, pp. 2761-2764, vol. 45, No. 9.
Johnson, S. et al., "Is Primary Prevention of Clostridium Difficile Infection Possible with Specific Probiotics?" International Journal of Infectious Diseases, Nov. 2012, pp. e786-e792, vol. 16, No. 11.
McFarland, L.V. et al., "Pharmaceutical Probiotics for the Treatment of Anaerobic and Other Infections," Anaerobe, Jan. 1997, pp. 73-78, vol. 3, No. 2-3.
New Zealand Third Examination Report, New Zealand Application No. 711771, dated Nov. 4, 2016, 4 pages.
Russian First Office Action, Russian Patent Application No. 2015124366, dated Dec. 13, 2016, 12 pages.
Russian Second Office Action, Russian Patent Application No. 2015137399, dated Mar. 14, 2017, 8 pages.
Setlow, B. et al., "Mechanisms of Killing Spores of Bacillus subtilis by Acid, Alkali and Ethanol," Journal of Applied Microbiology, 2002, pp. 362-375, vol. 92.
United States Office Action, U.S. Appl. No. 14/777,252, dated Nov. 3, 2016, 16 pages.
United States Office Action, U.S. Appl. No. 14/765,810, dated Jan. 23, 2017, 20 pages.
United States Office Action, U.S. Appl. No. 14/776,676, dated Mar. 23, 2017, 9 pages.
United States Office Action, U.S. Appl. No. 14/777,252, dated May 11, 2017, 9 pages.
Aas, J., Gessert, C.E., and Bakken, J.S. (2003). Recurrent Clostridium difficile colitis: case series involving 18 patients treated with donor stool administered via a nasogastric tube. Clinical Infectious Diseases 36(5), 580-585.
Abrams, R.S., "Open-Label, Uncontrolled Trial of Bowel Sterilization and Repopulation with Normal Bowel Flora for Treatment of Inflammatory Bowel Disease," Current Therapeutic Research, Dec. 1997, pp. 1001-1012, vol. 58, No. 12.
Achtman, M., and Wagner, M. (2008). Microbial diversity and the genetic nature of microbial species. Nat. Rev. Microbiol. 6(6), 431-440.
Accoceberry, I. et al., "One-Step Purification of Enterocytozoon Bienusi Spores from Human Stools by Immunoaffinity Expanded-Bed Adsorption," Journal of Clinical Microbiology, May 2001, pp. 1974-1951, vol. 39, No. 5.
Allen-Vercoe, E., Reid, G., Viner, N., Gloor, G.B., Hota, S., Kim, P., Lee, C., O'Doherty, K., Vanner, S.J., Weese, J.S., et al. (2012). A Canadian Working Group report on fecal microbial therapy: microbial ecosystems therapeutics. Can. J. Gastroenterol. 26(7), 457-462.
Allen-Vercoe, E., Strauss, J., and Chadee, K. (2011). Fusobacterium nucleatum: an emerging gut pathogen? Gut Microbes 2(5), 294-298.
Anderson, K.F., Lonsway, D.R., Rasheed, J.K., Biddle, J., Jensen, B., Mcdougal, L.K., Carey, R.B., Thompson, a., Stocker, S., Limbago, B., et al. (2007). Evaluation of Methods to Identify the Klebsiella pneumoniae Carbapenemase in Enterobacteriaceae. J. Clin. Microbiol. 45(8), 2723-2725.

Arumugam, M., Raes, J., Pelletier, E., Paslier, D.L., Yamada, T., Mende, D.R., Fernandes, G.R., Tap, J., Bruls, T., Batto, J.-M., et al. (2011). Enterotypes of the human gut microbiome. Nature 473(7346), 174-180.
Atarashi, K., Tanoue, T., Oshima, K., Suda, W., Nagano, Y., Nishikawa, H., Fukuda, S., Saito, T., Narushima, S., Hase, K., et al. (2013). Treg induction by a rationally selected mixture of Clostridia strains from the human microbiota. Nature 500(7461), 232-236.
Atarashi, K., Tanoue, T., Shima, T., Imaoka, a., Kuwahara, T., Momose, Y., Cheng, G., Yamasaki, S., Saito, T., Ohba, Y., et al. (2011). Induction of colonic regulatory T cells by indigenous Clostridium species. Science 331(6015), 337-341.
Backhed, F. et al., (2004). The gut microbiota as an environmental factor that regulates fat storage, PNAS, Nov. 2, 2014, pp. 15718-15723, vol. 101, No. 44.
Bader, J., Albin, A., and Stahl, U. (2012). Spore-forming bacteria and their utilisation as probiotics. Benef Microbes 3(1), 67-75.
Bakken, J.S. (2009). Fecal bacteriotherapy for recurrent Clostridium difficile infection. Anaerobe 15(6), 285-289.
Bakken, J.S., Borody, T., Brandt, L.J., Brill, J.V., Demarco, D.C., Franzos, M.A., Kelly, C., Khoruts, A., Louie, T., Martinelli, L.P., et al. (2011). Treating Clostridium difficile infection with fecal microbiota transplantation. Clin. Gastroenterol. Hepatol. 9(12), 1044-1049.
Barreau, M., Pagnier, I., and La Scola, B. (2013). Improving the identification of anaerobes in the clinical microbiology laboratory through MALDI-TOF mass spectrometry. Anaerobe 22,123-125.
Bauer, T.M. et al., "Derivation and Validation of Guidelines for Stool Cultures for Enteropathogenic Bacteria Other Than Clostridium difficile in Hospitalized Adults," The Journal of the American Medical Association, Jan. 17, 2001, pp. 313-319, vol. 285.
Ben-Amor, K., Heilig, H., Smidt, H., Vaughan, E.E., Abee, T., and De Vos, W.M. (2005). Genetic diversity of viable, injured, and dead fecal bacteria assessed by fluorescence-activated cell sorting and 16S rRNA gene analysis. Applied and Environmental Microbiology 71(8), 4679-4689.
Berstad, A. et al., "Fecal Fat Determination with a Modified Titration Method," Scandinavian Journal of Gastroenterology, 2010, pp. 603-607, vol. 45.
Bhatia, A. et al., "Proionibacterium Acnes and Chronic Diseases," The Infectious Etiology of Chronic Diseases: Defining the Relationship, Enhancing the Research, and Mitigating the Effects: Workshop Summary., Knobler, S.L. et al. (eds.), 2004, pp. 74-80, may be downloaded at<URL:http://www.nap.edu/catalog/11026.html>.
Bidawid, S., Farber, J.M., Sattar, S.A., and Hayward, S. (2000). Heat inactivation of hepatitis A virus in dairy foods. J. Food Prot. 63(4), 522-528.
Bloedt, K., Riecker, M., Poppert, S., and Wellinghausen, N. (2009). Evaluation of new selective culture media and a rapid fluorescence in situ hybridization assay for identification of Clostridium difficile from stool samples. J Med Microbiol 58(7), 874-877.
Bokulich, N.A., Subramanian, S., Faith, J.J., Gevers, D., Gordon, J.I., Knight, R., Mills, D.A., and Caporaso, J.G. (2013). Quality-filtering vastly improves diversity estimates from Illumina amplicon sequencing. Nat Methods 10(1), 57-59.
Bolivar, I. et al., "Bacterial Diversity in Oral Samples of Children in Niger with Acute Noma, Acute Necrotizing Gingivitis and Healthy Controls," PLOS Neglected Tropical Diseases, Mar. 2012, pp. 1-11, vol. 6, No. 3, E1556; Uncultured Catonella sp. partial 16S rRNA Gene, Clone 402A04(oral): Nucleotide: NCBI: GenBank: AM420133.1, last accessed Mar. 12, 2014, pp. 12-13.
Borody, T.J. et al. (2011). Fecal microbiota transplantation (FMT) in multiple sclerosis. Poster abstract at American College of Gastroenterology Annual Scientific Meeting and Postgraduate Course Oct. 28, 2011.
Borody, T.J., and Khoruts, A. (2012). Fecal microbiota transplantation and emerging applications. Nat Rev Gastroenterol Hepatol 9(2), 88-96.
Borriello, S.P. (1990). The influence of the normal flora on Clostridium difficile colonisation of the gut. Ann. Med. 22(1), 61-67.

(56) References Cited

OTHER PUBLICATIONS

Borriello, S.P., and Barclay, F.E. (1985). Protection of hamsters against Clostridium difficile ileocaecitis by prior colonisation with non-pathogenic strains. J Med Microbiol 19(3), 339-350.

Borriello, S.P., and Barclay, F.E. (1986). An in-vitro model of colonisation resistance to Clostridium difficile infection. Journal of Medical Microbiology 21(4), 299309.

Borriello, S.P., and Honour, P. (1981). Simplified procedure for the routine isolation of Clostridium difficile from faeces. J Clin Pathol 34(10), 1124-1127.

Boyles, W.A., and Lincoln, R.E. (1958). Separation and concentration of bacterial spores and vegetative cells by foam flotation. Appl Microbiol 6(5), 327-334.

Brandt, L.J. (2012). Fecal Transplantation for the Treatment of Clostridium difficile Infection. Gastroenterol Hepatol (N Y) 8(3), 191-194.

Brandt, L.J., Aroniadis, O.C., Mellow, M., Kanatzar, A., Kelly, C., Park, T., Stollman, N., Rohlke, F., and Surawicz, C. (2012). Long-Term Follow-Up of Colonoscopic Fecal Microbiota Transplant for Recurrent Clostridium difficile Infection. The American Journal of Gastroenterology 107(7), 1079-1087.

Bräuniger, S., Peters, J., Borchers, U., and Kao, M. (2000). Further studies on thermal resistance of bovine parvovirus against moist and dry heat. International Journal of Hygiene and Environmental Health 203(1), 71-75.

Broda, D.M., De Lacy, K.M., and Bell, R.G. (1998). Efficacy of heat and ethanol spore treatments for the isolation of psychrotrophic Clostridium spp. associated with the spoilage of chilled vacuum-packed meats. International Journal of Food Microbiology 39(1-2), 61-68.

Brosius, J. et al., "Complete Nucleotide Sequence of a 16S Ribosomal RNA Gene from Eschericia Coli," Proc. Natl. Acad. Sci., Oct. 1978, pp. 4801-4805, vol. 75, No. 10.

Bueche, M., Wunderlin, T., Roussel-Delif, L., Junier, T., Sauvain, L., Jeanneret, N., and Junier, P. (2013). Quantification of Endospore-Forming Firmicutes by Quantitative PCR with the Functional Gene spo0A. Applied and Environmental Microbiology 79(17), 5302-5312.

Buffie, C.G., and Pamer, E.G. (2013). Microbiota-mediated colonization resistance against intestinal pathogens. Nature Reviews Immunology 13(11), 790-801.

Burke, C.J., Hsu, T.A., and Volkin, D.B. (1999). Formulation, stability, and delivery of live attenuated vaccines for human use. Crit Rev Ther Drug Carrier Syst 16(1), 1-83.

Cani, P.D., Possemiers, S., Wiele, T.V. De, Guiot, Y., Everard, A., Rottier, O., Geurts, L., Naslain, D., Neyrinck, A., Lambert, D.M., et al. (2009). Changes in gut microbiota control inflammation in obese mice through a mechanism involving GLP-2-driven improvement of gut permeability. Gut 58(8), 1091-1103.

Carvalho, A.S., Silva, J., Ho, P., Teixeira, P., Malcata, F.X., and Gibbs, P. (2008). Effects of Various Sugars Added to Growth and Drying Media upon Thermotolerance and Survival throughout Storage of Freeze-Dried Lactobacillus delbrueckii ssp. bulgaricus. Biotechnology Progress 20(1), 248-254.

Champagne, C.P., Mondou, F., Raymond, Y., and Roy, D. (1996). Effect of polymers and storage temperature on the stability of freeze-dried lactic acid bacteria. Food Research International 29(5-6), 555-562.

Chang, J.Y., Antonopoulos, D.A., Kalra, A., Tonelli, A., Khalife, W.T., Schmidt, T.M., and Young, V.B. (2008). Decreased diversity of the fecal Microbiome in recurrent Clostridium difficile-associated diarrhea. J. Infect. Dis. 197(3), 435-438.

Chapman, C.M.C., Gibson, G.R., and Rowland, I. (2012). In vitro evaluation of single- and multi-strain probiotics: Inter-species inhibition between probiotic strains, and inhibition of pathogens. Anaerobe 18(4), 405-413.

Chen, X., Katchar, K., Goldsmith, J.D., Nanthakumar, N., Cheknis, A., Gerding, D.N., and Kelly, C.P. (2008). A Mouse Model of Clostridium difficile—Associated Disease. Gastroenterology 135(6), 1984-1992.

Chow, J., Tang, H., and Mazmanian, S.K. (2011). Pathobionts of the Gastrointestinal Microbiota and Inflammatory Disease. Curr Opin Immunol 23(4), 473-480.

Claesson, M.J., Wang, Q., O'Sullivan, O., Greene-Diniz, R., Cole, J.R., Ross, R.P., and O'Toole, P.W. (2010). Comparison of two next-generation sequencing technologies for resolving highly complex microbiota composition using tandem variable 16S rRNA gene regions. Nucleic Acids Res 38(22), e200.

Clemente, J.C., Ursell, L.K., Parfrey, L.W., and Knight, R. (2012). The impact of the gut microbiota on human health: an integrative view. Cell 148(6), 1258-1270.

D'Souza, D.H., and Su, X. (2010). Efficacy of chemical treatments against murine norovirus, feline calicivirus, and MS2 bacteriophage. Foodborne Pathogens and Disease 7(3), 319-326.

David, L.A., Maurice, C.F., Carmody, R.N., Gootenberg, D.B., Button, J.E., Wolfe, B.E., Ling, A.V., Devlin, A.S., Varma, Y., Fischbach, M.A., et al. (2013). Diet rapidly and reproducibly alters the human gut microbiome. Nature advance online publication.

De Angelis, M., Piccolo, M., Vannini, L., Siragusa, S., De Giacomo, A., Serrazzanetti, D.I., Cristofori, F., Guerzoni, M.E., Gobbetti, M., and Francavilla, R. (2013). Fecal Microbiota and Metabolome of Children with Autism and Pervasive Developmental Disorder Not Otherwise Specified. PLoS ONE 8(10), e76993.

De Vos, W.M. (2013). Fame and future of faecal transplantations—developing next-generation therapies with synthetic microbiomes: Fame and future of faecal transplantations. Microbial Biotechnology 6(4), 316-325.

Defined Fecal Microbiota Transplantation for Clostridium Difficile Diarrhea. <http://clinicaltrials.gov/ct2/show/NCT01868373> Accessed Mar. 26, 2014.

Dezfulian, M. et al., "Selective Medium for Isolation of Clostridium botulinum from Human Feces," Journal of Clinical Microbiology, Mar. 1981, pp. 526-531, vol. 13, No. 3.

Derrien, M. (2004). Akkermansia muciniphila gen. nov., sp. nov., a human intestinal mucin-degrading bacterium. International Journal of Systematic and Evolutionary Microbiology 54(5), 1469-1476.

Dethlefsen, L., Huse, S., Sogin, M.L., and Relman, D.A. (2008). The Pervasive Effects of an Antibiotic on the Human Gut Microbiota, as Revealed by Deep 16S rRNA Sequencing. PLoS Biology 6(11), e280.

Detmer, A., and Glenting, J. (2006). Live bacterial vaccines—a review and identification of potential hazards. Microb Cell Fact 5, 23.

Dharmani, P., De Simone, C., and Chadee, K. (2013). The Probiotic Mixture VSL#3 Accelerates Gastric Ulcer Healing by Stimulating Vascular Endothelial Growth Factor. PLoS One 8(3), e58671.

Dietrich, G., Collioud, A., and Rothen, S.A. (2008). Developing and Manufacturing Attenuated Live Bacterial Vaccines. <http://www.biopharminternational.com/biopharm/Vaccine+Manufacturing+Articles/Developing-and-Manufacturing-Attenuated-Live-Bacte/ArticleStandard/Article/detail/557306> Accessed Mar. 25, 2014.

Dowell, V.R. et al., "Coproexamination for Botulinal Toxin and Clostridium botulinum," JAMA, Oct. 24, 1977, pp. 1829-1832, vol. 238, No. 7.

Dragon, D.C., and Rennie, R.P. (2001). Evaluation of spore extraction and purification methods for selective recovery of viable Bacillus anthracis spores. Lett. Appl. Microbiol. 33(2), 100-105.

Duc, L. (2003). Germination of the spore in the gastrointestinal tract provides a novel route for heterologous antigen delivery. Vaccine 21(27-30), 4215-4224.

Duc, L.H., Hong, H.A., Fairweather, N., Ricca, E., and Cutting, S.M. (2003). Bacterial Spores as Vaccine Vehicles. Infection and Immunity 71(5), 2810-2818.

Dumas, M.E. et al., (2006). Metabolic profiling reveals a contribution of gut microbiota to fatty liver phenotype in insulin-resistant mice, PNAS, Aug. 15, 2006, pp. 12511-12516, vol. 103, No. 33.

Dutta, S.K., Girotra, M., Garg, S., Dutta, A., Von Rosenvinge, E.C., Maddox, C., Song, Y., Bartlett, J.G., Vinayek, R., and Fricke, W.F. (2014). Efficacy of Combined Jejunal and Colonic Fecal Microbiota Transplantation for Recurrent Clostridium difficile Infection. Clinical Gastroenterology and Hepatology.

(56) References Cited

OTHER PUBLICATIONS

Edwards, A.D., and Slater, N.K.H. (2008). Formulation of a live bacterial vaccine for stable room temperature storage results in loss of acid, bile and bile salt resistance. Vaccine 26(45), 5675-5678.

Eiseman, B., Silen, W., Bascom, G.S., and Kauvar, A.J. (1958). Fecal enema as an adjunct in the treatment of pseudomembranous enterocolitis. Surgery 44(5), 854-859.

Elving, J., Emmoth, E., Albihn, A., Vinneras, B., and Ottoson, J. (2012). Composting for Avian Influenza Virus Elimination. Applied and Environmental Microbiology 78(9), 3280-3285.

Emanuelsson, F., Claesson, B.E.B., Ljungström, L., Tvede, M., and Ung, K.-A. (2014). Faecal microbiota transplantation and bacteriotherapy for recurrent Clostridium difficile infection: A retrospective evaluation of 31 patients. Scandinavian Journal of Infectious Diseases 46(2), 89-97.

Endt, K., Stecher, B., Chaffron, S., Slack, E., Tchitchek, N., Benecke, A., Van Maele, L., Sirard, J.-C., Mueller, A.J., Heikenwalder, M., et al. (2010). The Microbiota Mediates Pathogen Clearance from the Gut Lumen after Non-Typhoidal *Salmonella* Diarrhea. PLoS Pathog 6(9), e1001097.

European Extended Search Report, European Application No. 14768281.9, dated Jul. 18, 2016, 10 pages.

European Extended Search Report, European Application No. 14763266.5, dated Aug. 16, 2016, 7 pages.

Everard, A., Belzer, C., Geurts, L., Ouwerkerk, J.P., Druart, C., Bindels, L.B., Guiot, Y., Derrien, M., Muccioli, G.G., Delzenne, N.M., et al. (2013). Cross-talk between Akkermansia muciniphila and intestinal epithelium controls diet-induced obesity. Proceedings of the National Academy of Sciences 110(22), 9066-9071.

Fairhead, H., Setlow, B., Waites, W.M., and Setlow, P. (1994). Small, acid-soluble proteins bound to DNA protect *Bacillus subtilis* spores from being killed by freeze-drying. Applied and Environmental Microbiology 60(7), 2647-2649.

Faith, J.J., Ahern, P.P., Ridaura, V.K., Cheng, J., and Gordon, J.I. (2014). Identifying Gut Microbe—Host Phenotype Relationships Using Combinatorial Communities in Gnotobiotic Mice. Sci Transl Med 6(220), 220ra11-220ra11.

Fakhry, S., Sorrentini, I., Ricca, E., De Felice, M., and Baccigalupi, L. (2008). Characterization of spore forming Bacilli isolated from the human gastrointestinal tract. Journal of Applied Microbiology 105(6), 2178-2186.

Faust, et al., "Microbial Co-occurrence Relationships in the Human Microbiome," PLoS Computational Biology, Jul. 2012, e1002606, 17 pages, vol. 8, No. 7.

Fell Jr., N.F., Pellegrino, P.M., and Gillespie, J.B. (2001). Mitigating phosphate interference in bacterial endospore detection by Tb dipicolinate photoluminescence. Analytica Chimica Acta 426(1), 43-50.

Fichtel, J., Köster, J., Rullkötter, J., and Sass, H. (2007). Spore dipicolinic acid contents used for estimating the number of endospores in sediments. FEMS Microbiology Ecology 61(3), 522-532.

Fischbach, M.A., Bluestone, J.A., and Lim, W.A. (2013). Cell-Based Therapeutics: The Next Pillar of Medicine. Sci Transl Med 5(179), 179ps7.

Fonseca, F., Béal, C., and Corrieu, G. (2001). Operating Conditions That Affect the Resistance of Lactic Acid Bacteria to Freezing and Frozen Storage. Cryobiology 43(3), 189-198.

Franz, C.M.A.P., Huch, M., Abriouel, H., Holzapfel, W., and Gálvez, A. (2011). Enterococci as probiotics and their implications in food safety. International Journal of Food Microbiology 151(2), 125-140.

Friedman-Moraco, R.J., Mehta, A.K., Lyon, G.M., and Kraft, C.S. (2014). Fecal Microbiota Transplantation for Refractory Clostridium difficile Colitis in Solid Organ Transplant Recipients: Fecal Microbiota Transplantation in Solid Organ Transplant Recipients. American Journal of Transplantation 14(2), 477-480.

Fuentes, S., Van Nood, E., Tims, S., Heikamp-De Jong, I., Ter Braak, C.J., Keller, J.J., Zoetendal, E.G., and De Vos, W.M. (2014). Reset of a critically disturbed microbial ecosystem: faecal transplant in recurrent Clostridium difficile infection. The ISME Journal.

GenBank HQ819637, "Uncultured Organism Clone ELU0180-T56-S-NIPCRAMgANa_000311 Small Subunit Ribosomal RNA Gene, Partial Sequence," Jul. 30, 2012,1 page, [Online] [Retrieved on Aug. 21, 2014] Retrieved from the Internet<URL:http://www.ncbi.nlm.nih.gov/nuccore/HQ819637>.

Gevers, D., Kugathasan, S., Denson, L.A., Vázquez-Baeza, Y., Van Treuren, W., Ren, B., Schwager, E., Knights, D., Song, S.J., Yassour, M., et al. (2014). The Treatment-Naive Microbiome in New-Onset Crohn's Disease. Cell Host & Microbe 15(3), 382-392.

Gilligan, P.H. (2013). Identification of Pathogens by Classical Clinical Tests. In the Prokaryotes, E. Rosenberg, E.F. DeLong, S. Lory, E. Stackebrandt, and F. Thompson, eds. (Springer Berlin Heidelberg), pp. 57-89.

Goodman, A.L., Kallstrom, G., Faith, J.J., Reyes, A., Moore, A., Dantas, G., and Gordon, J.I. (2011). From the Cover: Extensive personal human gut microbiota culture collections characterized and manipulated in gnotobiotic mice. Proceedings of the National Academy of Sciences 108(15), 6252-6257.

Goodman, N.S., Gottfried, R.J., and Rogoff, M.H. (1967). Biphasic system for separation of spores and crystals of Bacillus thuringiensis. Journal of Bacteriology 94(2), 485.

Gough, E. et al., "Systematic Review of Intestinal Microbiota Transplantation (Fecal Bacteriotherapy) for Recurrent Clostridium Dfficile Infection," Clin. Infect. Dis., Nov. 15, 2011, pp. 994-1002, vol. 53, No. 10.

Gould, G.W., and Sale, A.J. (1970). Initiation of germination of bacterial spores by hydrostatic pressure. J. Gen. Microbiol. 60(3), 335-346.

Grabow, W.O., Clay, C.G., Dhaliwal, W., Vrey, M.A., and Müller, E.E. (1999). Elimination of viruses, phages, bacteria and Cryptosporidium by a new generation Aquaguard point-of-use water treatment unit. Zentralbl Hyg Umweltmed 202(5), 399-410.

Greenway, F., Wang, S., and Heiman, M. (2014). A novel cobiotic containing a prebiotic and an antioxidant augments the glucose control and gastrointestinal tolerability of metformin: a case report. Beneficial Microbes 5(1), 29-32.

Grehan, M.J., Borody, T.J., Leis, S.M., Campbell, J., Mitchell, H., and Wettstein, A. (2010). Durable alteration of the colonic microbiota by the administration of donor fecal flora. J. Clin. Gastroenterol. 44(8), 551-561.

Grimoud, J. et al., "In Vitro Screening of Probiotic Lactic Acid Bacteria and Prebiotic Glucooligosaccharides to Select Effective Synbiotics," Anaerobe, Clinical Microbiology, Oct. 2010, pp. 493-500, vol. 16, No. 5.

Gupta, R.K. et al., "Differentiation Between Heat Resistance and Octyl Alcohol Resistance of the Cells of Bacillus Cereus T.," Biochemical and Biophysical Research Communications, 1970, pp. 23-30, vol. 38, No. 1.

Halmann, M. et al., "Stages in Germination of Spores of Bacillus Lichenformis," J. Bacteriol., 1962, pp. 1187-1193, vol. 84.

Hamilton, M.J., Weingarden, A.R., Sadowsky, M.J., and Khoruts, A. (2012). Standardized frozen preparation for transplantation of fecal microbiota for recurrent Clostridium difficile infection. Am. J. Gastroenterol. 107(5), 761-767.

Hamilton, M.J., Weingarden, A.R., Unno, T., Khoruts, A., and Sadowsky, M.J. (2013). High-throughput DNA sequence analysis reveals stable engraftment of gut microbiota following transplantation of previously frozen fecal bacteria. Gut Microbes 4(2), 125-135.

Harmsen, H. J. M., Gibson, G. R., Elfferich, P., Raangs, G. C., Wildeboer-Veloo, A. C. M., Argaiz, A., Roberfroid, M. B., and Welling, G. W. (2000). Comparison of viable cell counts and fluorescence in situ hybridization using specific rRNA-based probes for the quantification of human fecal bacteria. FEMS Microbiology Letters 183(1), 125-129.

Harrison, F., "Bacterial Cooperation in the Wild and in the Clinic: Are Pathogen Social Behaviours Relevant Outside the Laboratory?" Bioessays, Dec. 27, 2012, pp. 108-112, vol. 35, No. 2.

(56) References Cited

OTHER PUBLICATIONS

Hasan, J.A., Japal, K.M., Christensen, E.R., and Samalot-Freire, L.C. (2011). In vitro production of Clostridium difficile spores for use in the efficacy evaluation of disinfectants: a precollaborative investigation. J AOAC Int 94(1), 259-272.

Hayashi, Y. et al., "Western Blot (Immunoblot) Assay of Small Round-Structured Virus Associated with an Acute Gastroenteritis Outbreak in Tokyo," Journal of Clinical Microbiology, Aug. 1989, pp. 1728-1733, vol. 27.

Hell, M., Bernhofer, C., Stalzer, P., Kern, J.M., and Claassen, E. (2013). Probiotics in Clostridium difficile infection: reviewing the need for a multistrain probiotic. Beneficial Microbes 4(1), 39-51.

Hemmerling, A., Harrison, W., Schroeder, A., Park, J., Korn, A., Shiboski, S., Foster-Rosales, A., and Cohen, C.R. (2010). Phase 2a Study Assessing Colonization Efficiency, Safety, and Acceptability of Lactobacillus crispatus CTV-05 in Women With Bacterial Vaginosis: Sexually Transmitted Diseases 37(12), 745-750.

Herron, P.R., and Wellington, E.M.H. (1990). New Method for Extraction of Streptomycete Spores from Soil and Application to the Study of Lysogeny in Sterile Amended and Nonsterile Soil. Appl Environ Microbiol 56(5), 1406-1412.

Hewitt, J., Rivera-Aban, M., and Greening, G.E. (2009). Evaluation of murine norovirus as a surrogate for human norovirus and hepatitis A virus in heat inactivation studies. Journal of Applied Microbiology 107(1), 65-71.

Hindle, A.A., and Hall, E.A.H. (1999). Dipicolinic acid (DPA) assay revisited and appraised for spore detection. The Analyst 124(11), 1599-1604.

Hirsch, E.B., and Tam, V.H. (2010). Detection and treatment options for Klebsiella pneumoniae carbapenemases (KPCs): an emerging cause of multidrug-resistant infection. J. Antimicrob. Chemother. 65(6), 1119-1125.

Hofsten, B.V. (1966). Partition of *Escherichia coli* in an aqueous polymer two-phase system. Experimental Cell Research 41(1), 117-123.

Holmes, E., Kinross, J., Gibson, G.R., Burcelin, R., Jia, W., Pettersson, S., and Nicholson, J.K. (2012). Therapeutic Modulation of Microbiota-Host Metabolic Interactions. Science Translational Medicine 4(137), 137rv6-137rv6.

Hoppe, B., Groothoff, J.W., Hulton, S.-A., Cochat, P., Niaudet, P., Kemper, M.J., Deschênes, G., Unwin, R., and Milliner, D. (2011). Efficacy and safety of Oxalobacter formigenes to reduce urinary oxalate in primary hyperoxaluria. Nephrol. Dial. Transplant. 26(11), 3609-3615.

Hoyles, L., Honda, H., Logan, N.A., Halket, G., La Ragione, R.M., and McCartney, A.L. (2012). Recognition of greater diversity of *Bacillus* species and related bacteria in human faeces. Res. Microbiol. 163(1), 3-13.

Hurst, C.J., and Gerba, C.P. (1989). Fate of viruses during wastewater sludge treatment processes. Critical Reviews in Environmental Control 18(4), 317-343.

Iizuka, M. et al., "Elemental Diet Modulates the Growth of Clostridium difficile in the Gut Flora," Aliment Pharmacol. Ther., Jul. 2004, pp. 151-157, vol. 20, Suppl. 1.

Itoh, K., and Mitsuoka, T. (1985). Characterization of clostridia isolated from faeces of limited flora mice and their effect on caecal size when associated with germ-free mice. Laboratory Animals 19(2), 111-118.

Itoh, K., Lee, W.K., Kawamura, H., Mitsuoka, T., and Magaribuchi, T. (1987). Intestinal bacteria antagonistic to Clostridium difficile in mice. Lab Anim 21(1), 20-25.

Itoh, K., Urano, T., and Mitsuoka, T. (1986). Colonization resistance against Pseudomonas aeruginosa in gnotobiotic mice. Lab Anim 20(3), 197-201.

Jalanka-Tuovinen, J., Salojarvi, J., Salonen, A., Immonen, O., Garsed, K., Kelly, F.M., Zaitoun, A., Palva, A., Spiller, R.C., and De Vos, W.M. (2013). Faecal microbiota composition and host-microbe cross-talk following gastroenteritis and in postinfectious irritable bowel syndrome. Gut 0, 1-9.

Jeffs, L.B., and Khachatourians, G.G. (1997). Estimation of spore hydrophobicity for members of the genera Beauveria, Metarhizium, and Tolypocladium by salt-mediated aggregation and sedimentation. Canadian Journal of Microbiology 43(1), 23-28.

Jensen, N.S., and Canale-Parola, E. (1986). *Bacteroides pectinophilus* sp. nov. and *Bacteroides galacturonicus* sp. nov.: two pectinolytic bacteria from the human intestinal tract. Appl. Environ. Microbiol. 52(4), 880-887.

Johnston, R. et al., "Method to Facilitate the Isolation of Clostridium botulinum Type E," J. Bacteriol., 1964, pp. 1521-1522, vol. 88.

Jones, M.L., Martoni, C.J., and Prakash, S. (2012a). Cholesterol lowering and inhibition of sterol absorption by Lactobacillus reuteri NCIMB 30242: a randomized controlled trial. Eur J Clin Nutr 66(11), 1234-1241.
Jones, M.L., Martoni, C.J., Parent, M., and Prakash, S. (2012b). Cholesterol-lowering efficacy of a microencapsulated bile salt hydrolase-active Lactobacillus reuteri NCIMB 30242 yoghurt formulation in hypercholesterolaemic adults. British Journal of Nutrition 107(10), 1505-1513.
Joosten, H. et al., "*Salmonelle* Detection in Probiotic Products," International Journal of Food Microbiology, Jul. 2006, pp. 104-107, vol. 110, No. 1.
Jorgensen, J.H., and Ferraro, M.J. (2009). Antimicrobial Susceptibility Testing: A Review of General Principles and Contemporary Practices. Clin Infect Dis., Medical Microbiology, 49(11), 1749-1755.
Jorup-Rönström, C., Håkanson, A., Sandell, S., Edvinsson, O., Midtvedt, T., Persson, A.-K., and Norin, E. (2012). Fecal transplant against relapsing Clostridium difficile-associated diarrhea in 32 patients. Scand. J. Gastroenterol. 47(5), 548-552.
Jousimies-Somer, H., Summanen, P., Citron, D.M., Baron, E.J., Wexler, H.M., and Finegold, S.M. (2002). Wadsworth-KLT Anaerobic Bacteriology Manual, 6th edition (California: Star), pp. 55-74, 81-132, 165-185.
Kailasapathy, K. (2002). Microencapsulation of probiotic bacteria: technology and potential applications. Curr Issues Intest Microbiol 3(2), 39-48.
Kamiya, S., Yamakawa, K., Ogura, H., and Nakamura, S. (1989). Recovery of spores of Clostridium difficile altered by heat or alkali. J Med Microbiol 28(3), 217-221.
Kanamoto, T. et al., "Genetic Heterogeneities and Phenotypic Characteristics of Strains of the Genus *Abiotrophia* and Proposal of *Abiotrophia* para-adiacens sp. nov.," Journal of Clinical Microbiology, Feb. 2000, pp. 492-498, vol. 38, No. 2; *Abiotropia* para-adjacens gene for 16S rRNA, partial sequence, strain: Nucleotide: NCBI: GenBank: AB022027.1, last accessed Mar. 12, 2014, p. 8.
Kanehisa Laboratories. Kegg: Kyoto encyclopedia of genes and genomes. <http://www.genome.jp/kegg/> Accessed Mar. 27, 2014.
Karasawa, T. et al., "A Defined Growth Medium for Clostridium difficile," Microbiology, Feb. 1995, pp. 371-375, vol. 151, No. 2.
Kazamias, M. et al., "Enhanced Fermentation of Mannitol and Release of Cytotoxin by Clostridium difficile in Alkaline Culture Media," Applied and Environmental Microbiology, Jun. 1995, pp. 2425-2427, vol. 61, No. 6.
Kelly, D., Campbell, J.I., King, T.P., Grant, G., Jansson, E.A., Coutts, A.G.P., Pettersson, S., and Conway, S. (2003). Commensal anaerobic gut bacteria attenuate inflammation by regulating nuclear-cytoplasmic shuttling of PPAR-γ and RelA. Nature Immunology 5(1), 104-112.
Khoruts, A. (2013). How Does Fecal Microbiota Transplantation Treat Clostridium difficile Infection? <https://www.genome.gov/Multimedia/Slides/HumanMicrobiomeScience2013/39_Khoruts.pdf> Accessed Mar. 21, 2014.
Khoruts, A., and Sadowsky, M.J. (2011). Therapeutic transplantation of the distal gut microbiota. Mucosal Immunol 4(1), 4-7.
Khoruts, A., Dicksved, J., Jansson, J.K., and Sadowsky, M.J. (2010). Changes in the composition of the human fecal microbiome after bacteriotherapy for recurrent Clostridium difficile-associated diarrhea. J. Clin. Gastroenterol. 44(5), 354-360.

(56) References Cited

OTHER PUBLICATIONS

Kim, B., Kim, N.J., Kim, M., Kim, Y.S., Woo, J., and Ryu, J. (2003). Bacteraemia Due to Tribe Proteeae: A Review of 132 Cases During a Decade (1991-2000). Scandinavian Journal of Infectious Diseases 35(2), 98-103.

Klayraung, S., Viernstein, H., and Okonogi, S. (2009). Development of tablets containing probiotics: Effects of formulation and processing parameters on bacterial viability. International Journal of Pharmaceutics 370(1-2), 54-60.

Kollmann, M. et al., Design Principles of a Bacterial Signalling Network, Nature, Nov. 24, 2005, pp. 504-507, vol. 438, No. 7067.

Kong, Q., He, G.-Q., Jia, J.-L., Zhu, Q.-L., and Ruan, H. (2011). Oral Administration of Clostridium butyricum for Modulating Gastrointestinal Microflora in Mice. Curr Microbiol 62(2), 512-517.

Konstantinidis, K.T., Ramette, A., and Tiedje, J.M. (2006). The bacterial species definition in the genomic era. Philos Trans R Soc Lond B Biol Sci 361(1475), 1929-1940.

Koonin, E.V. (2002). Chapter 22 the clusters of orthologous groups (COGS) database: Phylogenetic classification of proteins from complete genomes. <http://www.ncbi.nlm.nih.gov/books/NBK21090/pdf/ch22.pdf> Accessed Mar 27, 2014.

Koransky, J.R., Allen, S.D., and Dowell, V.R., Jr (1978). Use of ethanol for selective isolation of sporeforming microorganisms. Appl. Environ. Microbiol. 35(4), 762-765.

Koransky, J.R. et al., "Use of Ethanol for Selective Isolation of Sporeforming Microorganisms," Applied and Environmental Microbiology, Apr. 1978, pp. 762-765, vol. 35.

Kort, R., O'Brien, A.C., Stokkum, I.H.M. Van, Oomes, S.J.C.M., Crielaard, W., Hellingwerf, K.J., and Brul, S. (2005). Assessment of Heat Resistance of Bacterial Spores from Food Product Isolates by Fluorescence Monitoring of Dipicolinic Acid Release. Appl. Environ. Microbiol. 71(7), 3556-3564.

Kucerova, Z., Moura, H., Leitch, G.J., Sriram, R., Bern, C., Kawai, V., Vargas, D., Gilman, R.H., Ticona, E., and Vivar, A. (2004). Purification of Enterocytozoon bieneusi spores from stool specimens by gradient and cell sorting techniques. Journal of Clinical Microbiology 42(7), 3256-3261.

Kumar, M. et al., "Cholesterol-Lowering Probiotics as Potential Biotherapeutics for Metabolic Diseases," Experimental Diabetes Research, 2012, Article ID 902917, 14 pages, vol. 2012.

Kump, P.K., Gröchenig, H.-P., Lackner, S., Trajanoski, S., Reicht, G., Hoffmann, K.M., Deutschmann, A., Wenzl, H.H., Petritsch, W., Krejs, G.J., et al. (2013). Alteration of intestinal dysbiosis by fecal microbiota transplantation does not induce remission in patients with chronic active ulcerative colitis. Inflamm. Bowel Dis. 19(10), 2155-2165.

Kunde, S., Pham, A., Bonczyk, S., Crumb, T., Duba, M., Conrad, H., Jr, Cloney, D., and Kugathasan, S. (2013). Safety, tolerability, and clinical response after fecal transplantation in children and young adults with ulcerative colitis. J. Pediatr. Gastroenterol. Nutr. 56(6), 597-601.

Landy, J., Al-Hassi, H.O., Mclaughlin, S.D., Walker, A.W., Ciclitira, P.J., Nicholls, R.J., Clark, S.K., and Hart, A.L. (2011). Review article: faecal transplantation therapy for gastrointestinal disease. Alimentary Pharmacology & Therapeutics 34(4), 409-415.

Lawley, T.D., Clare, S., Walker, A.W., Stares, M.D., Connor, T.R., Raisen, C., Goulding, D., Rad, R., Schreiber, F., Brandt, C., et al. (2012). Targeted Restoration of the Intestinal Microbiota with a Simple, Defined Bacteriotherapy Resolves Relapsing Clostridium difficile Disease in Mice. PLoS Pathog 8(10), e1002995.

Lawson, P.A., Song, Y., Liu, C., Molitoris, D.R., Vaisanen, M.-L., Collins, M.D., and Finegold, S.M. (2004). *Anaerotruncus colihominis* gen. nov., sp. nov., from human faeces. Int J Syst Evol Microbiol 54(2), 413-417.

Lee, I.-K., and Liu, J.-W. (2006). Clinical characteristics and risk factors for mortality in Morganella morganii bacteremia. J Microbiol Immunol Infect 39(4), 328-334.

Lee, J.S., Cha, D.S., and Park, H.J. (2004). Survival of Freeze-Dried Lactobacillus bulgaricus KFRI 673 in Chitosan-Coated Calcium Alginate Microparticles. J. Agric. Food Chem. 52(24), 7300-7305.

Lee, M., Hesek, D., Shah, I.M., Oliver, A.G., Dworkin, J., and Mobashery, S. (2010). Synthetic peptidoglycan motifs for germination of bacterial spores. Chembiochem 11(18), 2525-2529.

Lehar, J. (2007). Chemical combination effects predict connectivity in biological systems, Molecular Systems Biology, pp. 1-14, vol. 3, Article No. 80.

Lemon, K.P., Armitage, G.C., Relman, D.A., and Fischbach, M.A. (2012) Microbiota-Targeted Therapies: An Ecological Perspective. Science Translational Medicine 4(137), 137rv5-137rv5.

Leslie, S.B., Israeli, E., Lighthart, B., Crowe, J.H., and Crowe, L.M. (1995). Trehalose and sucrose protect both membranes and proteins in intact bacteria during drying. Applied and Environmental Microbiology 61(10), 3592-3597.

Liggins, M., Ramirez, N., Magnuson, N., and Abel-Santos, E. (2011). Progesterone analogs influence germination of Clostridium sordellii and Clostridium difficile spores in vitro. J. Bacteriol. 193(11), 2776-2783.

Lindsay, J.A., Beaman, T.C., and Gerhardt, P. (1985). Protoplast water content of bacterial spores determined by buoyant density sedimentation. J. Bacteriol. 163(2), 735-737.

Liu, K., Linder, C.R., and Warnow, T. (2011). RAxML and FastTree: Comparing Two Methods for Large-Scale Maximum Likelihood Phylogeny Estimation. PLoS ONE 6(11), e27731.

Livingston, S.J., Kominos, S.D., and Yee, R.B. (1978). New medium for selection and presumptive identification of the Bacteroides fragilis group. J. Clin. Microbiol. 7(5), 448-453.

Logan, N.A., "Bacillus and Relatives in Foodborne Illness," Journal of Applied Microbiology, Mar. 20, 2012, pp. 417-429, vol. 112, No. 3.

Lopetuso, L.R., Scaldaferri, F., Petito, V., and Gasbarrini, A. (2013). Commensal Clostridia: leading players in the maintenance of gut homeostasis. Gut Pathogens 5(1), 23.

Lodish, H. et al., "Viruses: Structure, Function, and Uses," Molecular Cell Biology, $4^{th}$ Edition, 2000, pp. 1-12.

Lozupone, C., Faust, K., Raes, J., Faith, J.J., Frank, D.N., Zaneveld, J., Gordon, J.I., and Knight, R. (2012). Identifying genomic and metabolic features that can underlie early successional and opportunistic lifestyles of human gut symbionts. Genome Res 22(10), 1974-1984.

Malik, K.A. (1988). A new freeze-drying method for the preservation of nitrogen-fixing and other fragile bacteria. Journal of Microbiological Methods 8(5), 259-271.

Manichanh, C. (2006). Reduced diversity of faecal microbiota in Crohn's disease revealed by a metagenomic approach. Gut 55(2), 205-211.

Matsuda, K. et al., "Sensitive Quantitative Detection of Commensal Bacteria by rRNA-Targeted Reverse Transcription-PCR," Applied and Environmental Microbiology, Jan. 2007, pp. 32-39, vol. 73, No. 1.

Mbithi, J.N., Springthorpe, V.S., and Sattar, S.A. (1990). Chemical disinfection of hepatitis A virus on environmental surfaces. Applied and Environmental Microbiology 56(11), 3601-3604.

McFarland, L.V., "Use of Probiotics to Correct Dysbiosis of Normal Microbiota Following Disease or Disruptive Events: A Systematic Review," BMJ Open, 2014, pp. 1-18, vol. 4.

McGuire, G., Denham, M.C., and Balding, D.J. (2001). Models of Sequence Evolution for DNA Sequences Containing Gaps. Mol Biol Evol 18(4), 481-490.

McNulty, N.P., Yatsunenko, T., Hsiao, A., Faith, J.J., Muegge, B.D., Goodman, A.L., Henrissat, B., Oozeer, R., Cools-Portier, S., Gobert, G., et al. (2011). The impact of a consortium of fermented milk strains on the gut microbiome of gnotobiotic mice and monozygotic twins. Sci Transl Med 3(106), 106ra106.

Mevissen-Verhage, E.A., Marcelis, J.H., Vos, M.N. De, Amerongen, W.C.H., and Verhoef, J. (1987). *Bifidobacterium, Bacteroides,* and *Clostridium* spp. In fecal samples from breast-fed and bottle-fed infants with and without iron supplement. J. Clin. Microbiol. 25(2), 285-289.

Miller, R.S., and Hoskins, L.C. (1981). Mucin degradation in human colon ecosystems. Fecal population densities of mucin-degrading bacteria estimated by a "most probable number" method. Gastroenterology 81(4), 759-765.

(56) References Cited

OTHER PUBLICATIONS

Mireau, I. et al., "Industrial-Scale Production and Purification of a Heterologous Protein in Lactococcus lactis Using the Nisin-Controlled Gene Expression System NICE: The Case of Lysostaphin," Microbial Cell Factories, May 27, 2005, pp. 1-9, vol. 4, 15.
Miyamoto-Shinohara, Y., Sukenobe, J., Imaizumi, T., Nakahara, T., and Others (2008). Survival of freeze-dried bacteria. The Journal of General and Applied Microbiology 54(1), 9.
Momose, Y. et al., "16S rRNA Gene Sequence-Based Analysis of Clostridia Related to Conversion of Germfree Mice to the Normal State," Journal of Applied Microbiology, 2009, pp. 2088-2097, vol. 107.
Morgan, C.A., Herman, N., White, P.A., and Vesey, G. (2006). Preservation of micro-organisms by drying; A review. Journal of Microbiological Methods 66(2), 183-193.
Murri, M., Leiva, I., Gomez-Zumaquero, J.M., Tinahones, F.J., Cardona, F., Soriguer, F., and Queipo-Ortuño, M.I. (2013). Gut microbiota in children with type 1 diabetes differs from that in healthy children: a case-control study. BMC Med 11(1), 1-12.
Myllyluoma, E. et al., "Effects of Multispecies Probiotic Combination on Helicobacter pylori Infection in Vitro," Clinical and Vaccine Immunology, Sep. 2008, pp. 1472-1482, vol. 15, No. 9.
Naaber P et al "Inhibition of Clostridium difficile strains by intestinal *Lactobacillus* species" Journal of Medical Microbiology, 2004, pp. 551-554, vol. 53.
New Zealand First Examination Report, New Zealand Application No. 709392, dated Oct. 5, 2015, 7 pages.
New Zealand First Examination Report, New Zealand Application No. 711771, dated Nov. 23, 2015, 6 pages.
New Zealand First Examination Report, New Zealand Application No. 711773, dated Nov. 24, 2015, 6 pages.
New Zealand Second Examination Report, New Zealand Application No. 709392, dated Jun. 9, 2016, 7 pages.
Nicholson, W.L., and Law, J.F. (1999). Method for purification of bacterial endospores from soils: UV resistance of natural Sonoran desert soil populations of< i> *Bacillus*</i> spp. with reference to< i> *B. subtilis*</i> strain 168. Journal of Microbiological Methods 35(1), 13-21.
NIH human microbiome project. <http://www.hmpdacc.org/> Accessed Mar. 27, 2014.
Nishio, J., Atarashi, K., Tanoue, T., Baba, M., Negishi, H., Yanai, H., Honda, K., Benoist, C., Mathis, D., and Taniguchi, T. (2013). Impact of TCR repetoire on intestinal homeostasis (Taos, NM).
Nitert, M.D., Barrett, H.L., Foxcroft, K., Tremellen, A., Wilkinson, S., Lingwood, B., Tobin, J.M., McSweeney, C., O'Rourke, P., Mcintyre, H.D., et al. (2013). SPRING: an RCT study of probiotics in the prevention of gestational diabetes mellitus in overweight and obese women. BMC Pregnancy and Childbirth 13(1), 50.
Noack, J., Kleessen, B., Proll, J., Dongowski, G., and Blaut, M. (1998). Dietary guar gum and pectin stimulate intestinal microbial polyamine synthesis in rats. J. Nutr. 128(8), 1385-1391.
Nyangale, et al., "Gut Microbial Activity, Implications for Health and Disease: the Potential Role of Metabolite Analysis," J. Proteome Res., 2012, pp. 5573-5585. vol. 11, No. 12.
O'Hara, C.M., Brenner, F.W., and Miller, J.M. (2000). Classification, identification, and clinical significance of Proteus, Providencia, and Morganella. Clin. Microbiol. Rev. 13(4), 534-546.
Okada, Y., Setoyama, H., Matsumoto, S., Imaoka, A., Nanno, M., Kawaguchi, M., and Umesaki, Y. (1994). Effects of fecal microorganisms and their chloroform-resistant variants derived from mice, rats, and humans on immunological and physiological characteristics of the intestines of ex-germfree mice. Infect. Immun. 62(12), 5442-5446.
Olle, B. (2013). Medicines from microbiota. Nat. Biotechnol. 31(4), 309-315.
OpenBiome. Quality metrics. <http://static.squarespace.com/static/50e0c29ae4b0a05702af7e6a/t/52e19689e4b0b28f802c9b4e/1390517129976/OpenBiome%20Quality%20Metrics.pdf> Accessed Mar. 21, 2014.

Owens, C., Broussard, E., and Suravvicz, C. (2013). Fecal microbiota transplantation and donor standardization. Trends in Microbiology 21(9), 443-445.
Paine, R.T. (1969). A note on trophic complexity and community stability. American Naturalist 103(929), 91-93.
Palmfeldt, J., and Hahn-Hägerdal, B. (2000). Influence of culture pH on survival of< i> Lactobacillus reuteri</i> subjected to freeze-drying. International Journal of Food Microbiology 55(1), 235-238.
Pamer, E.G. (2014). Fecal microbiota transplantation: effectiveness, complexities, and lingering concerns. Mucosal Immunology 7(2), 210-214.
Paredes-Sabja, D., Udompijitkul, P., and Sarker, M.R. (2009). Inorganic phosphate and sodium ions are cogerminants for spores of Clostridium perfringens type A food poisoning-related isolates. Appl. Environ. Microbiol. 75(19), 6299-6305.
Path Vaccine and Pharmaceutical Technologies Group. Summary of stability data for investigational formulations of vaccines. <http://www.path.org/publications/files/TS_vaccine_stability_table_invest.pdf> Accessed Mar. 21, 2014.
PCT International Search Report and Written Opinion, PCT Application No. PCT/US14/14744, dated May 21, 2014, 36 pages.
PCT International Search Report and Written Opinion, PCT Application No. PCT/US14/14747, dated Jun. 13, 2014, 27 pages.
PCT International Search Report and Written Opinion, PCT Application No. PCT/US14/14738, dated Jul. 30, 2014, 32 pages.
PCT International Search Report and Written Opinion, PCT Application No. PCT/US14/14745, dated Jul. 30, 2014, 31 pages.
PCT Invitation to Pay Additional Fees, PCT Application No. PCT/US14/14745, dated May 16, 2014, 2 pages.
PCT International Search Report and Written Opinion, PCT Application No. PCT/US13/71758, dated May 5, 2014, 45 pages.
PCT Invitation to Pay Additional Fees, PCT Application No. PCT/US14/70684, dated Mar. 24, 2015, 2 pages.
PCT International Search Report and Written Opinon, PCT Application No. PCT/US2014/067491, dated Apr. 2, 2015, 14 pages.
PCT International Search Report and Written Opinion, PCT Application No. PCT/US14/70684, dated Jun. 10, 2015, 24 pages.
PCT Invitation to Pay Additional Fees, PCT Application No. PCT/US13/71758, dated Feb. 25, 2014, 4 pages.
PCT Invitation to Pay Additional Fees, PCT Application No. PCT/US2014/014738, dated May 16, 2014, 2 pages.
PCT International Search Report and Written Opinion, PCT Application No. PCT/US2014/030817, dated Dec. 5, 2014, 16 pages.
PCT Invitation to Pay Additional Fees, PCT Application No. PCT/US2014/030817, dated Sep. 8, 2014, 5 pages.
PCT International Search Report and Written Opinion, PCT Application No. PCT/US2014/029539, dated Oct. 10, 2014, 17 pages.
PCT Invitation to Pay Additional Fees, PCT Application No. PCT/US14/29539, dated Jul. 31, 2014, 3 pages.
Peck, M.W. et al., "Development and Application of a New Method for Specific and Sensitive Enumeration of Spores of Nonproteolytic Clostridium Botulinum Types B, E and F in Foods and Food Materials," Applied and Environmental Microbiology, Oct. 2010, pp. 6607-6614, vol. 76, No. 19.
Pehkonen, K.S., Roos, Y.H., Miao, S., Ross, R.P., and Stanton, C. (2008). State transitions and physicochemical aspects of cryoprotection and stabilization in freeze-drying of Lactobacillus rhamnosus GG (LGG). Journal of Applied Microbiology 104(6), 1732-1743.
Peighambardoust, S.H., Golshan Tafti, A., and Hesari, J. (2011). Application of spray drying for preservation of lactic acid starter cultures: a review. Trends in Food Science & Technology 22(5), 215-224.
Pellegrino, P.M., Fell Jr., N.F., and Gillespie, J.B. (2002). Enhanced spore detection using dipicolinate extraction techniques. Analytica Chimica Acta 455(2), 167-177.
Perez, F., Pultz, M.J., Endimiani, A., Bonomo, R.A., and Donskey, C.J. (2011). Effect of antibiotic treatment on establishment and elimination of intestinal colonization by KPC-producing Klebsiella pneumoniae in mice. Antimicrob. Agents Chemother. 55(6), 2585-2589.
Perez, J., Springthorpe, V.S., and Sattar, S.A. (2011). Clospore: a liquid medium for producing high titers of semi-purified spores of Clostridium difficile. J AOAC Int 94(2), 618-626.

(56) References Cited

OTHER PUBLICATIONS

Peterson, D.A. et al., "Metagenomic Approaches for Defining the Pathogenesis of Inflammatory Bowel Diseases," Cell Host Microbe, Jun. 2008, pp. 417-427, vol. 3, No. 6.
Petrof, E.O., Claud, E.C., Gloor, G.B., and Allen-Vercoe, E. (2013a). Microbial ecosystems therapeutics: a new paradigm in medicine? Beneficial Microbes 4(1), 53-65.
Petrof, E.O., Gloor, G.B., Vanner, S.J., Weese, S.J., Carter, D., Daigneault, M.C., Brown, E.M., Schroeter, K., and Allen-Vercoe, E. (2013b). Stool substitute transplant therapy for the eradication of Clostridium difficile infection: "RePOOPulating" the gut, Microbiome, Jan. 9, 2013, p. 3, vol. 1, No. 1.
Petrof, E.O. et al., "Stool Substitute Transplant Therapy for the Eradication of Clostridium difficile Infection: RePOOPulating'" The Gut Microbiome, Jan. 9, 2013, pp. 1-12, vol. 1, No. 3.
Picot, A., and Lacroix, C. (2004). Encapsulation of bifidobacteria in whey protein-based microcapsules and survival in simulated gastrointestinal conditions and in yoghurt. International Dairy Journal 14(6), 505-515.
Pinn, D. et al. (2013). Follow-up Study of Fecal Microbiota Transplantation (FMT) for the Treatment of Refractory Irritable Bowel Syndrome (IBS). Abstract ACG 2013.
Postgate, J.R., and Hunter, J.R. (1961). On the Survival of Frozen Bacteria. J Gen Microbiol 26(3), 367-378.
"Potentials of Probiotics in Pig Nutrition," AllAboutFeed News, Jan. 31, 2007,6 pages.
Prilassnig, M. et al., "Are Probiotics Detectable in Human Feces After Oral Uptake by Healthy Volunteers?" The Middle European Journal of Medicine, Aug. 2007, pp. 456-462, vol. 119, Nos. 15-16.
Pultz, N.J., Hoyen, C.K., and Donskey, C.J. (2004). Inhibition of methicillin-resistant *Staphylococcus aureus* by an in vitro continuous-flow culture containing human stool microflora. FEMS Microbiology Letters 241(2), 201-205.
Queenan, A.M., and Bush, K. (2007). Carbapenemases: The Versatile β-Lactamases. Clin. Microbiol. Rev. 20(3), 440-458.
Quigley, E.M.M. et al., "Small Intestinal Bacterial Overgrowth: Roles of Antibiotics, Prebiotics and Probiotics," Gastroenterology, Feb. 2006, pp. 78-90, vol. 130.
Raibaud, P., Ducluzeau, R., Dubos, F., Hudault, S., Bewa, H., and Muller, M.C. (1980). Implantation of bacteria from the digestive tract of man and various animals into gnotobiotic mice. Am J Clin Nutr 33(11), 2440-2447.
Ramirez, N., and Abel-Santos, E. (2010). Requirements for germination of Clostridium sordellii spores in vitro. J. Bacteriol. 192(2), 418-425.
Rao, A.V., Shiwnarain, N., and Maharaj, I. (1989). Survival of Microencapsulated Bifidobacterium pseudolongum in Simulated Gastric and Intestinal Juices. Canadian Institute of Food Science and Technology Journal 22(4), 345-349.
Reeves, A.E., Koenigsknecht, M.J., Bergin, I.L., and Young, V.B. (2012). Suppression of Clostridium difficile in the Gastrointestinal Tracts of Germfree Mice Inoculated with a Murine Isolate from the Family Lachnospiraceae. Infection and Immunity 80(11), 3786-3794.
Rexroad, J., Wiethoff, C.M., Jones, L.S., and Middaugh, C.R. (2002). Lyophilization and the thermostability of vaccines. Cell Preservation Technology 1(2), 91-104.
Ridaura, V.K., Faith, J.J., Rey, F.E., Cheng, J., Duncan, A.E., Kau, A.L., Griffin, N.W., Lombard, V., Henrissat, B., Bain, J.R., et al. (2013). Gut Microbiota from Twins Discordant for Obesity Modulate Metabolism in Mice. Science 341(6150),1241214-1241214.
Robinson, I.M. et al., "Emendation of Acetivibrio and Description of Acetivibrio ethanolgignens, a New Species from the Colons of Pigs with Dysentery," International Journal of Systematic Bacteriology, Jul. 1981, pp. 333-338, vol. 31, No. 3.
Rode, L.J., and Foster, J.W. (1961). Germination of bacterial spores with alkyl primary amines1. J Bacteriol 81(5), 768-779.
Roffe, C. (1996). Biotherapy for antibiotic-associated and other diarrhoeas. J. Infect. 32(1), 1-10.
Rohlke, F., Surawicz, C.M., and Stollman, N. (2010). Fecal flora reconstitution for recurrent Clostridium difficile infection: results and methodology. J. Clin. Gastroenterol. 44(8), 567-570.
Rosen, D.L., Sharpless, C., and McGown, L.B. (1997). Bacterial Spore Detection and Determination by Use of Terbium Dipicolinate Photoluminescence. Anal. Chem. 69(6), 1082-1085.
Russell, A.D., "The Destruction of Bacterial Spores," 1982, pp. 191-193.
Russian Office Action, Russian Application No. 2015137399, dated Mar. 22, 2016, 8 pages.
Sack, D.A., Shimko, J., Sack, R.B., Gomes, J.G., Macleod, K., O'Sullivan, D., and Spriggs, D. (1997). Comparison of alternative buffers for use with a new live oral cholera vaccine, Peru-15, in outpatient volunteers. Infect. Immun. 65(6), 2107-2111.
Sacks, L.E., and Alderton, G. (1961). Behavior of bacterial spores in aqueous polymer two-phase systems. J. Bacteriol. 82,331-341.
Sahlström, L., Bagge, E., Emmoth, E., Holmqvist, A., Danielsson-Tham, M.-L., and Albihn, A. (2008). A laboratory study of survival of selected microorganisms after heat treatment of biowaste used in biogas plants. Bioresour. Technol. 99(16), 7859-7865.
Santivarangkna, C., Kulozik, U., and Foerst, P. (2007). Alternative Drying Processes for the Industrial Preservation of Lactic Acid Starter Cultures. Biotechnology Progress 23(2), 302-315.
Sattar, S.A., Jason, T., Bidawid, S., and Farber, J. (2000). Foodborne spread of hepatitis A: recent studies on virus survival, transfer and inactivation. The Canadian Journal of Infectious Diseases 11(3), 159.
Savaiano, D.A., Ritter, A.J., Klaenhammer, T., Walker, M.R., Carlson, H.L.F., and Ruckle, J. (2012). A Novel High Purity Short-Chain Galacto-Oligosaccharide (RP-G28) Improves Lactose Digestion and Symptoms of Lactose Intolerance. Gastroenterology 142(5), S-182.
Savaiano, D.A., Ritter, A.J., Klaenhammer, T.R., Walker, W.A., James, G.M., Longcore, A.T., Chandler, J.R., and Foyt, H.L. (2013). Improving lactose digestion and symptoms of lactose intolerance with a novel galacto-oligosaccharide (RP-G28): a randomized, double-blind clinical trial. Nutrition Journal 12(1), 160.
Seale, R.B., Flint, S.H., Mcquillan, A.J., and Bremer, P.J. (2008). Recovery of Spores from Thermophilic Dairy *Bacilli* and Effects of Their Surface Characteristics on Attachment to Different Surfaces. Appl Environ Microbiol 74(3), 731-737.
Seo, M., Inoue, I., Tanaka, M., Matsuda, N., Nakano, T., Awata, T., Katayama, S., Alpers, D.H., and Komoda, T. (2013). Clostridium butyricum Miyairi 588 improves high-fat diet-induced non-alcoholic fatty liver disease in rats. Dig. Dis. Sci. 58(12), 3534-3544.
Setlow, B., Cowan, A. E., and Setlow, P. (2003). Germination of spores of *Bacillus subtilis* with dodecylamine. Journal of Applied Microbiology 95(3), 637-648.
Setlow, B., Yu, J., Li, Y.-Q., and Setlow, P. (2013). Analysis of the germination kinetics of individual *Bacillus subtilis* spores treated with hydrogen peroxide or sodium hypochlorite. Letters in Applied Microbiology 57(4), 259-265.
Shafaat, H.S., and Ponce, A. (2006). Applications of a Rapid Endospore Viability Assay for Monitoring UV Inactivation and Characterizing Arctic Ice Cores. Appl Environ Microbiol 72(10), 6808-6814.
Shah, I.M., Laaberki, M.-H., Popham, D.L., and Dworkin, J. (2008). A eukaryotic-like Ser/Thr kinase signals bacteria to exit dormancy in response to peptidoglycan fragments. Cell 135(3), 486-496.
Shah, N.P., "Symposium: Probiotic Bacteria: Probiotic Bacteria: Selective Enumeration and Survival in Dairy Foods," Oct. 7, 1999, 14 pages.
Shah, N.P. et al., "Microencapsulation of Probiotic Bacteria and Their Survival in Frozen Fermented Dairy Desserts," The Australian Journal of Dairy Technology, Oct. 2000, pp. 139-144, vol. 55, No. 3.
Shah, S. (2012). Clostridium difficile in inflammatory Bowel Disease: a dangerous mix (Clostridium difficile Symposium, Miriam Hospital, Providence, RI).
Shahinas, D., Silverman, M., Sittler, T., Chiu, C., Kim, P., Allen-Vercoe, E., Weese, S., Wong, A., Low, D.E., and Pillai, D.R. (2012). Toward an Understanding of Changes in Diversity Associated with

(56) References Cited

OTHER PUBLICATIONS

Fecal Microbiome Transplantation Based on 16S rRNA Gene Deep Sequencing. mBio 3(5), e00338-12-e00338-12.
Sharpe, E.S., Nickerson, K.W., Bulla Jr, L.A., and Aronson, J.N. (1975). Separation of spores and parasporal crystals of Bacillus thuringiensis in gradients of certain x-ray contrasting agents. Applied Microbiology 30(6), 1052.
Sheu, T.-Y., Marshall, R.T., and Heymann, H. (1993). Improving Survival of Culture Bacteria in Frozen Desserts by Microentrapment. Journal of Dairy Science 76(7), 1902-1907.
Siaterlis, A., Deepika, G., and Charalampopoulos, D. (2009). Effect of culture medium and cryoprotectants on the growth and survival of probiotic lactobacilli during freeze drying. Letters in Applied Microbiology 48(3), 295-301.
Sigma-Tau. VSL#3. <http://www.vsl3.com/> Accessed Mar. 21, 2014.
Skaar, E., "The Battle for Iron Between Bacterial Pathogens and Their Vertebrate Hosts," PLoS Pathog., Aug. 12, 2010, pp. 1-4, vol. 6, No. 8.
Sleator, R.D. et al.,"Designer Probiotics: A Potential Therapeutic for Clostridium difficile?" Journal of Medical Microbiology, Jun. 2008, pp. 793-794, vol. 57, No. 6.
Snitkin, E.S., Zelazny, A.M., Thomas, P.J., Stock, F., Henderson, D.K., Palmore, T.N., and Segre, J.A. (2012). Tracking a Hospital Outbreak of Carbapenem-Resistant Klebsiella pneumoniae with Whole-Genome Sequencing. Sci Transl Med 4(148), 148ra116-148ra116.
Solanki, H.K., Pawar, D.D., Shah, D.A., Prajapati, V.D., Jani, G.K., Mulla, A.M., and Thakar, P.M. (2013). Development of Microencapsulation Delivery System for Long-Term Preservation of Probiotics as Biotherapeutics Agent. BioMed Research International 2013, 1-21.
SOP No. MB-28-00. <http://www.epa.gov/pesticides/methods/MB-28-00.pdf> Accessed Mar. 27, 2014.
Sorg, J.A., and Sonenshein, A.L. (2008). Bile Salts and Glycine as Cogerminants for Clostridium difficile Spores. J Bacteriol 190(7), 2505-2512.
Sow, H., Desbiens, M., Morales-Rayas, R., Ngazoa, S.E., and Jean, J. (2011). Heat Inactivation of Hepatitis A Virus and a Norovirus Surrogate in Soft-Shell Clams (*Mya arenaria*). Foodborne Pathogens and Disease 8(3), 387-393.
Stams, A.J.M., Van Dijk, J.B., Dijkema, C., and Plugge, C.M. (1993). Growth of Syntrophic Propionate-Oxidizing Bacteria with Fumarate in the Absence of Methanogenic Bacteria. Appl Environ Microbiol 59(4), 1114-1119.
Stefka, A.T. et al., "Commensal Bacteria Protect Against Food Allergen Sensitization," PNAS, Sep. 9, 2014, pp. 13145-13150, vol. 111, No. 36.
Stevens, K.A., and Jaykus, L.-A. (2004). Bacterial Separation and Concentration from Complex Sample Matrices: A Review. Critical Reviews in Microbiology 30(1), 7-24.
Su, W.J., Waechter, M.J., Bourlioux, P., Dolegeal, M., Fourniat, J., and Mahuzier, G. (1987). Role of volatile fatty acids in colonization resistance to Clostridium difficile in gnotobiotic mice. Infect. Immun. 55(7), 1686-1691.
Talwalkar, A., and Kailasapathy, K. (2003). Effect of microencapsulation on oxygen toxicity in probiotic bacteria. Australian Journal of Dairy Technology 58(1), 36-39
Tamir, H., and Gilvarg, C. (1966). Density Gradient Centrifugation for the Separation of Sporulating Forms of Bacteria. J. Biol. Chem. 241(5), 1085-1090.
Tanaka, M. et al., "Increased Fasting Plasma Ghrelin Levels in Patients with Bulimia Nervosa," European Journal of Endocrinology, Jun. 2002, pp. 1-3, vol. 146.
Taur, Y., and Pamer, E.G. (2014). Harnessing Microbiota to Kill a Pathogen: Fixing the microbiota to treat Clostridium difficile infections. Nature Medicine 20(3), 246-247.
Taur, Y., Xavier, J.B., Lipuma, L., Ubeda, C., Goldberg, J., Gobourne, A., Lee, Y.J., Dubin, K.A., Socci, N.D., Viale, A., et al. (2012). Intestinal Domination and the Risk of Bacteremia in Patients Undergoing Allogeneic Hematopoietic Stem Cell Transplantation. Clin Infect Dis 55(7), 905-914.
The Human Microbiome Project Consortium (2012). Structure, function and diversity of the healthy human microbiome. Nature 486(7402), 207-214.
Tisa, L.S., Koshikawa, T., and Gerhardt, P. (1982). Wet and dry bacterial spore densities determined by buoyant sedimentation. Applied and Environmental Microbiology 43(6), 1307-1310.
Tvede, M., and Rask-Madsen, J. (1989). Bacteriotherapy for chronic relapsing Clostridium difficile diarrhoea in six patients. Lancet 1(8648), 1156-1160.
Ubeda, C., Bucci, V., Caballero, S., Djukovic, A., Toussaint, N.C., Equinda, M., Lipuma, L., Ling, L., Gobourne, A., No, D., et al. (2013). Intestinal Microbiota Containing *Barnesiella* Species Cures Vancomycin-Resistant Enterococcus faecium Colonization. Infect. Immun. 81(3), 965-973.
Ubeda, C., Taur, Y., Jenq, R.R., Equinda, M.J., Son, T., Samstein, M., Viale, A., Socci, N.D., Van Den Brink, M.R.M., Kamboj, M., et al. (2010). Vancomycin-resistant Enterococcus domination of intestinal microbiota is enabled by antibiotic treatment in mice and precedes bloodstream invasion in humans. Journal of Clinical Investigation 120(12), 4332-4341.
United States Office Action, U.S. Appl. No. 14/313,828, dated Aug. 13, 2014, 5 pages.
United States Office Action, U.S. Appl. No. 14/313,828, dated Dec. 10, 2014, 7 papges.
United States Office Action, U.S. Appl. No. 14/313,828, dated May 15, 2015, 11 pages.
United States Office Action, U.S. Appl. No. 14/221,190, dated Jul. 22, 2014, 19 pages.
United States Office Action, U.S. Appl. No. 14/091,201, dated Mar. 25, 2014, 19 pages.
United States Office Action, U.S. Appl. No. 14/197,044, dated Aug. 13, 2014, 5 pages.
United States Office Action, U.S. Appl. No. 14/592,481, dated Dec. 22, 2015, 21 pages.
United States Office Action, U.S. Appl. No. 15/068,438, dated Apr. 28, 2016, 9 pages.
United States Office Action, U.S. Appl. No. 14/884,655, dated May 5, 2016, 10 pages.
United States Office Action, U.S. Appl. No. 14/884,655, dated Aug. 17, 2016, 9 pages.
United States Office Action, U.S. Appl. No. 14/765,812, dated Aug. 25, 2016, 10 pages.
Van Der Woude, M.W., and Baumler, A.J. (2004). Phase and Antigenic Variation in Bacteria. Clin Microbiol Rev 17(3), 581-611.
Van Immerseel, F. et al., "Butyric Acid-Producing Anaerobic Bacteria as a Novel Probiotic Treatment Approach for Inflammatory Bowel Disease," Journal of Medical Microbiology, JMM Editorial, 2010, pp. 141-143.
Van Kregten, E., Westerdaal, N.A., and Willers, J.M. (1984). New, simple medium for selective recovery of Klebsiella pneumoniae and Klebsiella oxytoca from human feces. J Clin Microbiol 20(5), 936-941.
Van Nood, E., Vrieze, A., Nieuwdorp, M., Fuentes, S., Zoetendal, E.G., De Vos, W.M., Visser, C.E., Kuijper, E.J., Bartelsman, J.F.W. M., Tijssen, J.G.P., et al. (2013). Duodenal Infusion of Donor Feces for Recurrent Clostridium difficile. New England Journal of Medicine 368(5), 407-415.
Vandenplas, Y., Veereman, G., Van Der Werff Ten Bosch, J., Goossens, A., Pierard, D., Samsom, J.N., and Escher, J.C. (2014). Fecal Microbial Transplantation in a One-Year-Old Girl with Early Onset Colitis—Caution Advised: Journal of Pediatric Gastroenterology and Nutrition 1.
Vidal, M., Forestier, C., Charbonnel, N., Henard, S., Rabaud, C., and Lesens, O. (2010). Probiotics and Intestinal Colonization by Vancomycin-Resistant Enterococci in Mice and Humans. J Clin Microbial 48(7), 2595-2598.
Villano, S.A., Seiberling, M., Tatarovvicz, W., Monnot-Chase, E., and Gerding, D.N. (2012). Evaluation of an Oral Suspension of VP20621, Spores of Nontoxigenic Clostridium difficile Strain M3, in Healthy Subjects. Antimicrobial Agents and Chemotherapy 56(10), 5224-5229.

(56) References Cited

OTHER PUBLICATIONS

Wagman, J., and Weneck, E.J. (1963). Preservation of bacteria by circulating-gas freeze drying. Applied Microbiology 11(3), 244-248.
Waites, W.M., and Wyatt, L.R. (1971). Germination of spores of Clostridium bifermentans by certain amino acids, lactate and pyruvate in the presence of sodium or potassium ions. J. Gen. Microbiol. 67(2), 215-222.
Waites, W.M., and Wyatt, L.R. (1974). The effect of pH, germinants and temperature on the germination of spores of Clostridium bifermentans. J. Gen. Microbiol. 80(1), 253-258.
Walker, A.W., and Lawley, T.D. (2012). Therapeutic modulation of intestinal dysbiosis. Pharmacological Research 69(1), 75-86.
Wang, M. et al., "Comparison of Bacterial Diversity Along the Human Intestinal Tract by Direct Cloning and Sequencing of 16S rRNA Genes," FEMS Microbiology Ecology, 2005, pp. 219-231, vol. 54.
Wang, S., and Curtiss III, R. (2014). Development of *Streptococcus pneumoniae* Vaccines Using Live Vectors. Vaccines 2(1), 49-88.
Weingarden, A.R., Chen, C., Bobr, A., Yao, D., Lu, Y., Nelson, V.M., Sadowsky, M.J., and Khoruts, A. (2013). Microbiota transplantation restores normal fecal bile acid composition in recurrent Clostridium difficile infection. AJP: Gastrointestinal and Liver Physiology 306(4), G310-G319.
Wiencek, K.M. et al., "Hydrophobicity of Bacillus and Clostridium Spores," Applied and Environmental Microbiology, Sep. 1990, pp. 2600-2605, vol. 56, No. 9.
Wilson, K.H., and Sheagren, J.N. (1983). Antagonism of toxigenic Clostridium difficile by nontoxigenic C. difficile. Journal of Infectious Diseases 147(4), 733.
Wilson, K.H., Silva, J., and Fekety, F.R. (1981). Suppression of Clostridium difficile by Normal Hamster Cecal Flora and Prevention of Antibiotic-Associated Cecitis. Infect Immun 34(2), 626-628.
Wilson, K. et al., "Role of Competition for Nutrients in Suppression of Clostridium difficile by The Colonic Microflora," Infection and Immunity, Oct. 1988, pp. 2610-2614, vol. 56, No. 10.
Woo, T.D.H., Oka, K., Takahashi, M., Hojo, F., Osaki, T., Hanawa, T., Kurata, S., Yonezawa, H., and Kamiya, S. (2011). Inhibition of the cytotoxic effect of Clostridium difficile in vitro by Clostridium butyricum MIYAIRI 588 strain. J. Med. Microbiol. 60(Pt 11), 1617-1625.
Wróbel, B. (2008). Statistical measures of uncertainty for branches in phylogenetic trees inferred from molecular sequences by using model-based methods. J. Appl. Genet. 49(1), 49-67.
Wroblewski, D., Hannett, G.E., Bopp, D.J., Dumyati, G.K., Halse, T.A., Dumas, N.B., and Musser, K.A. (2009). Rapid Molecular Characterization of Clostridium difficile and Assessment of Populations of C. difficile in Stool Specimens. Journal of Clinical Microbiology 47(7), 2142-2148.
Yamakawa, K. et al., "Enhancement of Clostridium difficile Toxin Production in Biotin-Limited Conditions," J. Med. Microbiol., Feb. 1996, pp. 111-114, vol. 44, No. 2.
Yamamura, H., Hayakawa, M., and Iimura, Y. (2003). Application of sucrose-gradient centrifugation for selective isolation of *Nocardia* spp. from soil. Journal of Applied Microbiology 95(4), 677-685.
Yang, W.-W., and Ponce, A. (2009). Rapid endospore viability assay of *Clostridium sporogenes* spores. International Journal of Food Microbiology 133(3), 213-216.
Yang, W.-W., and Ponce, A. (2011). Validation of a Clostridium Endospore Viability Assay and Analysis of Greenland Ices and Atacama Desert Soils. Appl. Environ. Microbiol. 77(7), 2352-2358.
Yang, W.-W., Crow-Willard, E.N., and Ponce, A. (2009). Production and characterization of pure Clostridium spore suspensions. J. Appl. Microbiol. 106(1), 27-33.
Yang, W.W. (2010). Fast Viability Assessment of Clostridium Spores Survival in Extreme Environments. PhD thesis California Institute of Technology.
Yi, X., and Setlow, P. (2010). Studies of the Commitment Step in the Germination of Spores of *Bacillus* Species. J. Bacteriol. 192(13), 3424-3433.
Yung, P.T., and Ponce, A. (2008). Fast Sterility Assessment by Germinable-Endospore Biodosimetry. Appl. Environ. Microbiol. 74(24), 7669-7674.
Yunoki, M., Tsujikawa, M., Urayama, T., Sasaki, Y., Morita, M., Tanaka, H., Hattori, S., Takechi, K., and Ikuta, K. (2003). Heat sensitivity of human parvovirus B19. Vox Sanguinis 84(3), 164-169.
Zeng, Y., Fan, H., Chiueh, G., Pham, B., Martin, R., Lechuga-Ballesteros, D., Truong, V.L., Joshi, S.B., and Middaugh, C.R. (2009). Towards development of stable formulations of a live attenuated bacterial vaccine: a preformulation study facilitated by a biophysical approach. Hum Vaccin 5(5), 322-331.
Zhao, J., Krishna, V., Moudgil, B., and Koopman, B. (2008). Evaluation of endospore purification methods applied to Bacillus cereus. Separation and Purification Technology 61(3), 341-347.
European Examination Report, European Application No. 14746341.8, dated Jun. 13, 2017, 11 pages.
New Zealand First Examination Report, New Zealand Application No. 713298, dated Feb. 28, 2017, 6 pages.
Australian First Examination Report, Australian Application No. 2014232370, dated Oct. 19, 2017, 4 pages.
Australian First Examination Report, Australian Application No. 2014212004, dated Sep. 21, 2017, 6 pages.
Chinese First Office Action, Chinese Application No. 201480019395.8, dated Jul. 17, 2017, 29 pages.
European Partial Supplementary Search Report, European Application No. 14870947.0, dated Jul. 11, 2017, 14 pages.
European Extended Search Report, European Application No. 14870947.0, dated Oct. 17, 2017, 11 pages.
European Examination Report, European Application No. 14745749.3, dated Oct. 31, 2017, 3 pages.
European Examination Report, European Application No. 14746455.6, dated Oct. 31, 2017, 6 pages.
European Examination Report, European Application No. 14763266.5, dated Nov. 13, 2017, 4 pages.
European Examination Report, European Application No. 14768281.9, dated Dec. 18, 2017, 4 pages.
European Examination Report, European Application No. 14745792.3, dated Dec. 21, 2017, 6 pages.
Japanese First Office Action, Japanese Application No. P2015-544179, dated Sep. 19, 2017, 8 pages.
Japanese Office Action, Japanese Application No. 2015-556241, dated Sep. 26, 2017, 12 pages.
Japanese Office Action, Japanese Application No. 2015-556240, dated Oct. 3, 2017, 8 pages.
Li, A-D. et al., "Clinical Features and Bacterial Culture on Stools of Patients with Acute Diarrhea," Chinese Journal of Health Laboratory Technology, Mar. 10, 2012, pp. 559-561, vol. 2, No. 6.
New Zealand Examination Report, New Zealand Application No. 713298, dated Sep. 26, 2017, 5 pages.
Pharmacy, 2011, pp. 79-86, vol. 62, No. 3. [With English Main Sub-Points].
Plassart, C. et al., "First Case of Intra-Abdominal Infection with Clostridium Disporicum," Anaerobe, 2013, pp. 77-78, vol. 19.
Rehman, A. et al., "Effect of Probiotics and Antibiotics on the Intestinal Homeostasis in a Computer Controlled Model of the Large Intestine," BMC Microbiology, 2012, 10 pages, vol. 12, No. 47.
United States Office Action, U.S. Appl. No. 14/777,252, dated Aug. 29, 2017, 16 pages.
United States Office Action, U.S. Appl. No. 15/039,007, dated Nov. 1, 2017, 13 pages.
United States Office Action, U.S. Appl. No. 14/765,812, dated Dec. 7, 2017, 10 pages.
United States Office Action, U.S. Appl. No. 14/765,810, dated Jan. 8, 2018, 8 pages.
United States Office Action, U.S. Appl. No. 14/765,810, dated Jan. 25, 2018, 11 pages.

(56) References Cited

OTHER PUBLICATIONS

Yuguchi Hiroya et al., "Hakkonyuu/nyuusankin inryou to chounaikinsou "Fermented Milk/Lactic Acid Bacteria Beverages and Intestinal Bacterial Flora,"" New Food Industry, UDA, Moritaka, New Food Industry K.K., 1987, pp. 71-88, vol. 29, No. 7. [With English Subtitle Translations].

* cited by examiner

Table1.

| OTU | Taxonomic Family |
|---|---|
| Bacteroides caccae | Bacteroidaceae |
| Bacteroides dorei | Bacteroidaceae |
| Bacteroides finegoldii | Bacteroidaceae |
| Bacteroides fragilis | Bacteroidaceae |
| Bacteroides galacturonicus | Bacteroidaceae |
| Bacteroides ovatus | Bacteroidaceae |
| Bacteroides sp. 3_1_19 | Bacteroidaceae |
| Bacteroides stercoris | Bacteroidaceae |
| Bacteroides xylanisolvens | Bacteroidaceae |
| Christensenella minuta | Christensenellaceae |
| Butyricicoccus pullicaecorum | Clostridiaceae |
| Clostridiales bacterium | Clostridiaceae |
| Clostridiales sp. SM4/1 | Clostridiaceae |
| Clostridium symbiosum | Clostridiaceae |
| Collinsella aerofaciens | Coriobacteriaceae |
| Gordonibacter pamelaeae | Coriobacteriaceae |
| Holdemania filiformis | Erysipelotrichaceae |
| Eubacterium cellulosolvens | Eubacteriaceae |
| Eubacterium eligens | Eubacteriaceae |
| Eubacterium hadrum | Eubacteriaceae |
| Eubacterium hallii | Eubacteriaceae |
| Eubacterium rectale | Eubacteriaceae |
| Eubacterium siraeum | Eubacteriaceae |
| Eubacterium ventriosum | Eubacteriaceae |
| Blautia luti | Lachnospiraceae |
| Blautia stercoris | Lachnospiraceae |
| Blautia wexlerae | Lachnospiraceae |
| Coprococcus catus | Lachnospiraceae |
| Coprococcus comes | Lachnospiraceae |
| Dorea formicigenerans | Lachnospiraceae |
| Dorea longicatena | Lachnospiraceae |
| Lachnospiraceae 3_1_57FAA_CT1 | Lachnospiraceae |
| Roseburia hominis | Lachnospiraceae |
| Roseburia intestinalis | Lachnospiraceae |
| Roseburia inulinivorans | Lachnospiraceae |
| Oscillibacter valericigenes | Oscillospiraceae |
| Odoribacter splanchnicus | Porphyromonadaceae |
| Alistipes putredinis | Rikenellaceae |
| Alistipes shahii | Rikenellaceae |
| Alistipes sp HGB5 | Rikenellaceae |
| Faecalibacterium prausnitzii | Ruminococcaceae |
| Ruminococcaceae bacterium D16 | Ruminococcaceae |
| Ruminococcus bromii | Ruminococcaceae |
| Ruminococcus gnavus | Ruminococcaceae |
| Ruminococcus lactaris | Ruminococcaceae |
| Ruminococcus obeum | Ruminococcaceae |
| Ruminococcus torques | Ruminococcaceae |
| Subdoligranulum variabile | Ruminococcaceae |
| Streptococcus mitis | Streptococcaceae |
| Streptococcus thermophilus | Streptococcaceae |
| Veillonella parvula | Veillonellaceae |

FIG. 1

Table 2.

| OTU | | |
|---|---|---|
| Acidaminococcus sp. D21 | Clostridium clostridioforme | Lachnospiraceae bacterium |
| Adlercreutzia equolifaciens | Clostridium hathewayi | Lactobacillus acidophilus |
| Akkermansia muciniphila | Clostridium hylemonae | Lactobacillus amylolyticus |
| Alistipes indistinctus | Clostridium leptum | Lactobacillus brevis |
| Anaerococcus hydrogenalis | Clostridium methylpentosum | Lactobacillus casei |
| Anaerofustis stercorihominis | Clostridium nexile | Lactobacillus delbrueckii |
| Anaerostipes caccae | Clostridium saccharolyticum | Lactobacillus fermentum |
| Anaerostipes sp. 3_2_56FAA | Clostridium scindens | Lactobacillus gasseri |
| Anaerotruncus colihominis | Clostridium sp. D5 | Lactobacillus helveticus |
| Bacteroides cellulosilyticus | Clostridium sp. L2_50 | Lactobacillus johnsonii |
| Bacteroides coprocola | Clostridium sp. NML_04A032 | Lactobacillus mucosae |
| Bacteroides coprophilus | Clostridium sp. YIT_12069 | Lactobacillus paracasei |
| Bacteroides eggerthii | Clostridium sp. YIT_12070 | Lactobacillus plantarum |
| Bacteroides faecis | Collinsella intestinalis | Lactobacillus reuteri |
| Bacteroides intestinalis | Collinsella stercoris | Lactobacillus rhamnosus |
| Bacteroides pectinophilus | Coprobacillus sp. D7 | Lactobacillus ruminis |
| Bacteroides plebeius | Coprococcus eutactus | Lactobacillus salivarius |
| Bacteroides salyersiae | Cronobacter turicensis | Leminorella grimontii |
| Bacteroides sp. 1_1_30 | Desulfitobacterium frappieri | Leuconostoc citreum |
| Bacteroides sp. 20_3 | Desulfovibrio desulfuricans | Leuconostoc mesenteroides |
| Bacteroides sp. 2_1_56FAA | Desulfovibrio piger | Marvinbryantia formatexigens |
| Bacteroides sp. 3_1_23 | Dialister invisus | Megamonas hypermegale |
| Bacteroides sp. 3_2_5 | Edwardsiella tarda | Megasphaera micronuciformis |
| Bacteroides sp. 4_3_47FAA | Enterococcus durans | Methanosphaera stadtmanae |
| Bacteroides sp. 9_1_42FAA | Enterococcus faecalis | Mitsuokella multacida |
| Bacteroides sp. D2 | Enterococcus faecium | Morganella sp. JB_T16 |
| Bacteroides sp. D20 | Enterococcus gallinarum | Odoribacter laneus |
| Bacteroides sp. NB_8 | Enterococcus hirae | Oscillibacter sp. G2 |
| Bacteroides sp. WAL_11050 | Enterococcus raffinosus | Oxalobacter formigenes |
| Bacteroides thetaiotaomicron | Escherichia coli | Pantoea ananatis |
| Bacteroides uniformis | Ethanoligenens harbinense | Parabacteroides distasonis |
| Bacteroides vulgatus | Eubacterium brachy | Parabacteroides goldsteinii |
| Bifidobacterium adolescentis | Eubacterium limosum | Parabacteroides johnsonii |
| Bifidobacterium angulatum | Eubacterium ramulus | Parabacteroides merdae |
| Bifidobacterium animalis | Finegoldia magna | Parasutterella excrementihominis |
| Bifidobacterium bifidum | Flavonifractor plautii | Porphyromonas gingivalis |
| Bifidobacterium breve | Fusobacterium gonidiaformans | Prevotella copri |
| Bifidobacterium catenulatum | Fusobacterium mortiferum | Prevotella salivae |
| Bifidobacterium dentium | Fusobacterium sp. 11_3_2 | Propionibacterium freudenreichii |
| Bifidobacterium longum | Fusobacterium sp. CM1 | Pseudoflavonifractor capillosus |
| Bifidobacterium pseudocatenulatum | Fusobacterium ulcerans | Roseburia faecalis |
| Bilophila wadsworthia | Fusobacterium gonidiaformans | Roseburia faecis |
| Blautia hansenii | Fusobacterium mortiferum | Ruminococcus albus |
| Blautia hydrogenotrophica | Fusobacterium sp. 11_3_2 | Sutterella wadsworthensis |
| Blautia producta | Fusobacterium sp. CM1 | Syntrophomonadaceae genomosp. P1 |
| Butyricimonas virosa | Fusobacterium ulcerans | Tannerella forsythia |
| Butyrivibrio crossotus | Fusobacterium varium | Tannerella sp. 6_1_58FAA |
| Catenibacterium mitsuokai | Granulicatella adiacens | Turicibacter sanguinis |
| Clostridiales genomosp. BVAB3_UPII9_5 | Lachnospiraceae 1 | Veillonella atypica |
| Clostridiales sp. SS3_4 | Lachnospiraceae 4 | Veillonella sp. 3_1_44 |
| Clostridium asparagiforme | Lachnospiraceae 5 | Victivallis vadensis |
| Clostridium bartlettii | Lachnospiraceae 6 | |
| Clostridium bolteae | Lachnospiraceae 9 | |

FIG. 2

Table 3.

| Keystone Families | Keystone Genera |
|---|---|
| Bacteroidaceae | Bacteroides |
| Christensenellaceae | Christensenella |
| Clostridiaceae | Butyricicoccus |
| Clostridiaceae | Clostridium |
| Coriobacteriaceae | Collinsella |
| Coriobacteriaceae | Gordonibacter |
| Erysipelotrichaceae | Holdemania |
| Eubacteriaceae | Eubacterium |
| Lachnospiraceae | Blautia |
| Lachnospiraceae | Coprococcus |
| Lachnospiraceae | Dorea |
| Lachnospiraceae | Roseburia |
| Oscillospiraceae | Oscillibacter |
| Porphyromonadaceae | Odoribacter |
| Rikenellaceae | Alistipes |
| Ruminococcaceae | Faecalibacterium |
| Ruminococcaceae | Ruminococcus |
| Ruminococcaceae | Subdoligranulum |
| Streptococcaceae | Streptococcus |
| Veillonellaceae | Veillonella |

FIG. 3

Tables 4a-b.
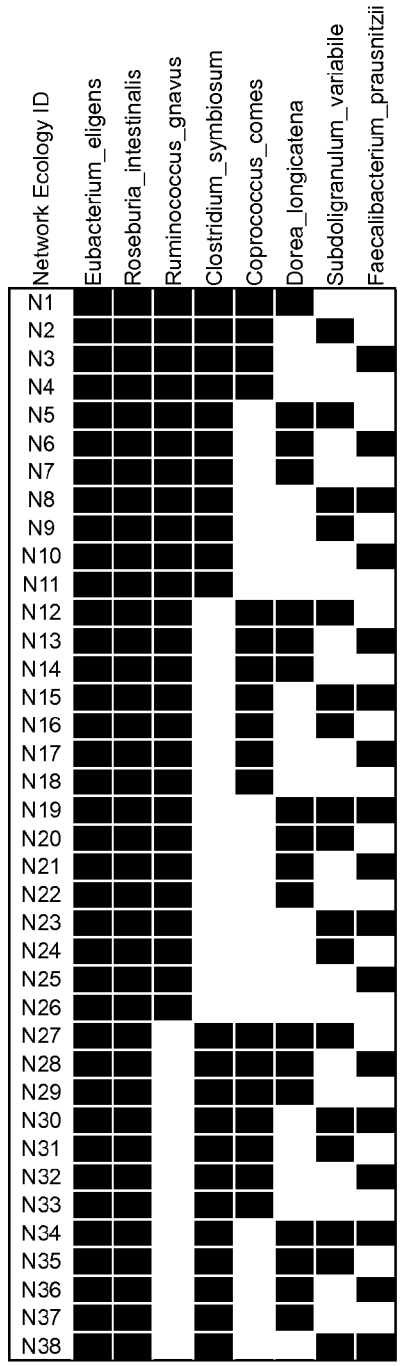
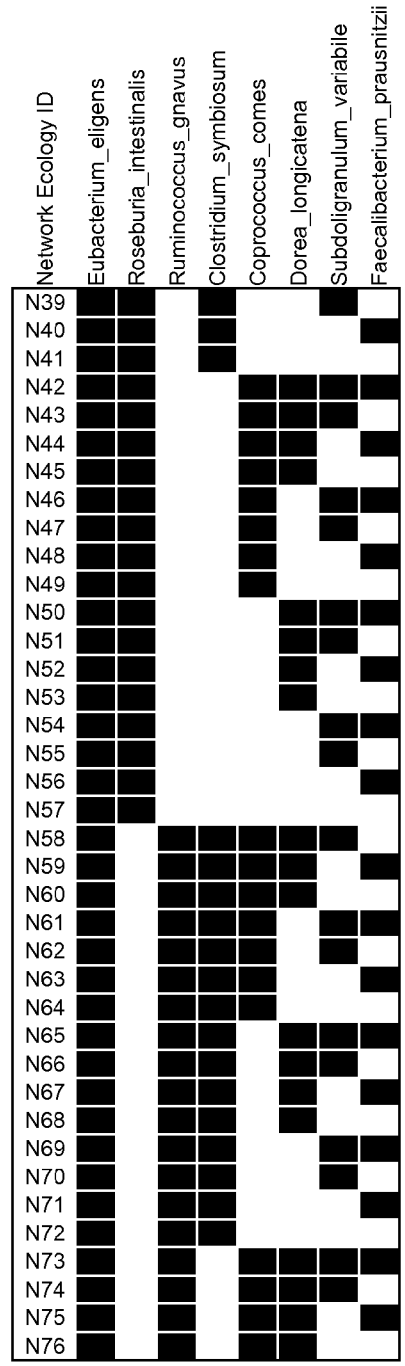
FIG. 4

Tables 4c-d.
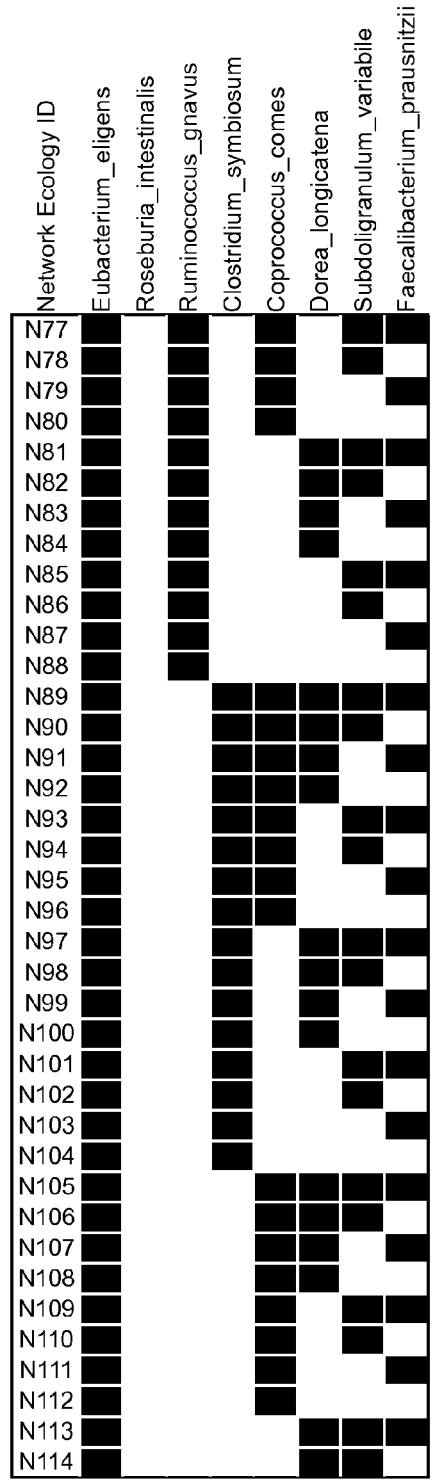
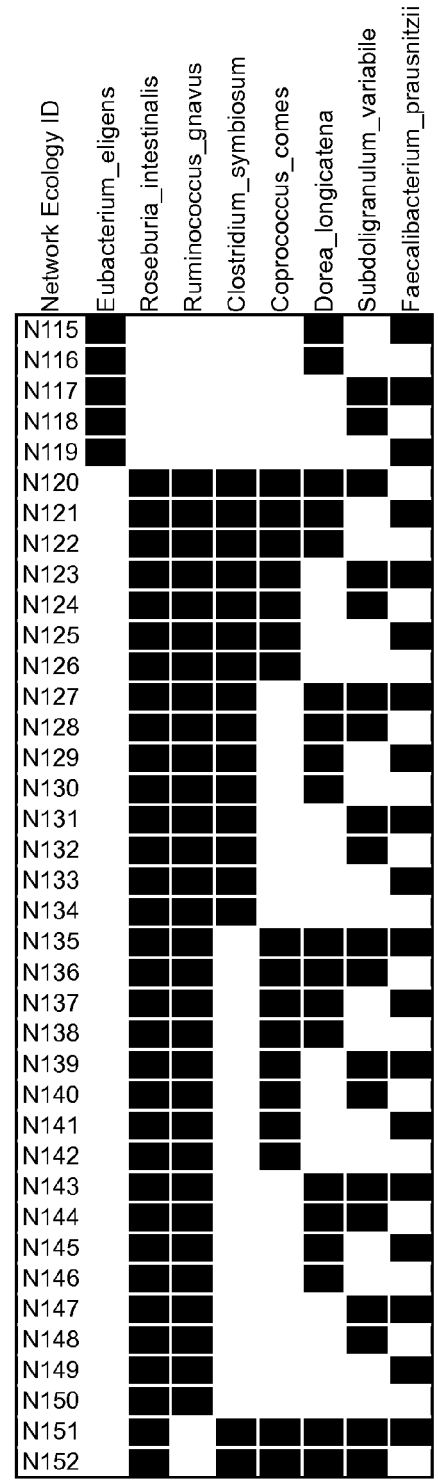
FIG. 4

Tables 4e-f.

FIG. 4

Tables 5a-b.

(a)

| Core Network ID | Faecalibacterium_prausnitzii | Ruminococcus_obeum | Alistipes_putredinis | Alistipes_shahii | Ruminococcus_torques | Coprococcus_catus | Dorea_longicatena | Eubacterium_rectale | Bifidobacterium_adolescentis | Coprococcus_comes | Roseburia_inulinivorans | Clostridium_leptum | Gordonibacter_pamelaeae |
|---|---|---|---|---|---|---|---|---|---|---|---|---|---|
| Core1 | 100 | 100 | 15 | 15 | 99 | 99 | 100 | 100 | 99 | 13 | 99 | 13 | |
| Core2 | 100 | 100 | 100 | 100 | 14 | 100 | 100 | 100 | 100 | 1 | 14 | 16 | |
| Core3 | 100 | 100 | 100 | 100 | 8 | 5 | 100 | 100 | 100 | 100 | 8 | 8 | |
| Core4 | 100 | 100 | 100 | 100 | 100 | 11 | 11 | 14 | | 94 | 10 | 98 | 98 |
| Core5 | 100 | 100 | 100 | 100 | 100 | 97 | 20 | 17 | | 7 | 13 | 91 | 99 |
| Core6 | 100 | 100 | 100 | 100 | 100 | 100 | 11 | 11 | 2 | 82 | 100 | 10 | 19 |

(b)

| Core Network ID | Dorea_formicigenerans | Eubacterium_eligens | Eubacterium_hallii | Subdoligranulum_variabile | Bacteroides_ovatus | Eubacterium_ventriosum | Anaerotruncus_colihominis | Bacteroides_vulgatus | Bacteroides_xylanisolvens | Roseburia_intestinalis |
|---|---|---|---|---|---|---|---|---|---|---|
| Core1 | 13 | 12 | 11 | 13 | 11 | 12 | 9 | 9 | 9 | 11 |
| Core2 | 16 | 15 | 14 | 16 | 10 | 14 | 10 | 11 | 10 | 9 |
| Core3 | 8 | 8 | 8 | 8 | 8 | 8 | 8 | 7 | 8 | 8 |
| Core4 | 13 | 11 | 11 | 11 | 11 | 10 | 10 | 15 | 7 | 6 |
| Core5 | 19 | 20 | 19 | 12 | 17 | 13 | 16 | | 7 | 7 |
| Core6 | 11 | 9 | 10 | 9 | 9 | 9 | 10 | 10 | 5 | 5 |

FIG. 5

Table 5c.

(c)

| Core Network ID | Bacteroides_uniformis | Holdemania_filiformis | Parabacteroides_merdae | Collinsella_aerofaciens | Bacteroides_dorei | Odoribacter_splanchnicus | Bilophila_wadsworthia | Ruminococcus_lactaris | Bacteroides_finegoldii | Bacteroides_thetaiotaomicron | Ruminococcus_gnavus | Bacteroides_caccae | Bacteroides_stercoris | Akkermansia_muciniphila | Bifidobacterium_longum | Eubacterium_siraeum | Ruminococcus_bromii | Bacteroides_cellulosilyticus | Clostridium_asparagiforme | Streptococcus_mitis | Veillonella_parvula | Parabacteroides_distasonis | Escherichia_coli |
|---|---|---|---|---|---|---|---|---|---|---|---|---|---|---|---|---|---|---|---|---|---|---|---|
| Core1 | 7 | 7 | 6 | 7 | 8 |   |   | 3 |   |   |   |   |   |   |   |   |   |   |   |   |   |   |   |
| Core2 | 7 | 3 | 8 | 6 | 7 |   |   |   |   |   |   |   |   |   |   |   |   |   |   |   |   |   |   |
| Core3 | 7 | 7 | 7 | 7 | 7 | 7 | 6 | 7 | 6 | 6 | 4 | 6 | 4 | 5 | 4 | 2 | 2 |   |   |   |   |   |   |
| Core4 | 5 | 6 | 6 | 5 | 3 | 7 | 5 | 7 | 5 | 4 | 5 | 1 | 1 |   |   |   |   |   |   |   |   |   |   |
| Core5 | 6 | 10 |   |   |   | 4 | 4 |   |   |   |   |   |   |   |   |   |   |   |   |   |   |   |   |
| Core6 | 4 | 4 | 3 | 4 | 3 | 6 | 4 | 3 | 6 | 6 | 3 | 4 | 3 | 3 | 3 | 3 | 3 | 3 | 2 | 2 | 2 | 1 | 1 |

FIG. 5

Table 6.

FIG. 6

Table 7.

| Phylogenetic Clade | OTUs |
|---|---|
| clade_61 | Eubacterium siraeum<br>Faecalibacterium prausnitzii<br>Gemmiger formicilis<br>Subdoligranulum variabile |
| clade_101 | Clostridium orbiscindens<br>Clostridium sp NML 04A032<br>Clostridium viride<br>Flavonifractor plautii<br>Oscillibacter sp G2<br>Oscillibacter valericigenes<br>Oscillospira guilliermondii<br>Papillibacter cinnamivorans<br>Pseudoflavonifractor capillosus<br>Ruminococcaceae bacterium D16<br>Sporobacter termitidis |
| clade_242 | Clostridium colinum<br>Clostridium lactatifermentans<br>Clostridium piliforme<br>Peptococcus sp oral clone JM048 |
| clade_6 | Abiotrophia defectiva<br>Abiotrophia sp oral clone P4PA<br>Aerococcus sanguinicola<br>Aerococcus urinae<br>Aerococcus urinaeequi<br>Aerococcus viridans<br>Butyrivibrio fibrisolvens<br>Catonella genomosp P1 oral clone<br>Catonella morbi<br>Catonella sp oral clone FL037<br>Eremococcus coleocola<br>Eubacterium rectale<br>Eubacterium sp oral clone GI038<br>Facklamia hominis<br>Granulicatella sp M658 99 3<br>Lachnobacterium bovis<br>Roseburia inulinivorans |
| clade_25 | Roseburia cecicola<br>Roseburia faecalis<br>Roseburia faecis<br>Roseburia hominis<br>Roseburia intestinalis<br>Roseburia sp 11SE37<br>Roseburia sp 11SE38 |

| Phylogenetic Clade | OTUs |
|---|---|
| clade_87 | Clostridium nexile<br>Coprococcus comes<br>Ruminococcus sp ID8 |
| clade_233 | Acetivibrio ethanolgignens<br>Anaerosporobacter mobilis<br>Anaerostipes caccae<br>Anaerostipes sp 3_2_56FAA<br>Clostridiales sp 1_7_47<br>Clostridiales sp SM4_1<br>Clostridiales sp SSC_2<br>Clostridium aerotolerans<br>Clostridium aldenense<br>Clostridium algidixylanolyticum<br>Clostridium aminovalericum<br>Clostridium amygdalinum<br>Clostridium asparagiforme<br>Clostridium celerecrescens<br>Clostridium citroniae<br>Clostridium clostridiiformes<br>Clostridium clostridioforme<br>Clostridium hathewayi<br>Clostridium indolis<br>Clostridium lavalense<br>Clostridium phytofermentans<br>Clostridium saccharolyticum<br>Clostridium sp M62_1<br>Clostridium sp SS2_1<br>Clostridium sphenoides<br>Clostridium symbiosum<br>Clostridium xylanolyticum<br>Eubacterium hadrum<br>Eubacterium ventriosum<br>Eubacterium xylanophilum<br>Lachnospiraceae bacterium 5_1_63FAA |
| clade_197 | Bifidobacterium adolescentis<br>Bifidobacterium angulatum<br>Bifidobacterium animalis<br>Bifidobacterium bifidum<br>Bifidobacterium breve<br>Bifidobacterium catenulatum<br>Bifidobacterium dentium<br>Bifidobacterium gallicum<br>Bifidobacterium infantis<br>Bifidobacterium kashiwanohense<br>Bifidobacterium longum<br>Bifidobacterium pseudocatenulatum<br>Bifidobacterium pseudolongum<br>Bifidobacterium scardovii<br>Bifidobacterium sp HM2<br>Bifidobacterium sp HMLN12<br>Bifidobacterium sp M45<br>Bifidobacterium sp MSX5B<br>Bifidobacterium sp TM 7<br>Bifidobacterium thermophilum<br>Gardnerella vaginalis |

FIG. 7

Table 8a.

| Ranked OTU Genera |
| --- |
| Alistipes |
| Bacteroides |
| Bilophila |
| Blautia |
| Clostridium |
| Coprococcus |
| Dorea |
| Eubacterium |
| Faecalibacterium |
| Gemmiger |
| Lachnospira |
| Odoribacter |
| Oscillibacter |
| Parabacteroides |
| Roseburia |
| Ruminococcus |
| Sutterella |
| Anaerosporobacter |
| Barnesiella |
| Bifidobacterium |
| Clostridiales |
| Haemophilus |
| Oscillospira |
| Sporobacter |
| Streptococcus |
| Acetivibrio |
| Akkermansia |
| Butyricimonas |
| Dialister |
| Escherichia |
| Prevotella |
| Subdoligranulum |
| [Clostridium] |
| Collinsella |
| Lachnobacterium |
| Phascolarctobacterium |
| Turicibacter |
| Veillonella |
| Tannerella |
| Anaerotruncus |
| Butyrivibrio |
| Herbaspirillum |
| Klebsiella |
| Megamonas |
| Parasutterella |
| Acidaminococcus |
| Citrobacter |
| Holdemania |
| Porphyromonas |
| Pseudoflavonifractor |
| Victivallis |

Table 8b.

| Ranked OTU Family |
| --- |
| Bacteroidaceae |
| Clostridiaceae |
| Coriobacteriaceae |
| Desulfovibrionaceae |
| Eubacteriaceae |
| Hyphomicrobiaceae |
| Lachnospiraceae |
| Oscillospiraceae |
| Porphyromonadaceae |
| Rikenellaceae |
| Ruminococcaceae |
| Sutterellaceae |
| Veillonellaceae |
| Bifidobacteriaceae |
| Erysipelotrichaceae |
| Peptostreptococcaceae |
| Streptococcaceae |
| unclassified |
| Enterobacteriaceae |
| Pasteurellaceae |
| Verrucomicrobiaceae |
| Acidaminococcaceae |
| Prevotellaceae |
| Victivallaceae |
| Oxalobacteraceae |
| Actinomycetaceae |
| Methanobacteriaceae |

FIG. 8

BACTERIAL COMPOSITIONS AND METHODS OF USE THEREOF FOR TREATMENT OF IMMUNE SYSTEM DISORDERS

CROSS REFERENCE TO RELATED APPLICATIONS

This application is the National Stage of International Application No. PCT/US2014/070684, filed Dec. 16, 2014, which claims the benefit of U.S. Provisional Application No. 61/916,761, filed Dec. 16, 2013, each entire disclosure of which is hereby incorporated by reference herein in its entirety for all purposes.

STATEMENT REGARDING FEDERALLY SPONSORED RESEARCH OR DEVELOPMENT

Not applicable.

SEQUENCE LISTING

Not applicable.

BACKGROUND

Mammals are colonized by microbes in the gastrointestinal (GI) tract, on the skin, and in other epithelial and tissue niches such as the oral cavity, eye surface and vagina. The gastrointestinal tract harbors an abundant and diverse microbial community. It is a complex system, providing an environment or niche for a community of many different species or organisms, including diverse strains of bacteria. Hundreds of different species may form a commensal community in the GI tract in a healthy person, and this complement of organisms evolves from the time of birth and is believed to form a functionally mature microbial population by about 3 years of age. Interactions between microbial strains in these populations and between microbes and the subject, e.g., the subject's immune system, shape the community structure, with availability of and competition for resources affecting the distribution of microbes. Such resources may be food, location and the availability of space to grow or a physical structure to which the microbe may attach. For example, a subject's diet is involved in shaping the GI tract flora.

A healthy microbiota provides the subject with multiple benefits, including colonization resistance to a broad spectrum of pathogens, essential nutrient biosynthesis and absorption, and immune stimulation that plays a role in maintaining a healthy gut epithelium and appropriately controlled systemic immunity. In settings of 'dysbiosis' or disrupted symbiosis, microbiota functions can be lost or deranged, resulting in increased susceptibility to pathogens, altered metabolic profiles, or induction of pro-inflammatory signals that can result in local or systemic inflammation or autoimmunity.

The intestinal microbiota reportedly play a significant role in educating the immune system by inducing mechanisms for immune control and regulation. Dysbiotic states of the microbiome may underlie the development of inflammatory states, autoimmunity and hyper-reactive immune states, characterized by disregulation of immune function. Allergies are among the most common health problems affecting the life of patients of all ages. Allergic diseases are recognized as an epidemic by the World Health Organization (WHO). The prevalence of allergies has been reported to be increasing over the past decades. Allergic sensitization in childhood, especially in early childhood and especially to food allergens, is believed to be critical as development of an "allergic phenotype" or "atopy" has been shown to facilitate subsequent sensitization to other allergens. Hence, allergies in childhood can be the first step of an allergic cascade leading to multiple allergies later in life, a process commonly referred to as "atopic march." For example, children with persistent food hypersensitivity early in life were reported to have a dramatically increased risk to develop allergic rhinitis (hay fever) or asthma later in childhood (Ostblom et al., 2008). Children with milder forms of food hypersensitivity also have been reported to be at increased risk for development of respiratory allergies but to a lesser degree than children with persistent food hypersensitivity. Preventing, avoiding, managing, reducing and modulating the allergic reactions in young patients can acutely influence their allergic profile and alter their allergy profile later in life.

There is a need for a method of preventing or inhibiting immune disorders that are associated with a subject's microbiota. One solution to the problem of treating such disorders, as provided herein, is to provide compositions and methods of their use that can facilitate populating a subject's gastrointestinal tract and/or other bacterial niches with a diverse and useful selection of microbiota, to, e.g., improve or maintain general health, to alter a dysbiosis and/or to treat immune disorders such as allergies and asthma. Shortcomings of the prior art are addressed by providing compositions, formulations and methods for consumption by and administration to mammalian subjects including human subjects.

Commensal bacterial and food allergen sensitization are described by Stefka et al. (Stefka et al (2014) PNAS 111:13145-13150).

Compositions comprising isolated bacterial populations and use thereof are described in international application number PCT/US2013/071758, filed on Nov. 25, 2013, published as WO 2014/082050; and in international application number PCT/US2014/014745, filed on Feb. 4, 2014, published as WO 2014/121302, the entire disclosures of which are hereby incorporated by reference in their entirety for all purposes.

SUMMARY OF THE INVENTION

Described herein are preparations comprising isolated bacterial compositions for treating, preventing or reducing the severity of at least one sign and/or symptom associated with an immune system disorder in a human subject, methods of treatment using the isolated bacterial compositions, and methods of identification of isolated bacterial compositions. In some embodiments, the immune system disorder is a hypersensitivity immune disorder, an allergic disorder, a food allergy disorder, allergic conjunctivitis, allergic rhinitis, asthma, atopic dermatitis, atopic/allergic sensitivity, eosinophilic esophagitis, extrinsic allergic alveolitis, food allergy, perennial allergic rhinitis, seasonal allergic rhinitis, skin allergy, asthma or an asthma-related condition.

In some embodiments, the first isolated bacterial population comprises *Clostridium absonum, Clostridium argentinense, Clostridium baratii, Clostridium bifermentans, Clostridium botulinum, Clostridium butyricum, Clostridium cadaveris, Clostridium camis, Clostridium celatum, Clostridium chauvoei, Clostridium clostridioforme, Clostridium cochlearium, Clostridium difficile, Clostridium fallax, Clostridium felsineum, Clostridium ghonii,*

*Clostridium glycolicum, Clostridium haemolyticum, Clostridium hastiforme, Clostridium histolyticum, Clostridium indolis, Clostridium innocuum, Clostridium irregulare, Clostridium limosum, Clostridium malenominatum, Clostridium novyi, Clostridium oroticum, Clostridium paraputrificum, Clostridium perfringens, Clostridium piliforme, Clostridium putrefaciens, Clostridium putrificum, Clostridium ramosum, Clostridium sardiniense, Clostridium sartagoforme, Clostridium scindens, Clostridium septicum, Clostridium sordellii, Clostridium sphenoides, Clostridium spiroforme, Clostridium sporogenes, Clostridium subterminale, Clostridium symbiosum, Clostridium tertium, Clostridium tetani, Clostridium welchii*, or *Clostridium villosum*.

In some embodiments, the first bacterial population is selected from the OTUs found in Table 1 or Table 2, or from the taxonomic Family or Genera found in Table 3. In some embodiments, the first bacterial population is selected from OTUs described in known network ecologies, e.g., those exemplified in Table 4, Table 5a, Table 5b, Table 5c, and Table 6. In some embodiments, the first bacterial population includes a complete network ecology, e.g., those exemplified in Table 4, Table 5a, Table 5b, Table 5c, and Table 6.

In some embodiments, the first bacterial population is capable of forming spores. In some embodiments, the first bacterial population is not directly isolated from a fecal material. In some embodiments, the composition also includes a second bacterial population. In some embodiments, the composition also includes an allergen that can be present in an amount effective to induce tolerance. In some embodiments, the formulation can include immunotherapeutics, anti-angiogenic agents, cytokines, hormones, antibodies, polynucleotides, photodynamic therapeutic agents, non-steroid anti-inflammatory medications, anti-histamines, alpha-adrenergic agonists, steroids, and any combination thereof.

In some embodiments the compositions are formulated as pharmaceutical preparations for oral, topical, nasal, respiratory, parenteral, intraperitoneal, intravenous, intraarterial, transdermal, sublingual, intramuscular, rectal, transbuccal, vaginal, intraocular, subcutaneous, intraadiposal, iintraarticular, intrathecal administration. In some embodiments, the formulation is a slow release formulation. In some embodiments, the compositions are formulated as medical foods, nutritional or dietary supplements, food products or beverage products.

Embodiments also include methods of treating, preventing or reducing severity of at least one symptom associated with an immune system disorder in a human by identifying a human subject in need of treatment and administering to the subject (or if the subject is a fetus, to the mother thereof) an effective amount of a preparation comprising a first isolated bacterial population. In some embodiments, the subject suffers from or is at risk of suffering from: allergic rhinitis, allergic conjunctivitis, allergic bronchial asthma, atopic eczema, anaphylaxis, insect sting, drug allergy, food allergy, asthma, eczema and any combination thereof. In some embodiments, the disorder or condition is associated with a pathological Th17 activity, or the subject has altered Th17 activity.

In some embodiments the method reduces the population of at least one native enteric bacterial OTU, e.g., species or clade, present in the subject, e.g., a bacterial OTU present in the subject before treatment. In some embodiments, the method increases the population of at least one native enteric bacterial OTU, e.g., species or clade either not present in the subject before treatment or not detectable in the subject before treatment. In some embodiments, the reduction or increase in native enteric bacteria or a specific bacterium (e.g., genus, species or clade) is monitored by detection of a metabolite present in blood, plasma, or feces, or a combination thereof.

In some embodiments, the preparation is given prophylactically, or at least daily, or at least twice daily, or prior to, or conconcomitant to, or after consumption of a food or beverage product. In some embodiments, the preparation is administered rectally or orally.

In some embodiments, the invention provides a method of identifying a bacterial composition useful for treating, preventing or reducing the severity of an allergic effect by administering a bacterial test composition to a test subject or group of test subjects, administering an allergen to the test subject or group of test subjects, measuring an allergic effect in the test subject or group of test subjects, comparing the effect in the test subjects to an effect in a control group, and identifying the composition as useful if the allergic effect in the test subject or group of test subjects is less than the allergic effect in the control subject or group of control subjects. In some embodiments, the allergen is a food antigen. In some embodiments, the allergic effect is selected from the group consisting of plasma histamine level, serum antigen-specific IgE level, serum antigen-specific IgA level, serum antigen-specific IgG2a level, serum IL-1 beta (IL-1β) level, serum IL-1ra level, serum IL-2 level, serum IL-4 level, serum IL-5 level, serum IL-6 level, serum IL-7 level, serum IL-9 level, serum IL-10 level, serum IL-12 (p70) level, serum IL-13 level, serum IL-15 level, serum IL-17 level, interferon-gamma (IFN-γ) level, tumor necrosis factor-alpha (TNFα) level, tumor growth factor (TGF-β) level, Th17 cell activity, gut permeability and specific regulatory T cell infiltration into the small intestine and/or colon. In some embodiments, the allergic effect is allergen-specific IgE production, or airway hyperresponsiveness. In some embodiments, the test and control subjects are gnotobiotic subjects.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 1 is Table 1, a table with taxonomic families of the Keystone Operational Units (OTUS).

FIG. 2 is Table 2, with a list on non-Keystone Operational Units (OTUS).

FIG. 3 is Table 3, with a list on Keystone Genera and Taxonomic Families.

Figure 4:
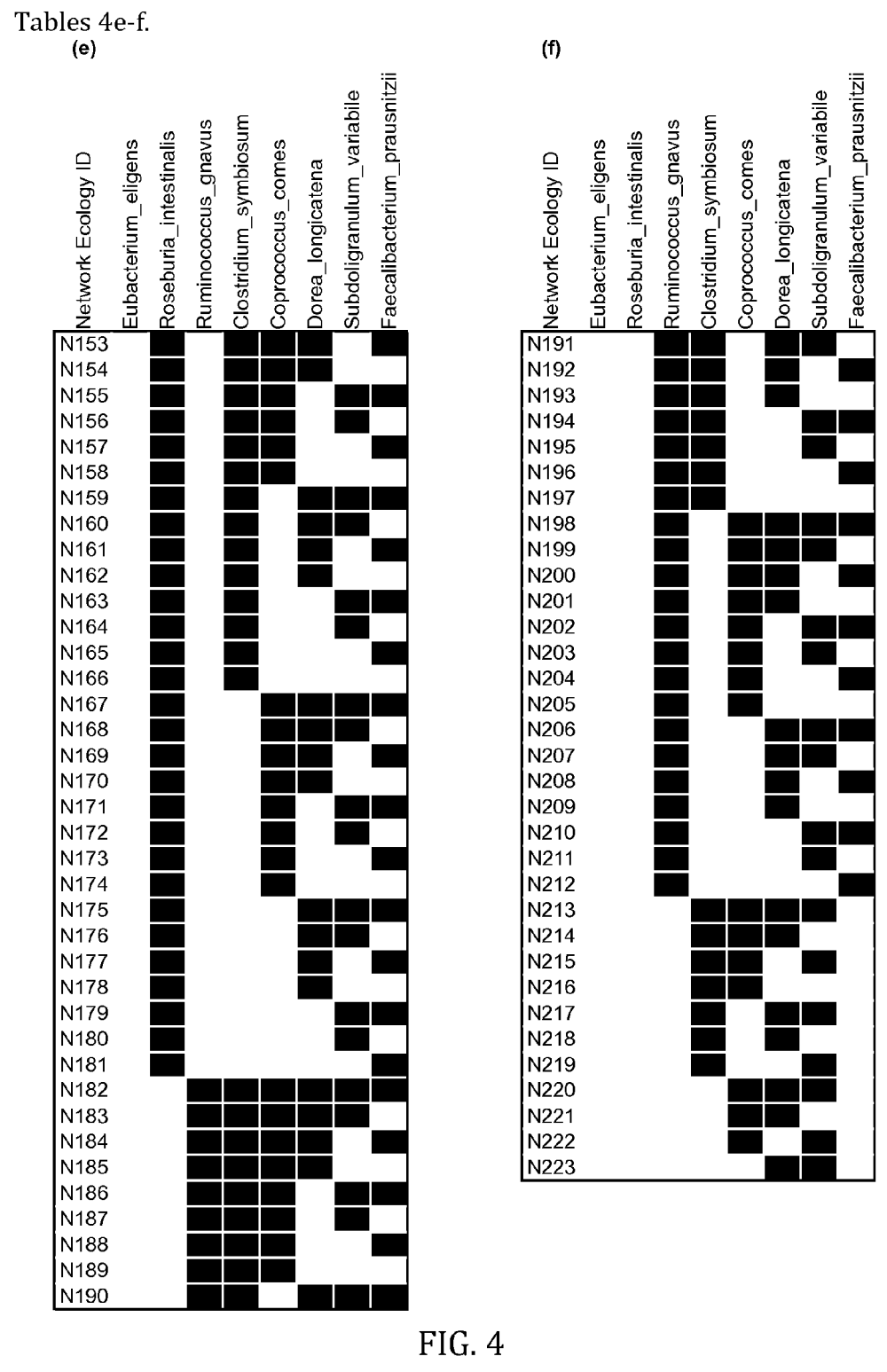

FIG. 4 is Table 4a, 4b, 4c, 4d, 4e, and 4f, illustrating Exemplary Functional Network Ecologies that are found only in healthy individuals, that contain only Keystone OTUs, that have OTUs with the functional capacity to form spores.

FIG. 5 is Table 5a, 5b, and 5c, illustrating Exemplary Core Network Ecologies defined from their occurrence in only healthy individuals, the size of the network, and the frequency of occurrence of the networks in individual subjects at or above the 90th percentile for the latter two metrics. OTUs represent diverse taxonomic families. Numbers in each cell represent the percentage of individual observed Network Ecologies within a given core that contain the given OTU. (a) OTUs that are observed in at least 80% of a core's networks (dark grey) are primary signature OTUs of a given core. (b-c) OTUs observed in 11%-79% (mid grey)≤10% (light grey) are secondary and tertiary signature OTUs respectively of a given Core Network. Primary signature OTUs are of greater significance than secondary signature OTUs which are of greater significance than tertiary keystone OTUs.

Figure 6:
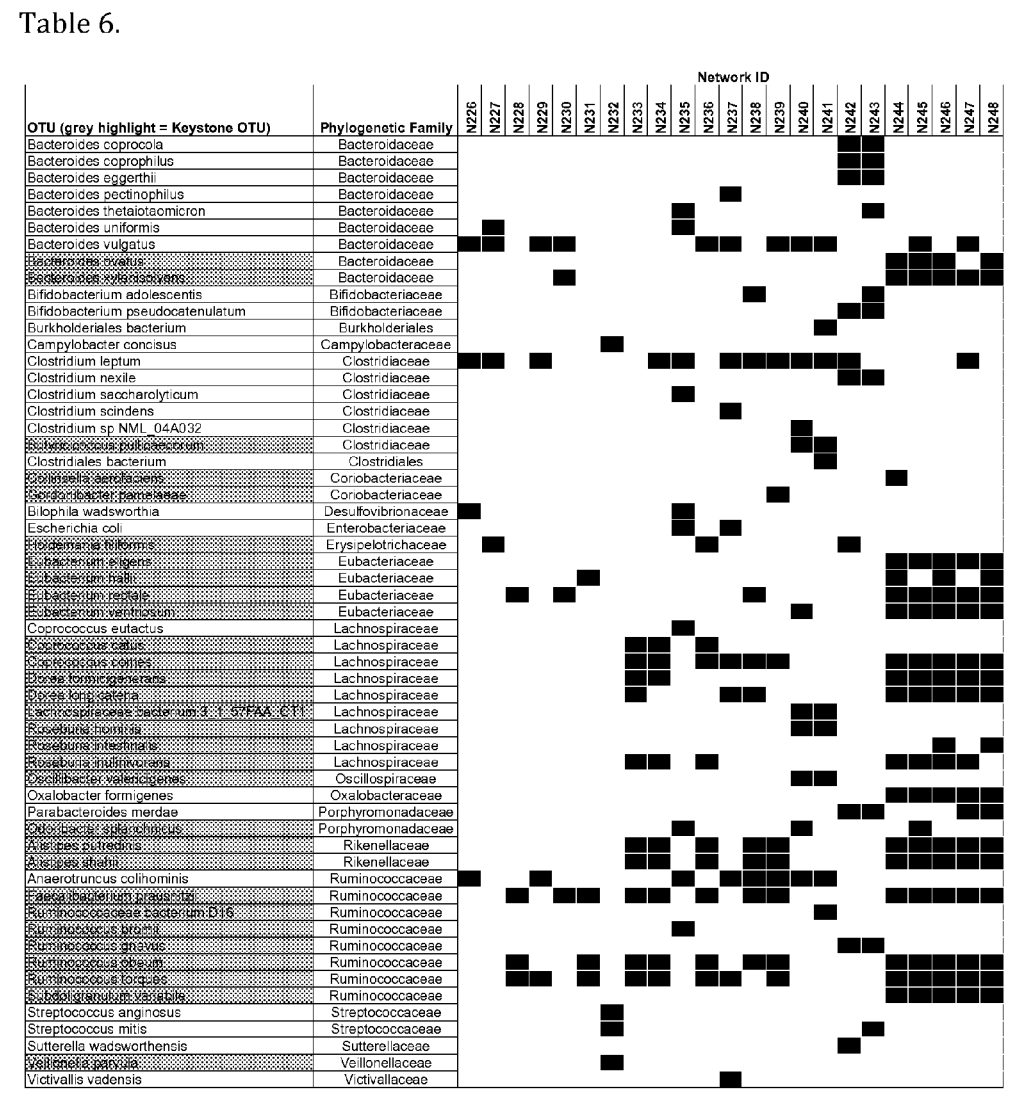

FIG. 6 is Table 6, illustrating. Exemplary Selected Networks Ecologies characterized by: (i) presence in only healthy individuals, (ii) specific network sizes, (iii) high frequency of occurrence across individual subject populations, and (iv) phylogenetic diversity.

FIG. 7 is Table 7, illustrating exemplary phylogenetic clades and OTUs.

FIG. 8 is Table 8a and Table 8b, that provide ranked lists in order of prevalence of bacterial OTUs at the taxonomic resolution of Family (8a) and Genera (8b) for a cohort of clinically qualified donors (n=7; 5-16 samples per donor). Bacteria were detected by sequencing of 16S as described herein.

DETAILED DESCRIPTION

Described herein are preparations comprising isolated bacterial compositions and methods of treating, preventing, or inhibiting immune system disorders, diseases and symptoms such as autoimmune diseases, inflammatory diseases, and allergic diseases. Accordingly, provided are pharmaceutical and nutritional preparations comprising bacterial compositions suitable for beneficial consumption by humans, other mammals, and other vertebrates (herein termed a "subject," "consumer" or multiple "consumers"). As described in more details below, such preparations contain a pharmaceutically-acceptable carrier, typically a solid, semi-solid, gel, liquid, or other form suitable for oral consumption, and at least one bacterial population. In some embodiments, the bacterial population contains effective amounts of one bacterial entity (e.g., a species, strain, clade or OTU), in other embodiments, it contains effective amounts of two or more distinct bacterial entities. In some embodiments, the bacterial population contains non-lactic acid-producing bacteria. In some embodiments the preparation includes least one OTU, e.g., species, strain or clade of a spore, or spore-forming bacteria as described in the Table 1, Table 3, Table 4, Table 7 and/or Table 8 and/or are derived from known network ecologies, e.g., core network ecologies as exemplified in Tables 4, 5a-c, and 6.

Definitions

"Microbiota" refers to the community of microrganisms that occur (sustainably or transiently) in and on an animal subject, typically a mammal such as a human, including eukaryotes, archaea, bacteria, and viruses (including bacterial viruses, i.e., phage).

"Microbiome" refers to the genetic content of the communities of microbes that live in and on the human body, both sustainably and transiently, including eukaryotes, archaea, bacteria, and viruses (including bacterial viruses (i.e., phage)), wherein "genetic content" includes genomic DNA, RNA such as ribosomal RNA, the epigenome, plasmids, and all other types of genetic information.

The terms "pathogen" and "pathogenic" in reference to a bacterium or any other organism or entity includes any such organism or entity that is capable of causing or affecting a disease, disorder or condition of a host organism containing the organism or entity, while a "pathobiont" includes a bacterium or other organism that, when the ecology of which is perturbed, is capable of causing or affecting a disease, disorder or condition of a host organism containing the organism or entity; for example, pathobionts include symbiotic organisms able to cause disease only when certain genetic and/or environmental conditions are present in a subject, or the shift to an ecological network that no longer provides a beneficial function to the host and therefore no longer promotes health.

A "sporulation induction agent" is a material or condition that is capable of inducing sporulation in a bacterium, either directly or indirectly, in a host organism and/or in vitro.

To "increase production of bacterial spores" includes an activity or a sporulation induction agent. "Production" includes conversion of vegetative bacterial cells into spores and augmentation of the rate of such conversion, as well as decreasing the germination of bacteria in spore form.

"Dysbiosis" refers to a state of the microbiota or microbiome of the gut or other body area, including mucosal or skin surfaces in which the normal diversity and/or function of the ecological network is disrupted. Any disruption from a healthy (e.g., ideal) state of the microbiota can be considered a dysbiosis, even if such dysbiosis does not result in a detectable decrease in health. A state of dysbiosis may be unhealthy, it may be unhealthy under only certain conditions, or it may prevent a subject from becoming healthier. Dysbiosis be due to, for example, a decrease in diversity or the overgrowth of one or more pathogens or pathobionts.

"Phylogenetic tree" refers to a graphical representation of the evolutionary relationships of one genetic sequence to another that is generated using a defined set of phylogenetic reconstruction algorithms (e.g., parsimony, maximum likelihood, or Bayesian). Nodes in the tree represent distinct ancestral sequences and the confidence of any node is provided by a bootstrap or Bayesian posterior probability, which measures of branch uncertainty.

"Operational taxonomic unit," "OTU" (or plural, "OTUs") refer to a terminal leaf in a phylogenetic tree and is defined by a nucleic acid sequence, e.g., the entire genome, or a specific genetic sequence, and all sequences that share sequence identity to this nucleic acid sequence at the level of species. In some embodiments the specific genetic sequence may be the 16S sequence or a portion of the 16S sequence. In other embodiments, the entire genomes of two entities are sequenced and compared. In another embodiment, select regions such as multilocus sequence tags (MLST), specific genes, or sets of genes may be genetically compared. In 16S embodiments, OTUs that share≥97% average nucleotide identity across the entire 16S or some variable region of the 16S are considered the same OTU (see, e.g., Claesson et al., 2010, Comparison of two next-generation sequencing technologies for resolving highly complex microbiota composition using tandem variable 16S rRNA gene regions. Nucleic Acids Res 38:e200; Konstantinidis et al., 2006. The bacterial species definition in the genomic era. Philos Trans R Soc Lond B Biol Sci 361:1929-1940). In embodiments involving the complete genome, MLSTs, specific genes, or sets of genes OTUs that share≥95% average nucleotide identity are considered the same OTU (see, e.g., Achtman and Wagner. 2008. Microbial diversity and the genetic nature of microbial species. *Nat. Rev. Microbiol.* 6: 431-440; Konstantinidis et al., 2006. supra). OTUs are in some cases defined by comparing sequences between organisms. Generally, sequences with less than 95% sequence identity are not considered to form part of the same OTU. OTUs may also be characterized by any combination of nucleotide markers or genes, in particular highly conserved genes (e.g., "house-keeping" genes), or a combination thereof. Such characterization employs, e.g., WGS data or a whole genome sequence.

In microbiology, "16S sequencing" or "16S-rRNA" or "16S" refers to sequence derived by characterizing the nucleotides that comprise the 16S ribosomal RNA gene(s). The bacterial 16S rDNA is approximately 1500 nucleotides in length and is used in reconstructing the evolutionary relationships and sequence similarity of one bacterial isolate to another using phylogenetic approaches. 16S sequences are used for phylogenetic reconstruction as they are in general highly conserved, but contain specific hypervariable regions that harbor sufficient nucleotide diversity to differentiate genera and species of most bacteria, as well as fungi.

The term "subject" refers to any animal subject including a human, laboratory animal (e.g., non-human primate, rat, mouse, hamster, guinea pig), livestock (e.g., cow, sheep, goat, pig, turkey, and chicken), and a household pet species (e.g., dog, cat, and rodent). The subject may be suffering from a dysbiosis, including, but not limited to, an infection due to a gastrointestinal pathogen or may be at risk of developing or transmitting to others an infection due to a gastrointestinal pathogen. In some embodiments, the subject has an immune-related disorder, for example, asthma or allergy, e.g., severe allergy The term "network ecology" refers to a consortium of OTUs that co-occur in multiple subjects. As used herein, a "network" is defined mathematically by a graph delineating how specific nodes (i.e., OTUs) and edges (connections between specific OTUs) relate to one another to define the structural ecology of a consortium of OTUs. Any given network ecology will possess inherent phylogenetic diversity and functional properties.

The term "Keystone OTU" refers to one or more OTUs that are common to many network ecologies and are members of networks ecologies that occur in many subjects (i.e., are pervasive). Keystone organisms and associated keystone functional pathways represent components of a microbial ecology that are central to maintaining a healthy metabolic and immunological state in an individual. Keystone OTUs are central to the function of network ecologies in healthy subjects and are often missing or at reduced levels in subjects with disease. Keystone OTUs and functions may exist in low, moderate, or high abundance in subjects.

A bacterial population that is "directly isolated from a fecal material" does not result from any culturing or other process that results in or is intended to result in replication of the population after obtaining the fecal material.

The term "non-Keystone OTU" refers to an OTU that is observed in a network ecology and is not a keystone OTU.

The term "phylogenetic diversity" refers to the biodiversity present in a given network ecology or core network ecology based on the OTUs that comprise the network. Phylogenetic diversity is a relative term, meaning that a network ecology or core network ecology that is comparatively more phylogenetically diverse than another network contains a greater number of unique species, genera, and taxonomic families. Uniqueness of a species, genera, or taxonomic family is generally defined using a phylogenetic tree that represents the genetic diversity all species, genera, or taxonomic families relative to one another. In another embodiment phylogenetic diversity can be measured using the total branch length or average branch length of a phylogenetic tree.

The term "phylogenetic tree" refers to a graphical representation of the evolutionary relationships of one genetic sequence to another that is generated using one or multiple defined phylogenetic reconstruction algorithms (e.g., parsimony, maximum likelihood, or Bayesian). Nodes in the tree represent distinct ancestral sequences and the confidence measure of any node is determined, e.g., by a bootstrap or Bayesian posterior probability, which measures of branch uncertainty.

The term "test composition" refers to a composition employed in an experimental protocol to determine a presence, absence and/or magnitude of an effect on a measured experimental parameter or outcome. The presence, absence and/or magnitude of the effect can be determined by comparing results obtained using the test composition with those obtained using a control composition.

Compositions Comprising Isolated Bacterial Populations

Described herein are preparations comprising at least a first isolated bacterial population for treating, preventing or reducing the severity of at least one sign and/or symptom associated with an immune system disorder in a human subject. Example immune system disorders are described in more detail below and include but are not limited to hypersensitivity immune disorder, an allergic disorder, a food allergy disorder, allergic conjunctivitis, allergic rhinitis, asthma, atopic dermatitis, atopic/allergic sensitivity, eosinophilic esophagitis, extrinsic allergic alveolitis, food allergy, perennial allergic rhinitis, seasonal allergic rhinitis, skin allergy, asthma or an asthma-related condition.

In some embodiments, the first bacterial population is capable of spore formation. In some embodiments, spore formation is defined as capable of growth under normal conditions after incubation in 70% ethanol for one hour.

In some embodiments, the first isolated bacterial population comprises *Clostridium absonum, Clostridium argentinense, Clostridium baratii, Clostridium bifermentans, Clostridium botulinum, Clostridium butyricum, Clostridium cadaveris, Clostridium camis, Clostridium celatum, Clostridium chauvoei, Clostridium clostridioforme, Clostridium cochlearium, Clostridium difficile, Clostridium fallax, Clostridium felsineum, Clostridium ghonii, Clostridium glycolicum, Clostridium haemolyticum, Clostridium hastiforme, Clostridium histolyticum, Clostridium indolis, Clostridium innocuum, Clostridium irregulare, Clostridium limosum, Clostridium malenominatum, Clostridium novyi, Clostridium oroticum, Clostridium paraputrificum, Clostridium perfringens, Clostridium piliforme, Clostridium putrefaciens, Clostridium putrificum, Clostridium ramosum, Clostridium sardiniense, Clostridium sartagoforme, Clostridium scindens, Clostridium septicum, Clostridium sordellii, Clostridium sphenoides, Clostridium spiroforme, Clostridium sporogenes, Clostridium subterminale, Clostridium symbiosum, Clostridium tertium, Clostridium tetani, Clostridium welchii,* or *Clostridium villosum.*

In some embodiments, the first bacterial population is selected from the OTUs found in Table 1 or Table 2, or an OTU from the taxonomic Family or Genera found in Table 3. In some embodiments, the first bacterial population is selected from OTUs described in known network ecologies, e.g., those exemplified in Table 4, Table 5a, Table 5b, Table 5c, and Table 6. In some embodiments, the first bacterial population includes a complete network ecology, e.g., those exemplified in Table 4, Table 5a, Table 5b, Table 5c, and Table 6.

As used herein, a "type" or more than one "types" of bacteria may be differentiated at the genus level, the species, level, the sub-species level, the strain level or by any other taxonomic method, as described herein and otherwise known in the art. Bacterial compositions may contain at least two types of these exemplary bacteria, including strains of the same species. For instance, a bacterial composition may comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 or more than 20 types of bacteria, as defined by above species or operational taxonomic unit (OTU) encompassing such species. Bacterial compositions may consist essentially of no greater than a number of types of these bacteria. For instance, a bacterial composition may comprise no more than 2, no more than 3, no more than 4, no more than 5, no more than 6, no more than 7, no more than 8, no more than 9, no more than 10, no more than 11, no more than 12, no more than 13, no more than 14, no more than 15, no more than 16, no more than 17, no more than 18, no more than 19, or no more than 20 types of bacteria, as defined by above species or operational taxonomic unit (OTU) encompassing such species. Bacterial compositions may consist essentially of a range of numbers of species of these bacteria, but the precise number of species in a given composition is not known. For instance, a bacterial composition may consist essentially of between 2 and 10, 3 and 10, 4 and 10, 5 and 10, 6 and 10, 7 and 10, 8 and 10, or 9 and 10; or 2 and 9, 3 and 9, 4 and 9, 5 and 9, 6 and 9, 7 and 8 or 8 and 9; or 2 and 8, 3 and 8, 4 and 8, 5 and 8, 6 and 8 or 7 and 8; or 2 and 7, 3 and 7, 4 and 7, 5 and 7, or 6 and 7; or 2 and 6, 3 and 6, 4 and 6 or 5 and 6; or 2 and 5, 3 and 5 or 4 and 5; or 2 and 4 or 3 and 4; or 2 and 3, as defined by above species or operational taxonomic unit (OTU) encompassing such species. Bacterial compositions containing a plurality of species may be provided such that the relative concentration of a given species in the composition to any other species in the composition is known or unknown. Such relative concentrations of any two species, or OTUs, may be expressed as a ratio, where the ratio of a first species or OTU to a second species or OTU is 1:1 or any ratio other than 1:1, such as 1:2, 1:3, 1:4, 1:5, 1:6, 1:7, 1:8, 1:9, 1:10, 1:15, 1:20, 1:25; 1:50; 1:75, 1:100, 1:200, 1:500; 1:1000, 1:10,000, 1:100,000 or greater than 1:100,000. The ratio of bacterial OTUs present in a bacterial composition may be determined by the ratio of the bacterial OTUs in a reference mammalian subject, e.g., a healthy human not suffering from or at known risk of developing a dysbiosis.

In embodiments, the bacterial populations contain combinations of at least two distinct species, strains or OTUs. For example, bacterial compositions include 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more than 50 bacterial entities provided below.

In some embodiments, the composition comprises or consists essentially of species selected from the group consisting of *Akkermansia muciniphila, Alistipes putredinis, Alistipes shahii, Alkaliphilus metalliredigenes, Alkaliphilus oremlandii, Anaerococcus hydrogenalis, Anaerofustis stercorihominis, Anaerotruncus colihominis, Bacillus alcalophilus, Bacillus cereus, Bacillus circulans, Bacteroides cellulosilyticus, Bacteroides coprocola, Bacteroides coprophilus, Bacteroides dorei, Bacteroides finegoldii, Bacteroides intestinalis, Bacteroides pectinophilus, Bacteroides plebeius, Bacteroides xylanisolvens, Bifidobacterium catenulatum, Bifidobacterium pseudocatenulatum, Bilophila wadsworthia, Blautia hansenii, Blautia hydrogenotrophica, Blautia luti, Blautia wexlerae, Bryantella formatexigens, Butyrivibrio fibrisolvens, Campylobacter concisus, Campylobacter curvus, Catenibacterium mitsuokai, Clostridium asparagiforme, Clostridium bartlettii, Clostridium bolteae, Clostridium citroniae, Clostridium hathewayi, Clostridium hiranonis, Clostridium hylemonae, Clostridium lavalense, Clostridium methylpentosum, Clostridium nexile, Clostridium orbiscindens, Clostridium saccharolyticum, Clostridium sticklandii, Dorea formicigenerans, Dorea longicatena, Eubacterium dolichum, Eubacterium yurii, Filifactor alocis, Finegoldia magna, Flavonifractor plautii, Holdemania filiformis, Lactobacillus amylolyticus, Lactobacillus gasseri, Lactobacillus johnsonii, Lactobacillus salivarius, Odoribacter laneus, Odoribacter splanchnicus, Oxalobacter formigenes, Parabacteroides johnsonii, Parabacteroides merdae, Parasutterella excrementihominis, Parvimonas micra, Peptostreptococcus anaerobius, Peptostreptococcus stomatis, Prevotella copri, Prevotella oralis, Prevotella salivae, Pseudoflavonifractor capillosus, Roseburia inulinivorans, Ruminococcus gnavus, Shigella flexneri, Staphylococcus aureus, Streptococcus anginosus, Streptococcus salivarius, Streptococcus thermophilus, Subdoligranulum variabile, Sutterella wadsworthensis,* and *Veillonella parvula.*

In some embodiments, the composition comprises or consists essentially of species selected from the group consisting of *Acidaminococcus intestinalis, Adlercreutzia equolifaciens, Akkermansia muciniphila, Alistipes putredinis, Alistipes shahii, Alkaliphilus metalliredigenes, Alkaliphilus oremlandii, Anaerococcus hydrogenalis, Anaerofustis stercorihominis, Anaerostipes caccae, Anaerotruncus colihominis, Bacillus alcalophilus, Bacillus cereus, Bacillus circulans, Bacteroides caccae, Bacteroides cellulosilyticus, Bacteroides coprocola, Bacteroides coprophilus, Bacteroides dorei, Bacteroides eggerthii, Bacteroides finegoldii, Bacteroides fragilis, Bacteroides intestinalis, Bacteroides ovatus, Bacteroides pectinophilus, Bacteroides plebeius, Bacteroides stercoris, Bacteroides thetaiotaomicron, Bacteroides uniformis, Bacteroides vulgatus, Bacteroides xylanisolvens, Barnesiella intestinihominis, Bifidobacterium adolescentis, Bifidobacterium catenulatum, Bifidobacterium longum, Bifidobacterium pseudocatenulatum, Bilophila wadsworthia, Blautia hansenii, Blautia hydrogenotrophica, Blautia luti, Blautia producta, Blautia wexlerae, Bryantella formatexigens, Butyrivibrio crossotus, Butyrivibrio fibrisolvens, Campylobacter concisus, Campylobacter curvus, Catenibacterium mitsuokai, Clostridium asparagiforme, Clostridium bartlettii, Clostridium bifermentans, Clostridium bolteae, Clostridium celatum, Clostridium citroniae, Clostridium clostridioforme, Clostridium hathewayi, Clostridium hiranonis, Clostridium hylemonae, Clostridium indolis, Clostridium innocuum, Clostridium lavalense, Clostridium leptum, Clostridium methylpentosum, Clostridium nexile, Clostridium orbiscindens, Clostridium perfringens, Clostridium ramosum, Clostridium saccharolyticum, Clostridium scindens, Clostridium sordellii, Clostridium sp, Clostridium spiroforme, Clostridium sporogenes, Clostridium sticklandii, Clostridium symbiosum, Clostridium tetani, Collinsella aerofaciens, Coprococcus catus, Coprococcus comes, Coprococcus eutactus, Desulfovibrio piger, Dorea formicigenerans, Dorea longicatena, Enterococcus durans, Enterococcus faecalis, Enterococcus faecium, Enterococcus hirae, Escherichia coli, Eubacterium biforme, Eubacterium cylindroides, Eubacterium dolichum, Eubacterium eligens, Eubacterium hadrum, Eubacterium hallii, Eubacterium limosum, Eubacterium rectale, Eubacterium siraeum, Eubacterium ventriosum, Eubacterium yurii, Faecalibacterium prausnitzii, Filifactor alocis, Fine-* goldia magna, Flavonifractor plautii, Holdemania filiformis, Lactobacillus amylolyticus, Lactobacillus casei, Lactobacillus gasseri, Lactobacillus johnsonii, Lactobacillus paracasei, Lactobacillus reuteri, Lactobacillus salivarius, Odoribacter laneus, Odoribacter splanchnicus, Oxalobacter formigenes, Parabacteroides distasonis, Parabacteroides johnsonii, Parabacteroides merdae, Parasutterella excrementihominis, Parvimonas micra, Peptostreptococcus anaerobius, Peptostreptococcus stomatis, Prevotella copri, Prevotella oralis, Prevotella salivae, Pseudoflavonifractor capillosus, Roseburia faecis, Roseburia intestinalis, Roseburia inulinivorans, Ruminococcus bromii, Ruminococcus gnavus, Ruminococcus lactaris, Ruminococcus obeum, Ruminococcus torques, Shigella flexneri, Staphylococcus aureus, Staphylococcus pasteuri, Staphylococcus warneri, Streptococcus anginosus, Streptococcus mitis, Streptococcus salivarius, Streptococcus thermophilus, Subdoligranulum variabile, Sutterella wadsworthensis, and Veillonella parvula.

In some embodiments, the composition comprises or consists essentially of species selected from the group consisting of Acidaminococcus intestinalis, Adlercreutzia equolifaciens, Anaerostipes caccae, Bacteroides ovatus, Bacteroides thetaiotaomicron, Bacteroides vulgatus, Barnesiella intestinihominis, Bifidobacterium adolescentis, Bifidobacterium longum, Blautia producta, Clostridium bifermentans, Clostridium indolis, Clostridium innocuum, Clostridium ramosum, Collinsella aerofaciens, Dorea longicatena, Enterococcus durans, Enterococcus faecalis, Enterococcus faecium, Enterococcus hirae, Escherichia coli, Eubacterium eligens, Eubacterium limosum, Eubacterium rectale, Eubacterium ventriosum, Faecalibacterium prausnitzii, Lactobacillus casei, Lactobacillus paracasei, Lactobacillus reuteri, Parabacteroides distasonis, Roseburia faecis, Roseburia intestinalis, Ruminococcus torques, Staphylococcus pasteuri, Staphylococcus warneri, and Streptococcus mitis.

In some embodiments, the composition comprises or consists essentially of species selected from the group consisting of Bacteroides ovatus, Bacteroides thetaiotaomicron, Bacteroides vulgatus, Blautia producta, Clostridium bifermentans, Clostridium innocuum, Clostridium ramosum, Enterococcus faecalis, and Escherichia coli.

In some embodiments, the composition comprises or consists essentially of species selected from the group consisting of Acidaminococcus intestinalis, Bacteroides ovatus, Bifidobacterium adolescentis, Bifidobacterium longum, Collinsella aerofaciens, Dorea longicatena, Escherichia coli, Eubacterium eligens, Eubacterium limosum, Eubacterium rectale, Eubacterium ventriosum, Faecalibacterium prausnitzii, Lactobacillus casei, Lactobacillus paracasei, Parabacteroides distasonis, Roseburia faecis, Roseburia intestinalis, Ruminococcus torques, and Streptococcus mitis.

In some embodiments, the composition comprises or consists essentially of species selected from the group consisting of Adlercreutzia equolifaciens, Anaerostipes caccae, Barnesiella intestinihominis, Clostridium indolis, Enterococcus durans, Enterococcus faecium, Enterococcus hirae, Lactobacillus reuteri, Staphylococcus pasteuri, and Staphylococcus warneri.

In some embodiments, the composition comprises or consists essentially of species selected from the group consisting of Anaerostipes caccae, Anaerotruncus colihominis, Bacteroides uniformis, Barnesiella intestinihominis, Bryantella formatexigens, Butyrivibrio crossotus, Clostridium bolteae, Clostridium clostridioforme, Clostridium methylpentosum, Clostridium orbiscindens, Clostridium scindens, Coprococcus catus, Desulfovibrio piger, Enterococcus faecalis, Enterococcus hirae, Escherichia coli, Lactobacillus amylolyticus, Lactobacillus gasseri, Lactobacillus johnsonii, Lactobacillus reuteri, Lactobacillus salivarius, Odoribacter laneus, Odoribacter splanchnicus, Parabacteroides distasonis, Parasutterella excrementihominis, Prevotella oralis, Roseburia intestinalis, Ruminococcus lactaris, and Shigella flexneri.

In some embodiments, the composition comprises or consists essentially of species selected from the group consisting of Alkaliphilus metalliredigenes, Alkaliphilus oremlandii, Anaerococcus hydrogenalis, Anaerofustis stercorihominis, Anaerostipes caccae, Anaerotruncus colihominis, Bacillus alcalophilus, Bacillus cereus, Bacillus circulans, Blautia hansenii, Blautia hydrogenotrophica, Blautia luti, Blautia producta, Blautia wexlerae, Bryantella formatexigens, Butyrivibrio crossotus, Butyrivibrio fibrisolvens, Clostridium asparagiforme, Clostridium bartlettii, Clostridium bifermentans, Clostridium bolteae, Clostridium celatum, Clostridium citroniae, Clostridium clostridioforme, Clostridium hathewayi, Clostridium hiranonis, Clostridium hylemonae, Clostridium innocuum, Clostridium lavalense, Clostridium leptum, Clostridium methylpentosum, Clostridium nexile, Clostridium perfringens, Clostridium ramosum, Clostridium saccharolyticum, Clostridium scindens, Clostridium sordellii, Clostridium sp, Clostridium spiroforme, Clostridium sporogenes, Clostridium sticklandii, Clostridium symbiosum, Clostridium tetani, Coprococcus catus, Coprococcus comes, Coprococcus eutactus, Dorea formicigenerans, Dorea longicatena, Eubacterium biforme, Eubacterium cylindroides, Eubacterium dolichum, Eubacterium eligens, Eubacterium hadrum, Eubacterium hallii, Eubacterium limosum, Eubacterium rectale, Eubacterium siraeum, Eubacterium ventriosum, Eubacterium yurii, Faecalibacterium prausnitzii, Filifactor alocis, Finegoldia magna, Flavonifractor plautii, Oxalobacter formigenes, Parvimonas micra, Peptostreptococcus anaerobius, Peptostreptococcus stomatis, Pseudoflavonifractor capillosus, Roseburia faecis, Roseburia intestinalis, Roseburia inulinivorans, Ruminococcus bromii, and Subdoligranulum variabile.

In some embodiments, the composition comprises or consists essentially of species selected from the group consisting of Akkermansia muciniphila, Alistipes putredinis, Alistipes shahii, Anaerotruncus colihominis, Bacteroides caccae, Bacteroides cellulosilyticus, Bacteroides coprocola, Bacteroides coprophilus, Bacteroides dorei, Bacteroides eggerthii, Bacteroides finegoldii, Bacteroides fragilis, Bacteroides intestinalis, Bacteroides ovatus, Bacteroides pectinophilus, Bacteroides plebeius, Bacteroides stercoris, Bacteroides thetaiotaomicron, Bacteroides uniformis, Bacteroides vulgatus, Bacteroides xylanisolvens, Bifidobacterium adolescentis, Bifidobacterium catenulatum, Bifidobacterium longum, Bifidobacterium pseudocatenulatum, Bilophila wadsworthia, Blautia hansenii, Butyrivibrio crossotus, Campylobacter concisus, Campylobacter curvus, Catenibacterium mitsuokai, Clostridium asparagiforme, Clostridium bartlettii, Clostridium bolteae, Clostridium leptum, Clostridium methylpentosum, Clostridium nexile, Clostridium scindens, Collinsella aerofaciens, Coprococcus comes, Coprococcus eutactus, Dorea formicigenerans, Dorea longicatena, Enterococcus faecalis, Escherichia coli, Eubacterium biforme, Eubacterium eligens, Eubacterium hallii, Eubacterium rectale, Eubacterium siraeum, Eubacterium ventriosum, Faecalibacterium prausnitzii, Holdemania filiformis, Lactobacillus gasseri, Odoribacter splanchnicus, *Parabacteroides distasonis, Parabacteroides johnsonii, Parabacteroides merdae, Prevotella copri, Prevotella salivae, Pseudoflavonifractor capillosus, Roseburia intestinalis, Roseburia inulinivorans, Ruminococcus bromii, Ruminococcus gnavus, Ruminococcus lactaris, Ruminococcus obeum, Ruminococcus torques, Staphylococcus aureus, Streptococcus anginosus, Streptococcus mitis, Streptococcus salivarius, Streptococcus thermophilus, Subdoligranulum variabile, Sutterella wadsworthensis*, and *Veillonella parvula*.

In some embodiments, the composition comprises or consists essentially of species selected from the group consisting of *Acidaminococcus intestinalis, Bacillus coagulans, Bacillus licheniformis, Bacillus subtilis, Bifidobacterium adolescentis, Bifidobacterium animalis, Bifidobacterium bifidum, Bifidobacterium breve, Bifidobacterium infantis, Bifidobacterium longum, Clostridium butyricum, Enterococcus faecalis, Enterococcus faecium, Escherichia coli, Lactobacillus acidophilus, Lactobacillus brevis, Lactobacillus bulgaricus, Lactobacillus casei, Lactobacillus fermentum, Lactobacillus gasseri, Lactobacillus helveticus, Lactobacillus paracasei, Lactobacillus plantarum, Lactobacillus reuteri, Lactobacillus rhamnosus, Lactobacillus salivarius, Lactococcus lactis, Pediococcus acidilactici*, and *Streptococcus thermophiles*.

In some embodiments, the composition comprises or consists essentially of species selected from the group consisting of *Bacillus amyloliquefaciens, Bacillus licheniformis, Bacillus pumilis, Bacillus subtilis, Bifidobacterium animalis, Bifidobacterium bifidum, Bifidobacterium longum, Bifidobacterium thermophilum, Enterococcus faecalis, Enterococcus faecium, Lactobacillus acidophilus, Lactobacillus brevis, Lactobacillus bulgaricus, Lactobacillus casei, Lactobacillus plantarum, Lactococcus lactis, Pediococcus acidilactici, Pediococcus pentosaceus, Propionibacterium freudenreichii*, and *Rhodopseudomonas palustris*.

In some embodiments, the composition does not include at least one species selected from a group as detected by assays well known to one of skill in the art, e.g., 16S sequencing. The group includes the following species: *Bacillus anthracis, Clostridium botulinum, Francisella tularensis, Yersinia pestis, Brucella abortus, Brucella canis, Brucella ceti, Brucella melitensis, Brucella microti, Brucella ovis, Brucella* sp. 83/13, *Brucella* sp. BO1, *Brucella suis, Burkholderia mallei, Burkholderia pseudomallei, Campylobacter jejuni, Chlamydia psittaci, Clostridium perfringens, Coxiella burnetii, Escherichia coli, Listeria monocytogenes, Rickettsia prowazekii, Salmonella bongori, Salmonella enterica, Salmonella typhimurium, Shigella boydii, Shigella dysenteriae, Shigella flexneri, Shigella sonnei, Shigella* sp. D9, *Staphylococcus aureus, Vibrio cholerae, Vibrio fluvialis, Vibrio furnissii, Vibrio mimicus, Vibrio parahaemolyticus, Vibrio* sp. RC341, *Vibrio vulnificus, Yersinia enterocolitica, Mycobacterium tuberculosis, Bifidobacterium dentium, Bordetella bronchiseptica, Bordetella holmesii, Bordetella parapertussis, Bordetella pertussis, Borrelia afzelii, Borrelia burgdorferi, Borrelia crocidurae, Borrelia duttonii, Borrelia garinii, Borrelia hermsii, Borrelia hispanica, Borrelia persica, Borrelia recurrentis, Borrelia* sp. NE49, *Borrelia spielmanii, Borrelia turicatae, Borrelia valaisiana, Burkholderia ambifaria, Burkholderia cenocepacia, Burkholderia cepacia, Burkholderia multivorans, Burkholderia oklahomensis, Burkholderia rhizoxinica, Burkholderia* sp. 383, *Burkholderia xenovorans, Burkholderiales bacterium* 1_1_47, *Campylobacter coli, Campylobacter concisus, Campylobacter curvus, Campylobacter fetus, Campylobacter gracilis, Campylobacter hominis, Campylobacter lari, Campylobacter rectus, Campylobacter showae, Campylobacter* sp. FOBRC14, *Campylobacter* sp. FOBRC15, *Campylobacter* sp. oral clone BB120, *Campylobacter sputorum, Campylobacter upsaliensis, Chlamydia muridarum, Chlamydia trachomatis, Chlamydophila pecorum, Chlamydophila pneumoniae, Chlamydophila psittaci, Clostridium difficile, Corynebacterium amycolatum, Corynebacterium diphtheriae, Corynebacterium jeikeium, Corynebacterium striatum, Corynebacterium urealyticum, Corynebacterium xerosis, Ehrlichia chaffeensis, Haemophilus ducreyi, Haemophilus influenzae, Helicobacter pylori, Klebsiella oxytoca, Klebsiella pneumoniae, Legionella hackeliae, Legionella longbeachae, Legionella pneumophila, Legionella* sp. D3923, *Legionella* sp. D4088, *Legionella* sp. H63, *Legionella* sp. NML 93L054, *Legionella steelei, Leptospira borgpetersenii, Leptospira broomii, Leptospira interrogans, Leptospira licerasiae, Listeria grayi, Listeria welshimeri, Mycobacterium abscessus, Mycobacterium africanum, Mycobacterium alsiensis, Mycobacterium avium, Mycobacterium chelonae, Mycobacterium colombiense, Mycobacterium elephantis, Mycobacterium gordonae, Mycobacterium intracellulare, Mycobacterium kansasii, Mycobacterium lacus, Mycobacterium leprae, Mycobacterium lepromatosis, Mycobacterium mageritense, Mycobacterium mantenii, Mycobacterium marinum, Mycobacterium microti, Mycobacterium neoaurum, Mycobacterium parascrofulaceum, Mycobacterium paraterrae, Mycobacterium phlei, Mycobacterium seoulense, Mycobacterium smegmatis, Mycobacterium ulcerans, Mycobacterium vulneris, Neisseria gonorrhoeae, Neisseria meningitidis, Orientia tsutsugamushi, Rickettsia akari, Rickettsia conorii, Rickettsia rickettsii, Rickettsia slovaca, Rickettsia typhi, Streptococcus pyogenes, Treponema denticola, Treponema lecithinolyticum, Treponema pallidum, Treponema parvum, Treponema putidum, Treponema refringens, Treponema socranskii, Treponema vincentii, Yersinia aldovae, Yersinia aleksiciae, Yersinia bercovieri, Yersinia frederiksenii, Yersinia intermedia, Yersinia kristensenii, Yersinia mollaretii, Yersinia pseudotuberculosis, Yersinia rohdei, Abiotrophia defectiva, Acetivibrio ethanolgignens, Acinetobacter baumannii, Acinetobacter junii, Acinetobacter radioresistens, Aeromonas allosaccharophila, Aeromonas enteropelogenes, Aeromonas jandaei, Aeromonas trota, Alcaligenes faecalis, Alistipes putredinis, Anaerococcus prevotii, Anaerococcus vaginalis, Anaerostipes caccae, Arcobacter butzleri, Bacillus cereus, Bacteroides caccae, Bacteroides coagulans, Bacteroides coprocola, Bacteroides eggerthii, Bacteroides fragilis, Bacteroides helcogenes, Bacteroides massiliensis, Bacteroides nordii, Bacteroides ovatus, Bacteroides plebeius, Bacteroides pyogenes, Bacteroides salyersiae, Bacteroides stercoris, Bacteroides thetaiotaomicron, Bacteroides uniformis, Bacteroides ureolyticus, Bacteroides vulgatus, Bartonella quintana, Bilophila wadsworthia, Cedecea davisae, Citrobacter amalonaticus, Citrobacter braakii, Citrobacter farmeri, Citrobacter freundii, Citrobacter gillenii, Citrobacter koseri, Citrobacter murliniae, Citrobacter rodentium, Citrobacter sedlakii, Citrobacter* sp. 30_2, *Citrobacter* sp. KMSI-3, *Citrobacter werkmanii, Citrobacter youngae, Clostridium aldenense, Clostridium argentinense, Clostridium baratii, Clostridium bartlettii, Clostridium beijerinckii, Clostridium bifermentans, Clostridium bolteae, Clostridium butyricum, Clostridium cadaveris, Clostridium earths, Clostridium chauvoei, Clostridium citroniae, Clostridium clostridioforme, Clostridium colinum, Clostridium fallax, Clostridium ghonii, Clostridium glycolicum, Clostridium haemolyticum, Clostridium histolyticum, Clostridium indolis, Clostridium innocuum, Clostridium*

*limosum, Clostridium malenominatum, Clostridium novyi, Clostridium oroticum, Clostridium paraputrificum, Clostridium piliforme, Clostridium ramosum, Clostridium sardiniense, Clostridium septicum, Clostridium sordellii, Clostridium sphenoides, Clostridium sporogenes, Clostridium subterminale, Clostridium symbiosum, Clostridium tertium, Clostridium tetani, Collinsella aerofaciens, Corynebacterium accolens, Corynebacterium argentoratense, Corynebacterium bovis, Corynebacterium confusum, Corynebacterium coyleae, Corynebacterium falsenii, Corynebacterium glucuronolyticum, Corynebacterium imitans, Corynebacterium macginleyi, Corynebacterium mastitidis, Corynebacterium matruchotii, Corynebacterium minutissimum, Corynebacterium mucifaciens, Corynebacterium propinquum, Corynebacterium pseudodiphtheriticum, Corynebacterium pseudotuberculosis, Corynebacterium renale, Corynebacterium resistens, Corynebacterium riegelii, Corynebacterium simulans, Corynebacterium sundsvallense, Corynebacterium tuberculostearicum, Corynebacterium ulcerans, Cronobacter malonaticus, Cronobacter sakazakii, Cronobacter turicensis, Dialister invisus, Dialister micraerophilus, Dialister microaerophilus, Dialister pneumosintes, Dialister propionicifaciens, Edwardsiella tarda, Eggerthella lenta, Eggerthella sinensis, Eggerthella sp. 1_3_56FAA, Eggerthella sp. HGA1, Eggerthella sp. YY7918, Enterobacter aerogenes, Enterobacter asburiae, Enterobacter cancerogenus, Enterobacter cloacae, Enterobacter cowanii, Enterobacter hormaechei, Enterococcus avium, Enterococcus casseliflavus, Enterococcus durans, Enterococcus faecalis, Enterococcus faecium, Enterococcus gallinarum, Enterococcus hirae, Enterococcus raffinosus, Erysipelothrix rhusiopathiae, Erysipelothrix tonsillarum, Escherichia albertii, Escherichia fergusonii, Escherichia hermannii, Escherichia vulneris, Eubacterium brachy, Eubacterium contortum, Eubacterium infirmum, Eubacterium limosum, Eubacterium moniliforme, Eubacterium nitritogenes, Eubacterium nodatum, Eubacterium saphenum, Eubacterium tenue, Eubacterium tortuosum, Eubacterium ventriosum, Eubacterium yurii, Ewingella americana, Facklamia hominis, Faecalibacterium prausnitzii, Filifactor alocis, Finegoldia magna, Fusobacterium canifelinum, Fusobacterium gonidiaformans, Fusobacterium mortiferum, Fusobacterium naviforme, Fusobacterium necrogenes, Fusobacterium nucleatum, Fusobacterium periodonticum, Fusobacterium russii, Fusobacterium ulcerans, Fusobacterium varium, Gardnerella vaginalis, Gemella haemolysans, Gemella morbillorum, Gemella sanguinis, Gordonia bronchialis, Gordonia sputi, Gordonia terrae, Granulicatella adiacens, Granulicatella elegans, Grimontia hollisae, Haemophilus aegyptius, Haemophilus parahaemolyticus, Haemophilus parainfluenzae, Haemophilus paraphrophaemolyticus, Haemophilus parasuis, Hafnia alvei, Helicobacter bilis, Helicobacter canadensis, Helicobacter cinaedi, Helicobacter pullorum, Histophilus somni, Johnsonella ignava, Jonquetella anthropi, Kersteria gyiorum, Kingella denitrificans, Kingella kingae, Kingella oralis, Klebsiella sp. 1_1_55, Klebsiella sp. AS10, Klebsiella sp. Co9935, Klebsiella sp. enrichment culture clone SRC_DSD25, Klebsiella sp. MS 92-3, Klebsiella sp. OBRC7, Klebsiella sp. SP-BA, Klebsiella sp. SRC_DSD1, Klebsiella sp. SRC_DSD11, Klebsiella sp. SRC_DSD12, Klebsiella sp. SRC_DSD15, Klebsiella sp. SRC_DSD2, Klebsiella sp. SRC_DSD6, Klebsiella variicola, Kluyvera ascorbata, Kluyvera cryocrescens, Lactobacillus rhamnosus, Lactococcus garvieae, Laribacter hongkongensis, Leptotrichia buccalis, Listeria innocua, Listeria ivanovii, Macrococcus caseolyticus, Mannheimia haemolytica, Megasphaera elsdenii, Mitsuokella multacida, Mobiluncus curtisii, Mobiluncus mulieris, Moellerella wisconsensis, Mogibacterium neglectum, Mogibacterium pumilum, Mogibacterium timidum, Moraxella catarrhalis, Moraxella osloensis, Morganella morganii, Morococcus cerebrosus, Moryella indoligenes, Mycobacterium sp. 1761, Mycobacterium sp. 1776, Mycobacterium sp. 1781, Mycobacterium sp. 1791, Mycobacterium sp. 1797, Mycobacterium sp. AQ1GA4, Mycobacterium sp. B10-07.09.0206, Mycobacterium sp. GN-10546, Mycobacterium sp. GN-10827, Mycobacterium sp. GN-11124, Mycobacterium sp. GN-9188, Mycobacterium sp. GR-2007-210, Mycobacterium sp. HE5, Mycobacterium sp. NLA001000736, Mycobacterium sp. W, Mycoplasma agalactiae, Mycoplasma amphoriforme, Mycoplasma arthritidis, Mycoplasma bovoculi, Mycoplasma faucium, Mycoplasma fermentans, Mycoplasma flocculare, Mycoplasma genitalium, Mycoplasma hominis, Mycoplasma orale, Mycoplasma ovipneumoniae, Mycoplasma penetrans, Mycoplasma pneumoniae, Mycoplasma putrefaciens, Mycoplasma salivarium, Myroides odoratimimus, Neisseria bacilliformis, Neisseria elongata, Neisseria flavescens, Neisseria mucosa, Neisseria sicca, Neisseria subflava, Neorickettsia risticii, Neorickettsia sennetsu, Nocardia brasiliensis, Nocardia cyriacigeorgica, Nocardia farcinica, Nocardiopsis dassonvillei, Ochrobactrum anthropi, Ochrobactrum intermedium, Odoribacter splanchnicus, Olsenella profusa, Olsenella uli, Pantoea agglomerans, Parabacteroides distasonis, Parabacteroides goldsteinii, Parvimonas micra, Pasteurella bettyae, Pasteurella dagmatis, Pasteurella multocida, Peptococcus niger, Peptoniphilus asaccharolyticus, Peptoniphilus harei, Peptoniphilus indolicus, Peptoniphilus ivorii, Peptoniphilus lacrimalis, Peptostreptococcus stomatis, Photorhabdus asymbiotica, Plesiomonas shigelloides, Porphyromonas asaccharolytica, Porphyromonas endodontalis, Porphyromonas gingivalis, Porphyromonas levii, Porphyromonas macacae, Porphyromonas somerae, Porphyromonas uenonis, Prevotella albensis, Prevotella bergensis, Prevotella bivia, Prevotella buccae, Prevotella buccalis, Prevotella corporis, Prevotella denticola, Prevotella disiens, Prevotella heparinolytica, Prevotella intermedia, Prevotella loescheii, Prevotella marshii, Prevotella melaninogenica, Prevotella multiformis, Prevotella multisaccharivorax, Prevotella nanceiensis, Prevotella nigrescens, Prevotella oralis, Prevotella oris, Prevotella pallens, Prevotella ruminicola, Prevotella tannerae, Propionibacterium acnes, Propionibacterium avidum, Propionibacterium granulosum, Proteus mirabilis, Proteus penneri, Proteus vulgaris, Providencia alcalifaciens, Providencia rettgeri, Providencia rustigianii, Providencia stuartii, Pseudomonas aeruginosa, Pseudomonas mendocina, Pseudomonas putida, Pseudoramibacter alactolyticus, Ralstonia pickettii, Raoultella ornithinolytica, Rhodococcus equi, Roseburia faecis, Roseomonas cervicalis, Roseomonas mucosa, Rothia dentocariosa, Rothia mucilaginosa, Selenomonas artemidis, Selenomonas dianae, Selenomonas flueggei, Selenomonas infelix, Selenomonas noxia, Serratia liquefaciens, Serratia marcescens, Serratia proteamaculans, Slackia exigua, Sphingobacterium multivorum, Sphingobacterium spiritivorum, Staphylococcus auricularis, Staphylococcus capitis, Staphylococcus caprae, Staphylococcus carnosus, Staphylococcus cohnii, Staphylococcus condimenti, Staphylococcus epidermidis, Staphylococcus equorum, Staphylococcus fleurettii, Staphylococcus haemolyticus, Staphylococcus hominis, Staphylococcus lugdunensis, Staphylococcus pasteuri, Staphylococcus pseudintermedius, Staphylococcus saccharolyticus, Staphylococcus saprophyticus, Staphylococcus sciuri, Staphylococcus*

*succinus, Staphylococcus vitulinus, Staphylococcus warneri, Staphylococcus xylosus, Stenotrophomonas maltophilia, Streptobacillus moniliformis, Streptococcus agalactiae, Streptococcus alactolyticus, Streptococcus anginosus, Streptococcus australis, Streptococcus bovis, Streptococcus canis, Streptococcus constellatus, Streptococcus cristatus, Streptococcus downei, Streptococcus dysgalactiae, Streptococcus equi, Streptococcus equinus, Streptococcus gallolyticus, Streptococcus gordonii, Streptococcus infantarius, Streptococcus infantis, Streptococcus intermedius, Streptococcus lutetiensis, Streptococcus massiliensis, Streptococcus milleri, Streptococcus mitis, Streptococcus mutans, Streptococcus oligofermentans, Streptococcus oralis, Streptococcus parasanguinis, Streptococcus pasteurianus, Streptococcus peroris, Streptococcus pneumoniae, Streptococcus porcinus, Streptococcus pseudopneumoniae, Streptococcus pseudoporcinus, Streptococcus ratti, Streptococcus salivarius, Streptococcus sanguinis, Streptococcus sinensis, Streptococcus suis, Streptococcus thermophilus, Streptococcus uberis, Streptococcus urinalis, Streptococcus vestibularis, Streptococcus viridans, Sutterella wadsworthensis, Tannerella forsythia, Tatlockia micdadei, Tatumella ptyseos, Tissierella praeacuta, Tropheryma whipplei, Tsukamurella tyrosinosolvens, Ureaplasma parvum, Ureaplasma urealyticum, Vagococcus fluvialis*, and *Veillonella parvula*.

In some embodiments the preparations, e.g., compositions are formulated as pharmaceutical preparations for oral, topical, nasal, respiratory, parenteral, intraperitoneal, intravenous, intraarterial, transdermal, sublingual, intramuscular, rectal, transbuccal, vaginal, intraocular, subcutaneous, intraadiposal, iintraarticular, intrathecal administration. In some embodiments, the formulation is a slow release formulation. In some embodiments, the compositions are formulated as medical foods, nutritional or dietary supplements, food products or beverage products. Formulations are described in more detail herein.

Methods of Treating Immune System Diseases and Disorders

Described herein are methods of treating, preventing or reducing the severity of at least one symptom associated with an immune system disorder in a subject, e.g., a human subject, in need thereof, the method comprising administering to the subject or if the subject is a fetus, to the mother thereof, an effective amount of a preparation comprising a first isolated bacterial population. Included are methods to reduce the time and/or severity of a symptom of an immune disorder.

The immune system disorders, e.g., diseases and symptoms include diseases such as autoimmune diseases, inflammatory diseases, or allergic diseases, and symptoms accompanying organ transplants (these diseases and symptoms may hereinafter also be referred to as "the diseases, etc."). A preparation comprising a first isolated bacterial population can treat at least one of the above diseases, for example, ameliorating at least one sign or symptom. In general, a sign is a medical fact, generally observed by a health care professional. A symptom is generally a subjective experience of the subject. In some cases, diagnosis of a condition is based on a combination of signs and symptoms.

In some embodiments, the immune disorders are associated with aberrant pro-inflammatory T cells (i.e., Th17 cells). In addition, because Th17 cells in a mother can exert a pathological effect on a fetus in utero, provided are bacterial compositions and methods to be administered to pregnant women to reduce pathological Th17 activity and pathological immune changes resulting therefrom.

In some embodiments, the disease is an autoimmune disease. In some cases, the disease is accompanied by inflammation that may be induced by excessive production of a cytokine (for example, IL-1 (e.g., IL-1β), IL-4, IL-6, IL-17, TNF-alpha, or IL-6) due to immune reaction with respect to antigen or a microbial molecule or product that stimulates an innate response. Accordingly, a preparation comprising a first isolated bacterial population described herein can, e g., reduce expression or the presence of a cytokine associated with inflammation or otherwise reduce or inhibit inflammation associated with an autoimmune disease, inflammatory disease, allergic disease or like diseases; or inflammation induced by an organ transplant or the like.

An autoimmune disease that may be treated or prevented using a composition described herein can include various morbid conditions accompanied by one or more signs or symptoms in various body parts. For example, autoimmune diseases may include that may be treated or prevented using a composition described herein include, but are not limited to, an autoimmune disease affecting a specific organ, for example, an autoimmune disease of the cranial nervous system, an autoimmune disease of blood circulatory system, and an autoimmune disease of bowel/digestive (gastrointestinal) system.

Examples of cranial nervous system autoimmune diseases include, but are not limited to, chronic inflammatory demyelinating polyneuropathy and multiple sclerosis. Examples of blood circulatory system autoimmune diseases include, but are not limited to, arteriosclerosis. Examples of bowel/digestive system autoimmune diseases include, but are not limited to, Crohn's disease, ulcerative colitis, microscopic colitis and celiac disease. Autoimmune diseases of other body parts or organs, for example, chronic nephritis, chronic inflammatory pulmonary disease, etc. and systemic autoimmune diseases, for example, diabetes, rheumatoid arthritis, etc., are also included. The autoimmune diseases include rheumatoid arthritis and multiple sclerosis.

An inflammatory disease can include various inflammatory conditions accompanied by one or more signs or symptoms in at least one body part. For example, an inflammatory disease may include one or more of alterative inflammation, exudative inflammation, and hyperplastic inflammation. The inflammatory disease may be acute or chronic. For example, inflammatory diseases include, but are not limited to, inflammatory diseases of specific organs such as cranial nervous system inflammatory diseases, blood circulatory system inflammatory diseases, bowel/digestive system inflammatory diseases, and the like.

In some embodiments, an allergic disease that can be treated using a composition described herein is accompanied by inflammation, i.e., at least one sign or symptom of inflammation. Specific examples of allergic diseases include, but are not limited to, contact dermatitis accompanied by Type IV reaction (delayed allergic reaction) according to Coombs classification; and, although they are not classified into Type IV, allergic rhinitis, allergic asthma, atopic dermatitis, acute disseminated encephalomyelitis, and hay fever accompanied by inflammation.

In other embodiments, the methods described herein are used to treat symptoms accompanying an organ transplant including, but not limited to, symptoms (preferably inflammation) accompanying organ transplants that occur between the organ donors and the organ recipients due to immune response. Specific examples of morbid conditions of the symptoms accompanying organ transplants include, but are not limited to, graft-versus-host disease, and acute and chronic rejection responses.

The target diseases of the present invention include various diseases of various subjects, e.g., animals. In some embodiments, the diseases are diseases of human or non-human mammals such as apes, mice, rats, canine, rabbits, bovine, and horses. In one embodiment, the diseases are of mice. In one embodiments, the diseases are human diseases.

In some embodiments, the preparation, e.g., bacterial composition modulates (e.g., increases or decreases) the population of at least one native enteric bacterial OTU present in the human subject being treated. A native enteric bacterial OTU is one that is present in the subject before treatment. The native enteric bacterial OTU may be detected before treatment. In some embodiments, the native enteric bacterial OTU is present, but not necessarily detectable before treatment. In the case of an increase, the increase can be, in some embodiments, an increase is in the amount of a bacterial OTU that is present in the composition. In some embodiments, the bacterial OTU is not present in the composition.

Gastrointestinal Permeability

Provided are preparations, e.g., bacterial compositions and methods that modulate (e.g., decrease) gastrointestinal permeability, e.g., compositions comprising at least one, two, three, four, five, six eight, ten, twelve, fifteen, twenty, or more OTUs selected from Table 1, Table 3, Table 4, Table 7 and/or Table 8. Compositions can be derived from known network ecologies, e.g., core network ecologies as exemplified in Tables 4, 5a-c, and 6.

Decreased gut permeability is demonstrated by methods known in the art, such as a lactulose-mannitol test, wherein a subject is given a solution containing mannitol and lactulose and urine is collected for six hours and tested. Lactulose (a disaccharide) and Mannitol (a monosaccharide) are two water soluble, non-metabolised sugar molecules. Mannitol is easily absorbed, passively penetrating cells, whilst Lactulose, with a larger molecular weight and size, is only partially absorbed by a healthy gut. If the levels of mannitol and lactulose in the collected urine sample are high it is indicative of leaky gut syndrome. Low levels of both molecules indicate malabsorption of nutrients. High levels of mannitol and low levels of lactulose indicate that the person has normal gastrointestinal (GI) barrier function.

Also provided are methods of digestive stool analysis, which includes the testing of fecal material for digestive function, the extent to which lipids, proteins, carbohydrates and other nutrients are absorbed in the small intestine and colon, as well as for the presence of *candida* or other bacterial infections, dysbiosis (imbalance in intestinal bacteria), parasitic infection and other indicators of digestive dysfunction. Also measured are the improvements in bowel function caused by the administration of the bacterial compositions of the present invention, as measured by decreased diarrhea, decreased leaky gut syndrome, increased solid stool, increased production of 5-hydroxy-tryptophan and 5-hydroxytryptamine and 2-methyl-5-hydroxytryptamine, and other neurotransmitter precursors that can be made by bacterial populations (serotonin precursors).

Co-Formulation and Co-Administration

In some embodiments, a bacterial composition described herein is co-formulated and/or co-administered with a pharmacological agent, e.g., an agent that modulates inflammation and/or affects the gastrointestinal tract. In another embodiment, the pharmacological agent modulates a metabolic function of the subject.

In another embodiment, the co-formulated substance is an allergen, e.g., an antigen, with the purpose of inducing immunologic tolerance to said antigen. An exemplary listing of potential antigens (i.e., allergens) or organisms from which allergens can be derived includes: mites (mite house dust) such as *Dermatophagoides farina*; mite house dust, *Dermatophagoides pteronyssinus*; Mite *Acarus siro*, food/storage mite, house dust *Blomia tropicalis* mite, storage *Chortoglyphus arcuates* mite, house dust *Euroglyphus maynei* Mite, *Lepidoglyphus* Food/Storage destructor Mite, *Tyrophagus* Food/Storage *putrescentiae* Mite, House Dust *Glycyphagus domesticus*, and other allergens, for example Venoms Bumble Bee *Bombus* spp., Venom European Hornet *Vespa crabro*, Venom Honey Bee *Apis mellifera*, Venom Mixed Hornet *Dolichovespula*, Venom spp Mixed Paper *Polistes* spp., Wasp Venom Mixed Yellow *Vespula* spp., Jacket Venom White (bald)-*Dolichovespula* faced Hornet *maculate*, Venom Yellow Hornet *Dolichovespula*, Venom *arenaria* Insects Ant, Carpenter *Camponotus pennsylvanicus* Ant, Fire *Solenopsis invicta* Ant, Fire *Solenopsis richteri* Cockroach, *Periplaneta americana*, *Blattella germanica*, *Blatta orientalis*, Oriental horse fly *Tabanus* spp., *Musca domestica*, Mayfly *Ephemeroptera* spp., Mosquito *Culicidae* sp., Moth *Heterocera* spp., epithelia, dander, hair, feathers, e.g., from *Serinus canaria*, at epithelia from *Felis catus* (domesticus), Cattle Epithelia *Bos Taurus*, Chicken Feathers *Gallus gallus* (domesticus), Dog Epithella, *Canis familiaris* Mixed Breeds, Duck Feathers *Anas platyrhynchos*, Gerbil Epithelia *Meriones unguiculatus*, Goat Epithelia *Capra hircus*, Goose Feathers *Anser domesticus*, Guinea Pig *Cavia porcellus* Epithelia (cobaya), Hamster Epithelia *Mesocricetus auratus*, Hog Epithelia *Sus scrofa*, Horse Epithelia *Equus caballus*, Mouse Epithelia *Mus musculus*, Parakeet Feathers Psittacidae spp., Pigeon Feathers *Columba fasciata*, Rabbit Epithelia *Oryctolagus cuniculus*, Rat Spithelia *Rettus norvegicus* Wool, Sheep *Ovis aries* Dander, cat dander/antigen, *Felis catus*; dog dander, *Canis familiaris* (e.g., Mixed-Breed Poodle Dander, *Canis familiaris*), Fungi Acremonium, Cephalosporium strictum acremonium, Alternaria, Alternaria alternate tenuis, Aspergillus, Aspergillus amstelodami glaucus, Aspergillus flavus, Aspergillus fumigatus, Aspergillus nidulans, Aspergillus niger, Aspergillus terreus, Aspergillus versicolor, Aureobasidium Pullularia pullulans pullulans, Bipolaris Drechslera sorokiniana sorokiniana, Helminthosporium sativum, Botrytis cinerea, Candida albicans, Chaetomium globosum, Cladosporium herbarum, Cladosporium Hormodendrum sphaerospermum hordei, Drechslere Curvularia spicifera spicifera, Epicoccum, Epicoccum nigrum purpurascens, Epidermophyton floccosum, Fusarium moniliforme, Fusarium solani, Geotrichum, Oospora lactis candidum, Gliocladium, Gliocladium viride deliquescens, Helminthosporium, Spondylocladium solani atrovirens, Microsporum, Microsporum canis lanosum, Mucor, Mucor mucedo circinelloides f. circinelloides, Mucor, Mucor circinelloides f. racemosus lusitanicus, Mucor plumbeus, Mycogone perniciosa, Neurospor, a Neurospora intermedia sitophila, Monilia sitophila, Nigrospora oryzae, Paecilomyces variotii, Penicillium brevicompactum, Penicillium camembertii, Penicillium chrysogenum, Penicillium digitatum, Penicillium expensum, Penicillium notatum, Penicillium roquefortii, Phoma betae, Phomma, Phoma herbarum pigmentivora, Rhigopus oryzae, Rhizopus arrhizus, Rhizopus, Rhizopus stolonifer nigricans, Rhodotorula,

*Rhodotorula mucilaginosa rubra* var. *mucilaginosa*, *Saccharomyces cerevisiae*, *Scopulariopsis brevicaulis*, *Serpula lacrymans*, *Merulius lacrymans*, *Setosphaeria Exserohilum rostrata rostratum*, *Helminthosporium halodes*, *Stemphylium botryosum*, *Stemphylium solani*, *Trichoderma*, *Trichoderma harzianum viride*, *Trichophyton*, *Trichophyton mentagrophytes interdigitale*, *Trichophyton rubrum*, *Trichothecium*, *Cephalothecium roseum*, *roseum*, Smuts Barley, Smut *Ustilago nuda*, Bermuda Grass *Ustilago* Smut *cynodontis*, Corn Smut *Ustilago maydis*, Johnson Grass *Sporisorium* Smut *cruentum*, Oat Smut *Ustilago avenae*, Wheat Smut *Ustilago tritici*, Grass Pollens, Bahia *Paspalum notatum*, Bermuda *Cynodon dactylon* Blue, Canada *Poa compressa* Brome, Smooth *Bromus inermis*, Canary *Phalaris arundinacea*, Corn *Zea mays* Couch/Quack *Elytrigia repens* (*Agropyron repens*), Johnson *Sorghum halepense* Kentucky Blue *Poa pratensis* Meadow Fescue *Festuca pratensis* (*elatior*) Oat, Cultivated *Avena sativa* Orchard *Dactylis glomerata* Red Top *Agrostis gigantean* (alba) Rye, Cultivated *Secale cereale* Rye, Giant Wild *Leymus* (*Elymus*) *condensatus* Rye, Italian *Lolium perenne* ssp. *multiflorum* Rye, Perennial *Lolium perenne* Sweet Vernal *Anthoxanehum odoratum*, Timothy *Phleum pratense* Velvet *Holcus lanatus* Wheat, Cultivated *Triticum aestivum* Wheatgrass, *Elymus* Western (*Agropyron*) *smithii*, Weed Pollens Allscale *Atriplex polycarpa*, *Baccharis Baccharis halimifolia*, *Baccharis Baccharis sarothroides*, Burrobrush *Hymenoclea salsola*, Careless Weed *Amaranthus hybridus*, Cocklebur *Xanthium strumarium* (commune) Dock, Yellow *Rumex crispus*, Dog Fennel *Eupatorium capillifolium* Goldenrod *Solidago* spp. Hemp, Western *Amaranthus* Water *tuberculatus* (*Acnida tamariscina*), Iodine Bush *Allenrolfea occidentalis*, Jerusalem Oak *Chenopodium botrys* Kochia/Firebush *Kochia scoparia*, Lambs Quarter *Chenopodium album*, Marsh Elder, *Iva xanthifolia*, Burweed Marsh Elder, *Iva angustifolia* Narrowleaf Marsh Elder, *Iva annua* Rough (*ciliata*) Mexican Tea *Chenopodium ambrosioides*, Mugwort, *Artemisia* Common *vulgaris* Mugwort, *Artemisia* Darkleaved *ludoviciana*, Nettle *Urtica dioica*, Palmer's *Amaranthus* Amaranth *palmeri*, Pigweed *Amaranthus* Redroot/Rough *retroflexus*, Pigweed Spiny *Amaranthus spinosus*, Plantain English *Plantago lanceolata*, Poverty Weed *Iva axillaris*, Quailbrush *Atriplex lentiformis*, Rabbit Bush *Ambrosia deltoidea*, Ragweed Desert *Ambrosia dumosa*, Ragweed False *Ambrosia acanthicarpa*, Ragweed Giant *Ambrosia trifida*, Ragweed Short *Ambrosia artemisiifolia*, Ragweed Slender *Ambrosia confertiflora*, Ragweed *Ambrosia* Southern *bidentata*, Ragweed *Ambrosia* Western *psilostachya*, Russian Thistle *Salsola kali* (*pestifer*) Sage, Coastal *Artemisia californica* Sage, Pasture *Artemisia frigida* Sagebrush, *Artemisia* Common *tridentate*, Saltbush, Annual *Atriplex wrightii*, Shadscale *Atriplex confertifolia*, Sorrel, Red/Sheep *Rumex acetosella*, Wingscale *Atriplex canescens*, Wormwood, *Artemisia annua* Annual Tree Pollens Acacia *Acacia* spp., Alder, European *Alnus glutinosa* Alder, Red *Alnus rubra* Alder, Tag *Alnus incana* ssp. *rugosa* Alder, White *Alnus rhombifolia* Ash, Arizona *Fraxinus velutina* Ash, Green/Red *Fraxinus pennsylvanica* Ash, Oregon *Fraxinus latifolia* Ash, White *Fraxinus Americana*, Aspen *Populus tremuloides*, Bayberry *Myrica cerifera* Beech, American *Fagus grandifolia* (*americana*), Beefwood/Australian *Casuarina* Pine *equisetifolia* Birch, *Betula lenta*, Black/Sweet Birch, European *Betula pendula* White Birch, Red/River *Betula nigra* Birch, Spring *Betula occidentalis* (*fontinalis*) Birch, White *Betula populifolia* Box Elder *Acer negundo* Cedar, Japanese *Cryptomeria japonica* Cedar, Mountain *Juniperus ashei* (*sabinoides*) Cedar, Red *Juniperus virginiana* Cedar, Salt *Tamarix gallica* Cottonwood, *Populus* Black *balsamifera* ssp. *Trichocarpa* Cottonwood, *Populus* Eastern *deltoides* Cottonwood, *Populus Fremont fremontii* Cottonwood, Rio *Populus* Grande *wislizeni* Cottonwood, *Populus* Western *monilifera* (*sargentii*) Cypress, Arizona *Cupressus arizonica* Cypress, Bald *Taxodium distichum* Cypress, Italian *Cupressus sempervirens* Elm, American *Ulmus americana* Elm, Cedar *Ulmus crassifolia* Elm, Siberian *Ulmus pumila* Eucalyptus *Eucalyptus globulus* Hackberry *Celtis occidentalis* Hazelnut *Corylus americana* Hazelnut, *Corylus* European *avellana* Hickory, Pignut *Carya glabra* Hickory, *Carya ovata* Shagbark Hickory, *Carya laciniosa* Shellbark Hickory, White *Carya alba* Juniper, Oneseed *Juniperus monosperma* Juniper, Pinchot *Juniperus pinchotii* Juniper, Rocky *Juniperus* Mountain *scopulorum* Juniper, Utah *Juniperus osteosperma* Juniper, Western *Juniperus occidentalis* Locust Blossom, *Robinia* Black *pseudoacacia* Mango Blossom *Mangifera indica* Maple, Coast *Acer macrophyllum* Maple, Red *Acer rubrum* Maple, Silver *Acer saccharinum* Maple, Sugar *Acer saccharum* Melaleuca *Melaleuca quinquenervia* (*leucadendron*) Mesquite *Prosopis glandulosa* (*juliflora*) Mulberry, Paper *Broussonetia papyrifera* Mulberry, Red *Moms rubra* Mulberry, White *Moms alba* Oak, *Quercus* Arizona/Gambel *gambelii* Oak, Black *Quercus velutina* Oak, Bur *Quercus macrocarpa* Oak, California *Quercus* Black *kelloggii* Oak, California *Quercus* Live *agrifolia* Oak, California *Quercus lobata* White/Valley Oak, English *Quercus robur* Oak, Holly *Quercus ilex* Oak, Post *Quercus stellata* Oak, Red *Quercus rubra* Oak, Scrub *Quercus dumosa* Oak, Virginia *Quercus* Live *virginiana* Oak, Water *Quercus nigra* Oak, Western *Quercus* White/Garry *garryana* Oak, White *Quercus alba* Olive *Olea europaea* Olive, Russian *Elaeagnus angustifolia* Orange Pollen *Citrus sinensis* Palm, Queen *Arecastrum romanzoffianum* (*Cocos plumosa*) Pecan *Carya illinoensis* Pepper Tree *Schinus molle* Pepper *Schinus* Tree/Florida *terebinthifolius* Holly Pine, Loblolly *Pinus taeda* Pine, Eastern *Pinus strobus* White Pine, Longleaf *Pinus palustris* Pine, Ponderosa *Pinus ponderosa* Pine, Slash *Pinus elliottii* Pine, Virginia *Pinus virginiana* Pine, Western *Pinus monticola* White Pine, Yellow *Pinus echinata* Poplar, Lombardy *Populus nigra* Poplar, White *Populus alba* Privet *Ligustrum vulgare* Sweet Gum *Liquidambar styraciflua* Sycamore, *Platanus* Eastern *occidentalis* Sycamore, *Platanus* Oriental *orientalis* Sycamore, *Platanus* Western *racemosa* Sycamore/London *Platanus* Plane *acerifolia* Walnut, Black *Juglans nigra* Walnut, *Juglans* California Black *californica* Walnut, English *Juglans regia* Willow, Arroyo *Salix lasiolepis* Willow, Black *Salix nigra* Willow, Pussy *Salix discolor* Flowers; Wild & Cultivated Daisy, Ox-Eye *Chrysanthemum leucanthemum*, Dandelion *Taraxacum officinale*, Sunflower *Helianthus annuus*, Cultivated Farm Plant Pollens Alfalfa *Medicago sativa*, Castor Bean *Ricinus communis* Clover, Red *Trifolium pratense* Mustard *Brassica* spp., Sugar Beet *Beta vulgaris*, Plant Food Almond *Prunus dulcis* Apple *Malus pumila*, Apricot *Prunus armeniaca*, Banana *Musa paradisiaca* (*sapientum*), Barley *Hordeum vulgare* Bean, Lima *Phaseolus lunatus* Bean, Navy *Phaseolus vulgaris* Bean, Pinto *Phaseolus* sp. Bean, Red Kidney *Phaseolus* sp. Bean, *Phaseolus* String/Green *vulgaris* Blackberry *Rubus alleghieniensis*, Blueberry *Vaccinium* sp., Broccoli *Brassica oleracea* var. *botrytis*, Buckwheat *Fagopyrum esculentum*, Cabbage *Brassica oleracea* var. *capitata*, Cacao Bean *Theobroma cacao*, Cantaloupe *Cucumis melo*, Carrot *Daucus carota*, Cauliflower *Brassica oleracea* var. *botrytis*, Celery *Apium graveolens* var. *dulce*, Cherry *Prunus* sp., Cinnamon *Cinnamomum verum*, Coffee, Coffee *Arabica*, Corn *Zea mays*, Cranberry Vaccinium macrocarpon, Cucumber Cucumis sativus, Garlic Allium sativum, Ginger Zingiber officinale, Grape Vitis sp., Grapefruit Citrus paradise, Hops Humulus lupulus, Lemon, Citrus limon, Lettuce Lactuca sativa, Malt Mushroom Agaricus campestris, Mustard Brassica sp., Nutmeg Myristica fragrans, Oat Avena sativa Olive, Green Olea europaea, Onion Allium cepa var. cepa, Orange Citrus sinensis Pea, Blackeye Vigna unguiculata Pea, Green Pisum sativum (English), Peach Prunus persica, Pear Pyrus communis Pepper, Black Piper nigrum Pepper, Green Capsicum annuum var. annuum Pineapple Ananas comosus Potato, Sweet Ipomoea batatas Potato, White Solanum tuberosum Raspberry Rubus idaeus var. idaeus, Rice Oryza sativa, Rye Secale cereal, Sesame Seed Sesamum orientale (indicum), Soybean Glycine max, Spinach, Spinacia oleracea, Squash, Yellow Cucurbita pepo var. melopepo, Strawberry Fragaria chiloensis, Tomato Lycopersicon esculentum (lycopersicum), Turnip Brassica rapa var. rapa, Vanilla Bean, Vanilla planifolia, Watermelon, Citrullus lanatus var. lanatus, Wheat, Whole Triticum aestivum, Fish & Shellfish Bass, Black Micropterus sp., Catfish, Ictalurus punctatus, Clam Mercenaria mercenaria, Codfish, Gadus morhua, Crab Callinectes sapidus, Flounder Platichthys sp., Halibut Hippoglossus sp., Lobster Homarus americanus, Mackerel Scomber scombrus, Oyster, Crassostrea virginica, Perch Sebastes marinus, Salmon Salmo salar, Sardine, Clupeiformes, Scallop, Pectan magellanicus, Shrimp Penaeus sp., Trout, Lake Salvelinus sp., Tuna Fish, Thunnus sp., Animal Foods, Beef Bos Taurus, Lamb, Ovis aries, Pork, Sus scrofa, Poultry Products, Chicken, Gallus gallus Egg, Chicken, Gallus gallus White Egg, Chicken, Gallus gallus Yolk Turkey Meleagris gallopavo Dairy Products Casein, bovine Bos taurus Milk, bovine Bos taurus, Nuts, Brazil Nut, Bertholletia excelsa, Cashew Nut, Anacardium occidentale, Coconut, Cocos nucifera Filbert/Hazelnut Corylus Americana, Peanut, Arachis hypogaea, Pecan, Carya illinoensis, Walnut, Black Juglans nigra Walnut, English Juglans regia, and miscellaneous latex.

Pharmaceutical and Nutritional Compositions and Formulations

In some embodiments, the preparations comprising isolated bacterial populations are in a pharmaceutical composition. For example, the preparation may contain non-cellular materials, for example an extracellular product of non-lactic acid-producing bacteria, a bacterial supplement, binder, filler, vitamin, mineral, or combination thereof. Additional ingredients include ingredients to improve handling, preservatives, antioxidants, flavorings and the like. For example, in one embodiment, a preparation can include flavorings that can flavor the preparation with various flavors such as grape, strawberry, lime, lemon, chocolate, and the like. In one embodiment, the preparations include microcrystalline cellulose or silicone dioxide. Preservatives can include, for example, benzoic acid, alcohols, for example, ethyl alcohol, and hydroxybenzoates. Antioxidants can include, for example, butylated hydroxyanisole (BHA), butylated hydroxytolulene (BHT), tocopherols (e.g., vitamin E), and ascorbic acid (vitamin C). In some embodiments, the bacterial population is present in a stabilized form in the preparation, meaning that the bacteria present in the population are not in a vegetative (i.e., growth) state prior to being consumed by a human, or prior to delivery to a certain region of the consumer's gastrointestinal tract. Stabilized bacterial populations are generally contained in or combined with a stabilizer, such as an enteric material. In some embodiments, the enteric material is acid-labile, meaning it dissolves when exposed to an acidic environment such as the stomach. Alternatively, the enteric material is acid-stable and base-labile, meaning it will not dissolve in the stomach, but will dissolve in the small intestine. In some embodiments, the enteric material is heat-labile, meaning it is stabile at a given temperature, typically above about room temperature but below physiological temperature. For example, the enteric material has a melting temperature of at least 30 degrees Celsius.

In some embodiments, the preparations described herein contain non-lactic acid-producing bacteria or comprise compositions that contain lactic-acid producing and non-lactic acid producing bacteria. In some embodiments such bacteria are from the families Bacteroidaceae, Clostridiaceae, Coriobacteriaceae, Desulfovibrionaceae, Erysipelotrichaceae, Eubacteriaceae, Hyphomicrobiaceae, Lachnospiraceae, Oscillospiraceae, Porphyromonadaceae, Rikenellaceae, Ruminococcaceae, or Verrucomicrobiaceae. Additionally, in some embodiments the non-lactic acid-producing bacteria are from the genera Akkermansia, Alistipes, Anaerostipes, Bacteroides, Bilophila, Blautia, Butyricioccus, Butyrivibrio, Clostridium, Coprococcus, Desulfovibrio, Dorea, Eggerthella, Eubacterium, Faecalibacterium, Gemmiger, Holdemania, Oscillibacter, Parabacteroides, Pseudoflavonifractor, Roseburia, Ruminococcus, Sporobacter, or Subdoligranulum.

Pharmaceutical or nutritional products are formulated such that a single administered dose or consumed unit contains at least about $1 \times 10^4$ colony forming units (cfus) of the bacteria, and a single consumed unit will contain, for example about $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, or greater than $1 \times 10^{15}$ cfus of the bacteria; or contain at least $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, or greater than $1 \times 10^{15}$ cfus. The concentration of bacteria of a given species, clade or OTU, or the aggregate of all species or OTUs, is e.g., $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, or greater than $1 \times 10^{15}$ viable bacteria per gram of comestible product or per consumed dose.

The bacteria are administered, for example, as live cultured bacteria, in vegetative or spore form or as a combination of vegetative and spore forms. Alternatively, the bacteria are provided as purified populations obtained from a microbiotal material such as a fecal material.

The amount of bacteria contained in a dose or composition can be about 0.001 mg to about 1 mg, about 0.5 mg to about 5 mg, about 1 mg to about 1000 mg, about 2 mg to about 200 mg, about 2 mg to about 100 mg, about 2 mg to about 50 mg, about 4 mg to about 25 mg, about 5 mg to about 20 mg, about 10 mg to about 15 mg, about 50 mg to about 200 mg, about 200 mg to about 1000 mg, or about 1, 2, 3, 4, 5 or more than 5 g per dose or composition; or 0.001 mg to 1 mg, 0.5 mg to 5 mg, 1 mg to 1000 mg, 2 mg to 200 mg, or 2 mg to 100 mg, or 2 mg to 50 mg, or 4 mg to 25 mg, or 5 mg to 20 mg, or 10 mg to 15 mg, or 50 mg to 200 mg, or 200 mg to 1000 mg, or 1, 2, 3, 4, 5 or more than 5 g per dose or composition.

In some embodiments, provided in the pharmaceutical or nutritional products is a prebiotic material, or "prebiotic." Generally, a prebiotic material contains a saccharide indigestible by a human digestive system, but digestible by the bacterial population present in the bacterial composition. In another embodiment, the prebiotic saccharide contains a mixture of non-digestible oligosaccharides or polysaccharides. In another embodiment a prebiotic composition comprises one or more digestible saccharides and one or more non-digestible oligosaccharides or polysaccharides. In one embodiment the saccharide is an oligosaccharide, such as a disaccharide, a trisaccharide, a tetrasaccharide, a pentasaccharide, a hexasaccharide, a heptasaccharide, an octasaccharide, a nanasaccharide, or a decasaccharide. Exemplary prebiotics useful in the present compositions include gluco-oligosaccharides, inulin, fructo-oligosaccharides, xylo-oligosaccharides, sugar alcohol(s), transgalactooligosaccharides, galacto-oligosaccharides, lactulose, raffinose, stachyose, lactosucrose, isomalto-oligosaccharides, xylo-oligosaccharides, paratinose oligosaccharides, difructose anhydride III, sorbitol, maltitol, lactitol, reduced paratinose, cellulose, beta-glucose, beta-glucan, beta-galactose, beta-fructose, verbascose, galactinol, guar gum, pectin, high sodium alginate, and lambda carrageenan. In one embodiment, a prebiotic-containing composition contains about 1-90%, about 1-10%, about 2-5%, about 10-90%, about 20-50%, about 20-90%, about 30-90%, about 40-90%, about 40-80%, about 40-70%, about 40-60%, about 40-50%, about 50-90%, about 50-80%, about 50-70%, about 50-60%, about 60-90%, about 60-80%, about 60-70%, about 70-90%, about 70-80%, about 70-90%, about 70-80%, about 80-90%, about 92-99.9%, about 93-99%, about 94-98%, about 92-96%, about 93-96%, or about 93-95% by weight prebiotic. In another embodiment, a prebiotic-containing composition contains 1-90%, 1-10%, 2-5%, 10-90%, 20-50%, 20-90%, 30-90%, 40-90%, 40-80%, 40-70%, 40-60%, 40-50%, 50-90%, 50-80%, 50-70%, 50-60%, 60-90%, 60-80%, 60-70%, 70-90%, 70-80%, 70-90%, 70-80%, 80-90%, 92-99.9%, 93-99%, 94-98%, 92-96%, 93-96%, or 93-95% by weight prebiotic.

As provided herein, described herein is a food product, in particular a medical food product, containing one or more comestible products and a foodstuff, such as a dairy product, an infant food product, a fruit-containing food product, a vegetable-containing food product, or a sports nutrition food product. The foodstuffs of the present invention can be applied in infant diets, adult diets and special diets, including diets requiring medical foods or functional foods. The bacterial compositions can be incorporated in powder or in liquid form in foods used by the general population, particularly milk and milk-derived products, especially fermented milk and cheeses; cereals and derivatives, including bread, bread doughs, cakes, cookies, crackers, extruded snacks; soups and other similar products in dehydrated form; fermented meat products; fruit and vegetable derivatives, juices and soft drinks; foods for specific nutritional uses, including infant milk, infant cereals, ready-to-eat infant foods, etc. They can also be found in food supplements and special formulas for oral and enteral nutrition for clinical use. In other embodiments, the foodstuff is yogurt, kefir, yakult, miso, natto, tempeh, kimchee, sauerkraut, water, coffee, tea, beer, wine, liquor, alcoholic mixed drinks, soups, frozen desserts, fried foods, pasta products, potato products, rice products, corn products, wheat products, dairy products, confectioneries, hard candies, nutritional bars, and breakfast cereals. Generally, the bacterial population includes bacteria present in the foodstuff in an amount from about $10^4$ to about $10^{12}$ cfu per gram of foodstuff, e.g., from $10^4$ to $10^{12}$ cfu per gram of foodstuff. Additionally, the bacterial population is stabilized to prevent spoilage of the foodstuff. In some embodiments, the food product contains an effective amount of a prebiotic material comprising a saccharide indigestible by a human digestive system; in some embodiments the prebiotic material is also stabilized. In another aspect, provided is a beverage containing the comestible product and a liquid other than water, such as a dairy-containing liquid, an infant formula, a fruit juice, a vegetable juice, or a sports nutrition liquid. Generally, the bacterial population is present in the liquid in an amount from about $10^4$ to about $10^{12}$ cfu per gram of liquid, e.g., from $10^4$ to $10^{12}$ cfu per gram of liquid. In some embodiments the beverage includes a prebiotic material, such as a saccharide indigestible by a human digestive system. The beverage may be hot, warm, room temperature, cool, or cold.

Methods of Preparing Products Containing Bacterial Populations

In certain aspects, methods are provided for preparing a pharmaceutical or nutritional product containing a bacterial population. A carrier is combined with an effective amount of a bacterial population generally containing at least one non-lactic acid-producing bacterium and, optionally, an extracellular product of a non-lactic acid-producing bacterium. For comestible products such as foodstuffs and beverages, an effective amount of the bacterial population is a population containing an amount of bacteria such that the population is at least partially retained in the gastrointestinal tract of a mammalian subject that consumes the comestible product. For example, the bacterial population contains bacteria present in the carrier in an amount from about $10^4$ to about $10^{12}$ cfu per gram of carrier, e.g., from $10^4$ to $10^{12}$ cfu per gram of carrier.

Any suitable amount of bacteria containing composition per serving can be used that allows an effective microbiota in the GI. In one embodiment, a typical nutritive formulation or foodstuff dose or serving is 5-500 g, such as 5-15 g, 15-50 g, 25-75 g, 50-100 g, 100-200 g, 200-300 g, 300-400 g, or 400-500 g. For example, a yogurt composition can be about 4, 6, 8, 10 or 12 ounces, or a quarter, half, three-quarters or whole cup. In one embodiment, a typical serving size for a beverage product such as a fluid is about 10-500 ml, such as 10-25 ml, 25-50 ml, 50-75 ml, 75-100 ml, 100-150 ml, 150-200 ml, 250-300 ml, 300-400 ml, or 400-500 ml.

In one embodiment, a composition is administered as a pharmaceutical preparation in solid, semi-solid, microemulsion, gel, or liquid form. Examples of such dosage forms include tablet forms disclosed in U.S. Pat. Nos. 3,048,526, 3,108,046, 4,786,505, 4,919,939, and 4,950,484; gel forms disclosed in U.S. Pat. Nos. 4,904,479, 6,482,435, 6,572,871, and 5,013,726; capsule forms disclosed in U.S. Pat. Nos. 4,800,083, 4,532,126, 4,935,243, and 6,258,380; or liquid forms disclosed in U.S. Pat. Nos. 4,625,494, 4,478,822, and 5,610,184; each of which is incorporated herein by reference in its entirety. Forms of the compositions that can be used orally include tablets, push-fit capsules made of gelatin, as well as soft, sealed capsules made of gelatin and a plasticizer, such as glycerol or sorbitol. Tablets can be made by compression or molding, optionally with one or more accessory ingredients. Compressed tablets can be prepared by compressing in a suitable machine the active ingredient in a free-flowing form such as a powder or granules, optionally mixed with binders (e.g., povidone, gelatin, hydroxypropylmethyl cellulose), inert diluents, preservative, antioxidant, disintegrant (e.g., sodium starch glycolate, cross-linked povidone, cross-linked sodium carboxymethyl cellulose) or lubricating, surface active or dispersing agents. Molded tablets can be made by molding in a suitable machine a mixture of the powdered compound moistened with an inert liquid diluent. The tablets can optionally be coated or scored and can be formulated so as to provide slow or controlled release of the active ingredient therein. Tablets can optionally be provided with an enteric coating, to provide release in stomach or in parts of the gut (e.g., colon, lower intestine) other than the stomach. All formulations for oral administration can be in dosages suitable for such administration. The push-fit capsules can contain the active ingredients in admixture with filler, such as lactose, binders such as starches, and/or lubricants such as talc or magnesium stearate and, optionally, stabilizers. In soft capsules, the active compounds (prebiotics or probiotics) can be dissolved or suspended in suitable liquids, such as fatty oils, liquid paraffin, or liquid polyethylene glycols. In addition, stabilizers can be added. Dragee cores are provided with suitable coatings. For this purpose, concentrated sugar solutions can be used, which can optionally contain gum arabic, talc, polyvinyl pyrrolidone, carbopol gel, polyethylene glycol, or titanium dioxide, lacquer solutions, and suitable organic solvents or solvent mixtures. Dyestuffs or pigments can be added to the tablets or Dragee coatings for identification or to characterize different combinations of active compound doses. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethylene glycol or an oil medium, for example peanut oil, liquid paraffin, or olive oil. Oral liquid preparations can be in the form of, for example, aqueous or oily suspensions, solutions, emulsions syrups or elixirs, or can be presented as a dry product for reconstitution with water or other suitable vehicle before use. Such liquid preparations can contain conventional additives, such as suspending agents, for example sorbitol, methyl cellulose, glucose syrup, gelatin, hydroxyethyl cellulose, carboxymethyl cellulose, aluminum stearate gel or hydrogenated edible fats, emulsifying agents, for example lecithin, sorbitan monooleate, acacia; nonaqueous vehicles (which can include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

In one embodiment, a provided bacterial composition includes a softgel formulation. A softgel can contain a gelatin based shell that surrounds a liquid fill. The shell can be made of gelatin, plasticizer (e.g., glycerin and/or sorbitol), modifier, water, color, antioxidant, or flavor. The shell can be made with starch or carrageenan. The outer layer can be enteric coated. In one embodiment, a softgel formulation can include a water or oil soluble fill solution, or suspension of a composition, for example, a prebiotic composition, covered by a layer of gelatin.

An enteric coating can control the location of where a bacterial composition is absorbed in the digestive system. For example, an enteric coating can be designed such that a bacterial composition does not dissolve in the stomach but rather travels to the small intestine, where it dissolves. An enteric coating can be stable at low pH (such as in the stomach) and can dissolve at higher pH (for example, in the small intestine). Material that can be used in enteric coatings includes, for example, alginic acid, cellulose acetate phthalate, plastics, waxes, shellac, and fatty acids (e.g., stearic acid, palmitic acid). Enteric coatings are described, for example, in U.S. Pat. Nos. 5,225,202, 5,733,575, 6,139,875, 6,420,473, 6,455,052, and 6,569,457, all of which are herein incorporated by reference in their entirety. The enteric coating can be an aqueous enteric coating. Examples of polymers that can be used in enteric coatings include, for example, shellac, cellulose acetate phthalate, polyvinylacetate phthalate, and methacrylic acid. Enteric coatings can be used to (1) prevent the gastric juice from reacting with or destroying the active substance, (2) prevent dilution of the active substance before it reaches the intestine, (3) ensure that the active substance is not released until after the preparation has passed the stomach, and (4) prevent live bacteria contained in the preparation from being killed because of the low pH-value in the stomach. In one embodiment a bacterial composition or the bacterial component of a food or beverage is provided as a tablet, capsule, or caplet with an enteric coating. In one embodiment the enteric coating is designed to hold the tablet, capsule, or caplet together when in the stomach. The enteric coating is designed to hold together in acid conditions of the stomach and break down in non-acid conditions and therefore release the drug in the intestines. Softgel delivery systems can also incorporate phospholipids or polymers or natural gums to entrap a composition, for example, a prebiotic composition, in the gelatin layer with an outer coating to give desired delayed/control release effects, such as an enteric coating.

In one embodiment a composition is provided in a dosage form which comprises an effective amount of a bacterial population and one or more release controlling excipients as described herein. Suitable modified release dosage vehicles include, but are not limited to, hydrophilic or hydrophobic matrix devices, water-soluble separating layer coatings, enteric coatings, osmotic devices, multi-particulate devices, and combinations thereof. In one embodiment the dosage form is a tablet, caplet, capsule or lollipop. In another embodiment, the dosage form is a liquid, oral suspension, oral solution, or oral syrup. In yet another embodiment, the dosage form is a gel capsule, soft gelatin capsule, or hard gelatin capsule. In another embodiment a composition comprising a bacterial population is provided in effervescent dosage forms. The compositions can also comprise non-release controlling excipients.

In another embodiment a composition comprising a bacterial composition, optionally with a prebiotic material, is provided in the form of enteric-coated pellets, for oral administration. The compositions can further comprise glyceryl monostearate 40-50, hydroxypropyl cellulose, hypromellose, magnesium stearate, methacrylic acid copolymer type C, polysorbate 80, sugar spheres, talc, and triethyl citrate. In one embodiment a composition comprising a bacterial population is provided in the form of enteric-coated granules, for oral administration. The compositions can further comprise carnauba wax, crospovidone, diacetylated monoglycerides, ethylcellulose, hydroxypropyl cellulose, hypromellose phthalate, magnesium stearate, mannitol, sodium hydroxide, sodium stearyl fumarate, talc, titanium dioxide, and yellow ferric oxide.

In one embodiment compositions can be formulated in various dosage forms for oral administration. The compositions can also be formulated as a modified release dosage form, including immediate-, delayed-, extended-, prolonged-, sustained-, pulsatile-, controlled-, extended, accelerated-, fast-, targeted-, programmed-release, and gastric retention dosage forms. These dosage forms can be prepared according to known methods and techniques (see, Remington: The Science and Practice of Pharmacy, supra; Modified-Release Drug Deliver Technology, Rathbone et al., Eds., Drugs and the Pharmaceutical Science, Marcel Dekker, Inc.: New York, N.Y., 2002; Vol. 126, which is herein incorporated by reference in its entirety). In one embodiment, the compositions are in one or more dosage forms. For example, a composition can be administered in a solid or liquid form. Examples of solid dosage forms include but are not limited to discrete units in capsules or tablets, as a powder or granule, or present in a tablet conventionally formed by compression molding. Such compressed tablets can be prepared by compressing in a suitable machine the three or more agents and a pharmaceutically acceptable carrier. The molded tablets can be optionally coated or scored, having indicia inscribed thereon and can be so formulated as to cause immediate, substantially immediate, slow, controlled or extended release of a composition comprising a prebiotic. Furthermore, dosage forms of the invention can comprise acceptable carriers or salts known in the art, such as those described in the Handbook of Pharmaceutical Excipients, American Pharmaceutical Association (1986), incorporated by reference herein in its entirety.

The compositions described herein can be in liquid form. The liquid formulations can comprise, for example, an agent in water-in-solution and/or suspension form; and a vehicle comprising polyethoxylated castor oil, alcohol, and/or a polyoxyethylated sorbitan mono-oleate with or without flavoring. Each dosage form comprises an effective amount of an active agent and can optionally comprise pharmaceutically inert agents, such as conventional excipients, vehicles, fillers, binders, disintegrants, pH adjusting substances, buffer, solvents, solubilizing agents, sweeteners, coloring agents, and any other inactive agents that can be included in pharmaceutical dosage forms for oral administration. Examples of such vehicles and additives can be found in Remington's Pharmaceutical Sciences, 17th edition (1985).

The compositions are capable of being consumed ad libitum. In instances wherein a dysbiosis caused by a disease, disorder, condition or event is being addressed by administration of the compositions, the total duration of consumption, can be from about one week to about 52 weeks, or about four weeks to about twenty six weeks, or about four weeks to about twelve weeks, or about six weeks. In one embodiment a bacterial composition can also be administered in combination with another substance, as described herein. In one embodiment, the total duration of treatment is about 5 days to about 35 days. In one embodiment, the total duration of treatment is about 7 days to about 90 days, or about 7 days to about 60 days, or about 14 days to about 50 days, or about 14 days to about 40 days, or about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days. In another embodiment, the total duration of treatment is about 30 days. In another embodiment, the total duration of treatment is about 34 days. In another embodiment, the total duration of treatment is about 36 days. In another embodiment, the total duration of treatment is about 38 days. In another embodiment, the total duration of treatment is about 42 days. In another embodiment, the total duration of treatment is about 60 days. In another embodiment, the total duration of treatment is about 90 days. In another embodiment, one course of therapy may be followed by another, such as an induction regimen followed by a maintenance regimen.

Computational Methods

Provided herein are compositions based on computational methods using, at least in part, network theory, that delineate ecological structures of a group of microorganisms based on the presence or absence of the specific OTUs (i.e., microbial clades, species or strains) in a population of sampled mammalian subjects. Notably, these network ecologies are not simply inferred based on the clustering of OTUs according to binary co-occurrences computed from average relative abundances across a set of subject samples (see e.g., Faust et al., 2012. Microbial co-occurrence relationships in the human microbiome. PLoS Computational Biology 8:e1002606; Lozupone et al., 2012. Identifying genomic and metabolic features that can underlie early successional and opportunistic lifestyles of human gut symbionts. Genome Research 22:1974-1984), but instead the ecologies represent actual communities of bacterial OTUs that are computationally derived and explicitly exist as an ecological network within one or more subjects. As described herein, provided are compositions containing keystone OTUs, including one or more of the OTUs provided herein. As described herein, provided are compositions containing keystone OTUs and, optionally, non-keystone OTUs, including one or more of the OTUs provided herein. The Tables presented herein provide OTUs, as well as families and genera containing OTUs, which are suitable for use in the bacterial populations provided herein.

The following examples are intended to illustrate and not limit the scope of the invention, the scope being defined exclusively by the issued claims.

Example 1: Oral Food Allergy Models in Brown-Norway Rats with and without Adjuvant Food allergies are an aberrant, IgE-mediated hypersensitivity reaction to food macromolecules or partially digested components thereof. The allergic reaction develops in a two-phase process in which the immune system is first sensitized to an allergen and then a reaction is elicited when the immune system is subsequently challenged by the allergen. Sensitization initiates the production of IgE antibodies, which ultimately attach to mast cells. In the challenge phase, allergen interacts with IgE antibodies resulting in release of cytokines and histamine. The allergen model induces a hypersensitivity reaction unaided by adjuvants or other agents that cause immune activation. Methods to test allergens without adjuvants in rat models involve breeding animals raised on feed lacking the allergen to be tested, e.g., peanut or soy, for three or more generations. Subsequent introduction of the allergen, e.g., via concentrated peanut extract demonstrates an induction of allergic response. Addition of an adjuvant to the sensitization process has been shown to enhance the allergic reaction measured (de Jonge et al. 2007). The most common adjuvant is cholera toxin and other suitable toxins can be used including staphylococcal enterotoxin B (SEB) stimulate enhanced reactions as well (Ganeshan et al. 2009). Female rats show a stronger response compared to males and experimental groups are sorted by sex for this reason.

To test the preventative effect of a bacterial composition, rats are bred for three generations lacking soy and peanut based-feed. The third generation animals are treated with a bacterial composition or with buffer alone administered via oral gavage for one or more weeks. Subsequently both cohorts of rats are orally sensitized to peanut specific allergens by administering 1-10 mg of peanut extract for 6 weeks via oral gavage. Optionally, rats may be pre-treated with the bacterial composition with or without an antibiotic treatment phase. Serum levels of antigen-specific antibodies IgG2a, IgG1, IgE and Rat Mast Cell Protease II (RMCPII) are monitored for immunological response 1 week before sensitization (day −7), and 2, 4, and 6 weeks after initial exposure. Initial antibody production, specifically IgE, is indicative of the sensitization reaction and first phase of the immunological hypersensitivity response. The RMCPII response is a specific indicator of mast cell activation prior to challenge phase of the hypersensitivity reaction.

Additional cohorts of test and control animals may be treated to measure the induction of organ-specific immune responses, such as the accumulation of antigen-specific or non-antigen-specific regulatory T cells and Th17 T cells in the colon and small intestine. Briefly, sections of various segments of the small intestine and colon are collected from test and control animals as previously described in Yang et al., 2013. Fragments of tissue are fixed in 10% formalin, transferred in sterile phosphate buffered saline (PBS), and stored at 4° C. for histological and immune-staining techniques using methods known to those skilled in the art (e.g., see Barletta et al., 2013, Atarashi et al., 2013). Briefly, 3-7 µm sections of tissue are prepared, stained with antibody reagents that can identify PE antigen-specific regulatory T cells and Th17+ T cells. Cell infiltration into the intestinal tissue is evaluated by comparing cell counts between samples derived from test animals and control animals.

To test the therapeutic effect of a bacterial test composition, the procedure specified above is repeated with the bacterial test composition administered daily for 1 week after the 6 weeks of sensitization. The rats are divided into a control group and a test group where the control group receives water while the test group receives the bacterial test composition for the 1-week period. Additionally, rats may be pre-treated with or without an antibiotic treatment phase for 1 week prior to the bacterial composition. The animals are challenged on weeks 2, 4, and 6 with 1-10 mg of peanut extract and the panel of readouts indicates the therapeutic effect of the bacterial test composition compared to control. Alternative dosing schedules and routes of administration (e.g., rectal) may be employed, including multiple doses of test article, and $10^3$ to $10^{10}$ cfu/ml of a bacterial composition may be delivered.

Compositions that decrease an indication of allergic effect are useful for treating or inhibiting an allergic effect.

Example 2: Oral Food Allergy with Peanut Extract in Murine Models

Murine models are commonly sensitized to food allergens for the examination of prophylactic, curative treatments and desensitization protocols (Bashir et al., 2004, Li et al., 2000). These models sensitize animals and subsequently challenge them with an allergen monitoring both clinical symptoms of anaphylaxis and biomarkers of hypersensitivity in the form of increased PE-specific IgE and proinflammatory cytokines. To test the therapeutic effect of the bacterial composition, five-week-old C3H/HeJ, female mice are raised on allergen-free chow under pathogen-free conditions. C3H/HeJ mice have a mutant TLR-4 gene making them hypersensitive to food allergens and subsequent sensitization procedures. Mice are sensitized to an allergen, e.g., peanut extract (PE) or purified Ara h1 (as described in Bashir et al. 2004, supra), by weekly oral administration of 1-10 mg allergen with 20 µg of cholera toxin (CT) for five weeks followed by 1-50 mg allergen+20 µg CT booster doses at weeks 6 and 8. Mice are separated into two groups, a control group receiving only the buffer (Group 1) and a test group receiving the bacterial composition in a liquid matrix (Group 2). Both groups are administered control or treatment twice daily for 1 week. The treatment group receives $10^3$-$10^{10}$ cfu/ml of the bacterial composition with an optional prior 1 week antibiotic treatment. Antibiotic treatment includes a 7 day treatment with 5 to 7 antibiotics (including kanamycin, colistin, gentamycin, metronidazole and vancomycin and optionally including ampicillin and ciprofloxacin) delivered via drinking water, followed by a single dose containing clindamycin on day 5 of that week. Animals are challenged starting on week 14 and every 4 weeks after that (i.e., week 14, 18, 22, 28, 34, 40, 44, 48, 52) through week 52. To determine the protective effects of the bacterial composition, anaphylactic signs are evaluated 30 minutes following treatment in a blinded fashion. Plasma histamine levels, serum peanut-specific IgE, IgA, and IgG2a are assessed as previously described (Bashir et al., 2004, supra; Srivastava et al., 2011, supra). Additionally, serum levels of one or more of IL-1 beta (IL-1β), IL-1ra, IL-2, IL-4, IL-5, IL-6, IL-7, IL-9, IL-10, IL-12 (p70), IL-13, IL-15, IL-17, interferon-gamma (IFN-γ), tumor necrosis factor-alpha (TNFα), and tumor growth factor (TGF-β) are tested. Histological and immunostaining techniques described in Example 1 are performed to evaluate antigen specific regulatory T cell infiltration into the small intestine and colon (described by Atarashi et al., 2013, supra, Barletta et al., 2013, supra). Cell counts of regulatory T cells and Th17 cells from tissue samples can also be performed using immunostaining and flow cytometry techniques known in the art (e.g., Atarashi et al., 2013, supra). The prophylactic effect of a bacterial composition is tested by repeating the above protocol with the following modification: a bacterial composition with an optional, prior 1 week antibiotic treatment and control treatment is administered before the sensitization study via oral lavage twice daily for 1 week with concentrations ranging from $10^3$-$10^{10}$ cfu/ml. Antibiotic treatment includes a 7 day treatment with 5 to 7 antibiotics (including kanamycin, colistin, gentamycin, metronidazole and vancomycin and optionally including ampicillin and ciprofloxacin) delivered via their drinking water, followed by a single dose with clindamycin on day 5 of that week. Twice daily bacterial composition treatment is optionally continued throughout the sensitization and challenge procedure as described above and as is known in the art. Alternative dosing schedules and routes of administration (e.g., rectal) may be employed, including multiple doses of test composition, and $10^3$ to $10^{10}$ cfu/ml of a selected bacterial composition are delivered.

Example 3: In Vivo Assays Establishing Protective Effect of Bacterial Compositions from OVA Food Allergy BALB/c ILraF709, 8-12 week old, female mice are sensitized to chicken egg ovalbumin (OVA) with a 100-200 µg intragastric dose of OVA with (optional) 10 µg staphylococcal enterotoxin B (SEB) once a week for 8 weeks. Mice are tested for allergic protection against anaphylaxis by a treatment protocol with and without inclusion of the bacterial composition explained in the following protocol. The test group receives a 7-day treatment with 5 to 7 antibiotics (including kanamycin, colistin, gentamycin, metronidazole and vancomycin and optionally including ampicillin and ciprofloxacin) delivered via their drinking water, followed by a single dose with Clindamycin on day 5th day of that week. The control group receives regular sterile water. Both groups are then challenged with 5 µg or 150 µg of OVA and are examined for anaphylaxis reaction via body temperature checked every 5 minutes and symptom scoring as defined previously (Matias et al., 2010). Bacterial compositions are given after sensitization procedure to test the protective capacity of the treatment. Additionally, the procedures are repeated with the test group receiving antibiotic treatment and bacterial composition treatment after an initial anaphylaxis test and then administered a second anaphylaxis test for comparison. This procedure is used to test the prophylactic capacity of the bacterial composition by treating mice with the antibiotic and bacterial compositional treatment before the sensitization procedure, as specified above. The test group is evaluated by the challenge procedure specified above examining symptoms and body temperature. Alternative dosing schedules and routes of administration (e.g. rectal) may be employed, including multiple doses of test compositions, and $10^3$ to $10^{10}$ cfu/ml of a given bacterial composition are delivered. Furthermore, fecal material before and after antibiotic treatment and bacterial composition administration is analyzed by 16S and whole genome sequencing techniques. Spore counts and identity are examined and fecal material is provided for functional analysis for presence of short chain fatty acids and other metabolites.

Example 4: In Vitro Examination Effects of Bacterial Composition of Cell Culture and Cytokine Measurements The challenge phase of the allergic reaction involves over-production of proinflammatory cytokines by immune cells. To determine the cytokine production of antigen primed Th2 cells, splenocytes are isolated for mice sensitized in Example 2 and cultured as specified previously (Srivastava et al 2010) in the presence or absence of 200 mg/ml crude peanut extract with or without various titrations ranging from $10^3$-$10^{10}$ cfu/ml of bacterial compositions for 24 hours at 37° C. Cells are centrifuged and supernatant will be tested for the concentration of one or more of the following: interleukin-1 beta (IL-1β), IL-1ra, IL-2, IL-4, IL-5, IL-6, IL-7, IL-9, IL-10, IL-12 (p70), IL-13, IL-15, IL-17, Interferon-gamma (IFN-γ), Tumor Necrosis Factor-alpha (TNFα), and Tumor Growth Factor (TGF-β). Experiments are repeated with Caco-2 cells in the presence or absence of titrations ranging from $10^3$-$10^{10}$ cfu/ml of bacterial compositions. LPS (1 μg/ml) serves as a positive control (See, e.g., Vitali et al., 2012).

Example 5: Effects of Bacterial Composition on B Cell IgE Production In Vitro

Food allergy hypersensitivity is mediated by the over production of IgE. Human U266 B cell culture is assessed to measure the direct effect of bacterial composition exposure on IgE production. $2 \times 10^5$ cells/ml of human myeloma cells (e.g., a U266 B cell line) are cultured in RPMI 1640 medium with appropriate supplements in the absence or presence of various concentrations ranging from $10^3$-$10^{10}$ cfu/ml of the bacterial composition for 24 hours at 37 C. IgE concentrations are measured in the supernatant as previously described (Srivastava et al 2010). A decrease in IgE concentration indicates a protective effect from the bacterial composition.

Example 6: Asthma Mouse Assay

The efficacy of the bacterial compositions of the present invention are demonstrated by modulating asthmatic responses in a sensitized mouse model subsequently challenged with aerosolized turkey egg albumin (OVA) with and without bacterial composition treatment. 5-6 week old, male and female mice are housed in high-efficiency particulate filtered air (HEPA) laminar flow hoods in a virus and antigen free facility and feed ad libitum. Mice are sensitized by intraperitoneal injection of 20 μg of OVA and 4 mg of $Al(OH)_3$ in 0.1 ml of saline solution on day 0 and 14. The test group of mice is administered a 7 day treatment with 5 to 7 antibiotics (including kanamycin, colistin, gentamycin, metronidazole and vancomycin and optionally including ampicillin and ciprofloxacin) delivered via their drinking water, followed by a single dose with Clindamycin on day 5 day of that week. The bacterial composition is then administered at a concentration ranging from $10^3$-$10^{10}$ cfu/ml twice daily via oral lavage for a week from day 21 to day 28. The control group receives regular sterile water and no antibiotic or bacterial composition. Both groups are challenged with aerosolized 1% OVA saline solution for 30 minutes per day for 3 days. Negative controls are treated with saline alone. 24 hours after the last challenge, airway hyper-responsiveness is assessed with challenge by aerosolized methacholine, blood samples are collected and bronchoaveolar lavage (BAL) is performed (See, e.g., Williams et al., 2012; see also US20040076607). Airway hyper responsiveness is evaluated as previously described and otherwise known in the art. Briefly, mice are anesthetized, intubated and ventilated using a FlexiVent instrument with a tidal volume of 0.3 ml at 150 breaths/min. The chest cavity is opened to atmospheric pressure and static elastic properties are assessed by repeatedly inflating and deflating the lungs. Pulmonary mechanics are evaluated after challenging with methacholine treatment as previously described. Blood serum is taken for IgG analysis, and cytokine analysis before the sensitization, after, the challenge, and after the airway hyper responsiveness test. Serum levels of OVA-specific IgE, IgA, IgG1, IgG2a are measured using standard techniques generally known in the. One or more serum cytokines are measured including interleukin-1 beta (IL-1β), IL-1ra, IL-2, IL-4, IL-5, IL-6, IL-7, IL-9, IL-10, IL-12 (p70), IL-13, IL-15, IL-17, interferon-gamma (IFN-γ), tumor necrosis Factor-alpha (TNFα), and tumor growth factor (TGF-β) are measured using an ELISA based method (See, e.g., Bashir et al., 2004; Srivastava et al., 2011). BAL materials are evaluated by washing the lungs twice with PBS and collecting the BAL fluid. Total protein analysis is analyzed using standard techniques. Specific protein levels are measured including one or more of the following: interleukin-1 beta (IL-1β), IL-1ra, IL-2, IL-4, IL-5, IL-6, IL-7, IL-9, IL-10, IL-12 (p70), IL-13, IL-15, IL-17, Interferon-gamma (IFN-γ), TNFα, and TGF-β by ELISA based techniques. In addition, feces are collected throughout and submitted for 16S sequencing, whole genome sequencing, and mass spectrometry analysis to characterize functional metabolites, including but not limited to short chain fatty acids and antioxidants. The bacterial compositions result in reduced levels of clinical signs of airway hyperactivity, reduced serum OVA specific-IgE levels, and improved anti-inflammatory cytokine compared to pro-inflammatory cytokine profiles, e.g., IL-10 is increased while IL-2 is decreased.

To demonstrate the prophylactic ability of the bacterial composition to aid in reducing or preventing asthma in this mouse model, the tests are repeated with the 7 day antibiotic treatment followed by the 7 day bacterial composition treatment being administered before the sensitization and challenge procedure. Furthermore, bacterial composition treatment is optionally administered concurrently throughout the sensitization and challenge period. Dosing of bacterial compositions is provided at various concentrations ranging from $10^3$-$10^{10}$ cfu/ml given twice daily. The above assays are repeated to assess the prophylactic effect on the mouse model. Alternative dosing schedules and routes of administration (e.g., rectal) may be employed, including multiple doses of test compositions, and $10^3$ to $10^{10}$ cfu/ml of a given organism or compositions are delivered.

Example 7: Allergy Model Using Gnotobiotic Mice

In another murine model useful for testing a bacterial composition for the ability to ameliorate an allergic response, gnotobiotic mice are used. Briefly, germ free mice, e.g., C57BL/6, are maintained in an appropriate facility such as a specific pathogen free (SPF) facility. Methods of preparing an maintaining germ free mice are known in the art. In preparation for analyzing the ability of a test composition to prevent an allergic response, e.g., signs or symptoms of anaphylaxis, germ free mice are prepared as described above or as described in, e.g., Stefka et al., 2014, PNAS USA, pnas.org/cgi/doi/10.1073/pnas.1412008111) using antibiotic treatment and sensitization to peanut allergen/cholera toxin. Prepared mice either challenged with allergen the treated with a test composition (i.e., to test for the ability of a composition to acutely treat an allergen induced reaction; or are treated with a test composition prior to exposure to an allergen. To evaluate the efficacy of the test composition, indicators of allergic response (e.g., anaphylactic response) are analyzed such as serum levels of peanut allergen specific IgE, serum levels of allergen-specific IgG1, and core body temperature. Results are compared to control mice, e.g., mice that were sensitized but not exposed to allergen or to a known reference, e.g., normal body temperature.

Example 8: Cow Milk Allergy Sensitivity Reduction

To demonstrate a bacterial composition's ability to reduce allergic sensitivity to food, a group of 30 subjects with confirmed cow's milk allergy (experimental group) is prospectively assembled, along with 30 non-allergic controls (control group). Cow's milk allergy is confirmed by positive double-blind placebo controlled milk challenge and positive skin prick test or detectable serum milk specific IgE level. Maximum dose tolerated, baseline basophil reactivity, wheal size, and IgE and IgG levels are measured during the physician supervised, double-blinded placebo controlled milk challenges conducted during subject screening. During a pre-treatment period of 10 weeks, the experimental treatment group receives double-blinded a daily oral dose of about $1\times10^9$ cfus of viable bacteria either in the form of vegetative organisms or spores or both, whereas the control group is administered double-blinded placebo at an identical dosing and frequency. The bacterial composition may optionally be co-administered with a non-stimulatory amount of milk protein allergen. The bacterial composition is formulated in a delayed release capsule or co-administered with bicarbonate buffer to aid passage of viable organisms through the stomach. Patients are optionally treated with a broad spectrum antibiotic 0-3 days prior to administration of the bacterial composition. Alternative dosing schedules and routes of administration (e.g. rectal) are employed, including multiple doses of test article, and $10^3$ to $10^{10}$ of a given composition are delivered.

At the end of the 10-week pre-treatment period, subjects continue the same regimen of either experimental treatment or placebo for 8 weeks with physician supervised, double-blinded placebo controlled milk challenges conducted at 0, 4, and 8 weeks after the end of the pre-treatment period to measure maximum dose tolerated, basophil reactivity, wheal size, and IgE and IgG levels.

At end of the 8 week initial challenge period, a majority of subjects in the experimental group are expected to show tolerance to milk, demonstrated by increased maximum dose tolerated and reduction in basophil reactivity, wheal size, and/or immunoglobulin levels during controlled milk challenges. At the end of the 8 week initial challenge period, subjects that show tolerance to milk will be taken off the experimental treatment or placebo and return for physician supervised, double-blinded placebo controlled milk challenges after 2 weeks, 4 weeks, 8 weeks, 16 weeks, 32 weeks, and 52 weeks to measure maximum dose tolerated, basophil reactivity, wheal size, and IgE and IgG levels. A significant number of subjects will show sustained tolerance to milk during the follow-up period demonstrated by a maximum dose tolerated that is above baseline levels at study start and reduction in basophil reactivity, wheal size, and/or immunoglobulin levels during controlled milk challenges compared to baseline levels.

Example 8: Food Allergen Sensitivity Reduction

To demonstrate a bacterial composition's ability to reduce allergic sensitivity to food allergens in combination with oral immunotherapy, a group of 60 subjects with confirmed peanut allergy (experimental group) is prospectively assembled. Peanut allergy is confirmed by positive double-blind placebo controlled peanut allergen challenge and positive skin prick test or ImmunoCAP IgE level to peanut>10 kU/L. Baseline basophil reactivity, wheal size, and IgE levels will be measured during the physician supervised, double-blinded placebo controlled peanut allergen challenges conducted during subject screening.

During a pre-treatment period of 10 weeks, the experimental treatment group receives double-blinded a daily oral dose of about $1\times10^9$ cfus of viable bacteria either in the form of vegetative organisms or spores or both, whereas the control group is administered double-blinded placebo at an identical dosing and frequency. The bacterial composition may optionally be co-administered with a non-stimulatory dose of peanut allergen. The composition is formulated in a delayed release capsule or co-administered with bicarbonate buffer to aid passage of viable organisms through the stomach. Patients are optionally treated with a broad spectrum antibiotic 0-3 days prior to administration of the bacterial composition. Alternative dosing schedules and routes of administration (e.g., rectal) can be employed, including multiple doses of test article, or delivery of bacterial composition and non-stimulatory amounts of peanut allergen on complementary schedules (e.g., one day before, on the same day, or one day after) and $10^3$ to $10^{10}$ of a given composition are delivered. At the end of the 10-week pre-treatment period, subjects begin oral immunotherapy, continuing the same regimen of either experimental treatment or placebo. Oral immunotherapy begins with an initial day escalation phase in which peanut allergen doses are given every 30 minutes beginning at 0.1 mg peanut protein and doubling with each dose given. Highest tolerated dose is the starting dose for the buildup phase, in which subjects are given daily doses of peanut allergen and doses escalate biweekly for 30 weeks, increasing by 50-100% until 75 mg dose, at which point increases are at 25-33% until 4000 mg maintenance dose is achieved. After reaching week 30, subjects continue on daily doses of the highest dosage of peanut allergen achieved in the buildup phase for 1 month before oral challenge. Oral challenge consists of physician-supervised, double-blinded placebo controlled peanut allergen challenges conducted to measure maximum dose of peanut allergen tolerated, baseline basophil reactivity, wheal size, and IgE levels.

By the end of the pretreatment and oral immunotherapy period, the experimental group will show increased desensitization to peanut allergen compared to the control group, demonstrated by larger increases in maximum dose tolerated and greater reduction in basophil reactivity, wheal size, and/or immunoglobulin levels during controlled peanut allergen challenges.

After the first oral challenge, subjects that show desensitization to peanut allergen will be taken off the experimental treatment or placebo and will return for physician supervised, double-blinded placebo controlled peanut allergen challenges after 2 weeks, 4 weeks, 8 weeks, 16 weeks, 32 weeks, and 52 weeks to measure maximum dose tolerated, basophil reactivity, wheal size, and IgE levels. The experimental group is expected to show greater tolerance to peanut allergen during the follow-up period compared to the control group, demonstrated by higher maximum dose tolerated above baseline levels at study start and greater reduction in basophil reactivity, wheal size, and/or immunoglobulin levels during controlled peanut allergen challenges compared to baseline levels.

Example 9: Prevention of Allergen-Induced Airway Obstruction

To demonstrate a bacterial composition's ability to prevent allergen-induced airway obstruction, a group of 30 subjects with mild to moderate asthma (experimental group) is prospectively assembled, along with 30 non-asthmatic controls (control group). Subjects must have a diagnosis of stable, mild to moderate asthma and a positive skin prick test for at least one common aeroallergen. Baseline methacholine PC20 (allergen concentration required for a 20% drop in Forced Expiratory Volume at One Second, FEV1) will be measured during subject screening using standard methacholine challenge to test airway responsiveness.

During a pre-treatment period of 10 weeks, the experimental treatment group receives double-blinded a daily oral dose of about $1 \times 10^9$ cfus of viable bacteria either in the form of vegetative organisms or spores or both, whereas the control group is administered double-blinded placebo at an identical dosing and frequency. The composition can be formulated in a delayed release capsule or co-administered with bicarbonate buffer to aid passage of viable organisms through the stomach. Patients may be optionally treated with a broad spectrum antibiotic 0-3 days prior to administration of the bacterial composition. Alternative dosing schedules and routes of administration (e.g., rectal) are employed, including multiple doses of test article, and $10^3$ to $10^{10}$ of a given composition are delivered.

At the end of the 10-week pre-treatment period, subjects continue the same regimen of either experimental treatment or placebo for 8 weeks with methacholine PC20 measured biweekly to test airway responsiveness. By the end of the 8 week initial challenge period, a majority of subjects in the experimental group are expected to show sustained decrease in airway responsiveness, demonstrated by declined methacholine PC20 compared to baseline. At the end of the 8 week initial challenge period, subjects showing decreased airway responsiveness will be taken off the experimental treatment or placebo and return for methacholine challenge after 2 weeks, 4 weeks, 8 weeks, 16 weeks, 32 weeks, and 52 weeks for measurement of methacholine PC20. A significant number of subjects in the experimental group will show sustained decrease in airway responsiveness during the follow-up period as compared to study start, demonstrated by lower methacholine PC20 as compared to baseline.

Unless otherwise indicated, all numbers expressing quantities of ingredients, reaction conditions, and so forth used in the specification, including claims, are to be understood as being modified in all instances by the term "about." Accordingly, unless otherwise indicated to the contrary, the numerical parameters are approximations and may vary depending upon the desired properties sought to be obtained. At the very least, and not as an attempt to limit the application of the doctrine of equivalents to the scope of the claims, each numerical parameter should be construed in light of the number of significant digits and ordinary rounding approaches.

Unless otherwise indicated, the term "at least" preceding a series of elements is to be understood to refer to every element in the series.

Other embodiments will be apparent to those skilled in the art from consideration of the specification and practice of the embodiments. Consider the specification and examples as exemplary only, with a true scope and spirit being indicated by the following claims.

What is claimed is:

1. A method of identifying a bacterial composition useful for treating, preventing, or reducing the severity of an allergic effect, the method comprising:
   a) subjecting a test subject or group of test subjects to an antibiotic treatment;
   b) administering a bacterial test composition to the test subject or group of test subjects;
   c) administering an allergen to the test subject or group of test subjects;
   d) measuring an allergic effect in the test subject or group of test subjects;
   e) comparing the allergic effect measured in the test subject or group of test subjects to an allergic effect measured in a corresponding control subject or group of control subjects; and
   f) identifying the bacterial test composition as useful for treating, preventing or reducing the severity of an allergic effect if the allergic effect measured in the test subject or group of test subjects is less than the allergic effect measured in the corresponding control subject or group of control subjects.

2. The method of claim 1, wherein the allergen is a food antigen.

3. The method of claim 1, wherein the allergic effect is selected from the group consisting of plasma histamine level, serum antigen-specific IgE level, serum antigen-specific IgA level, serum antigen-specific IgG2a level, serum IL-1 beta (IL-1β) level, serum IL-1ra level, serum IL-2 level, serum IL-4 level, serum IL-5 level, serum IL-6 level, serum IL-7 level, serum IL-9 level, serum IL-10 level, serum IL-12 (p70) level, serum IL-13 level, serum IL-15 level, serum IL-17 level, interferon-gamma (IFN-γ) level, tumor necrosis factor-alpha (TNFα) level, tumor growth factor (TGF-β) level, Th17 cell activity, gut permeability and specific regulatory T cell infiltration into the small intestine and/or colon, or allergen-specific IgE production or airway hyperresponsiveness.

4. The method of claim 1, wherein the test and control subjects are gnotobiotic subjects.

5. The method of claim 1, wherein the bacteria test composition is administered at a concentration of $10^3$ to $10^{10}$ cfu/ml.

6. The method of claim 1, wherein the antibiotic treatment comprises a 7 day treatment with 5 to 7 antibiotics selected from the group consisting of kanamycin, colistin, gentamycin, metronidazole, vancomycin, ampicillin, and ciprofloxacin.

7. The method of claim 1, wherein the allergic effect is cytokine production.

8. The method of claim 7, wherein the cytokine is selected from the group consisting of: interleukin-1 beta (IL-1β), IL-1ra, IL-2, IL-4, IL-5, IL-6, IL-7, IL-9, IL-10, IL-12 (p70), IL-13, IL-15, IL-17, interferon-gamma (IFN-γ), tumor necrosis factor-alpha (TNFα), and tumor growth factor (TGF-β).

9. The method of claim 1, wherein the allergic effect is over production of IgE.

10. The method of claim 1, wherein the allergic effect is associated with asthma.

11. The method of claim 1, further comprising sensitizing the test and control subjects to peanut, soy, cow milk, or egg albumin.

* * * * *